(12) United States Patent
Suh et al.

(10) Patent No.: US 11,864,461 B2
(45) Date of Patent: Jan. 2, 2024

(54) ORGANIC COMPOUND AND ORGANIC LIGHT-EMITTING DEVICE COMPRISING SAME

(71) Applicant: LG CHEM, LTD., Seoul (KR)

(72) Inventors: Sang Duk Suh, Daejeon (KR); Ji Young Choi, Daejeon (KR); Woochul Lee, Daejeon (KR); Joo Ho Kim, Daejeon (KR); Hoon Jun Kim, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 626 days.

(21) Appl. No.: 17/041,297

(22) PCT Filed: Oct. 4, 2019

(86) PCT No.: PCT/KR2019/013004
§ 371 (c)(1),
(2) Date: Sep. 24, 2020

(87) PCT Pub. No.: WO2020/080714
PCT Pub. Date: Apr. 23, 2020

(65) Prior Publication Data
US 2021/0020844 A1    Jan. 21, 2021

(30) Foreign Application Priority Data

Oct. 16, 2018 (KR) .......... 10-2018-0123080

(51) Int. Cl.
| | | |
|---|---|---|
| H01L 51/50 | (2006.01) | |
| H10K 85/60 | (2023.01) | |
| H10K 50/12 | (2023.01) | |

(52) U.S. Cl.
CPC .......... H10K 85/653 (2023.02); H10K 50/12 (2023.02)

(58) Field of Classification Search
None
See application file for complete search history.

(56) References Cited

U.S. PATENT DOCUMENTS

2004/0251816 A1   12/2004  Leo et al.
2015/0364693 A1*  12/2015  Ito ................... H10K 85/654
                                              257/40

(Continued)

FOREIGN PATENT DOCUMENTS

CN      108463535 A      8/2018
CN      110317186 A     10/2019
(Continued)

*Primary Examiner* — Gregory D Clark
(74) *Attorney, Agent, or Firm* — Bryan Cave Leighton Paisner LLP

(57) ABSTRACT

The present specification relates to a compound represented by the following Formula 1 and an organic light emitting device including the same. The compound is used as a material for an organic material layer of the organic light emitting device.

[Formula 1]

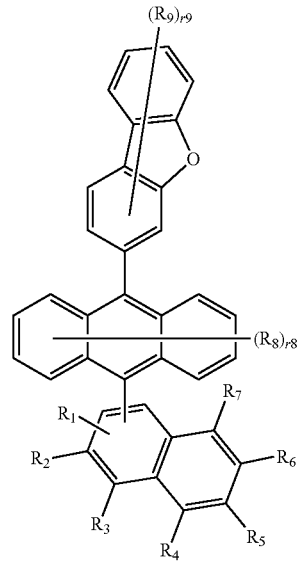

9 Claims, 1 Drawing Sheet

(56) References Cited

U.S. PATENT DOCUMENTS

| | | |
|---|---|---|
| 2016/0005980 A1 | 1/2016 | Ito et al. |
| 2018/0277771 A1 | 9/2018 | Park et al. |
| 2019/0305227 A1 | 10/2019 | Yoon et al. |
| 2021/0395215 A1 | 12/2021 | Kim et al. |
| 2021/0399223 A1 | 12/2021 | Suh et al. |
| 2022/0006019 A1 | 1/2022 | Kim et al. |

FOREIGN PATENT DOCUMENTS

| | | |
|---|---|---|
| CN | 111448679 A | 7/2020 |
| CN | 112567544 A | 3/2021 |
| CN | 112930382 A | 6/2021 |
| CN | 112955523 A | 6/2021 |
| JP | 2011-100942 A | 5/2011 |
| KR | 10-2014-0083107 A | 7/2014 |
| KR | 10-2017-0039020 A | 4/2017 |
| KR | 10-2018-0068861 A | 6/2018 |
| KR | 10-2018-0072058 A | 6/2018 |
| KR | 10-2018-0081005 A | 7/2018 |
| WO | 2018/110887 A1 | 6/2018 |

\* cited by examiner

[Figure 1]
[Figure 2]
[Figure 3]
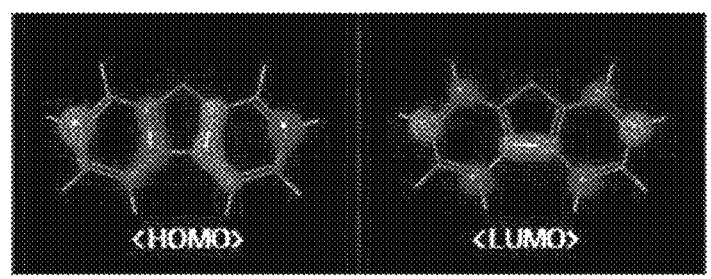

ORGANIC COMPOUND AND ORGANIC LIGHT-EMITTING DEVICE COMPRISING SAME

TECHNICAL FIELD

The present specification relates to an organic compound and an organic light emitting device including the same.

This application claims priority to and the benefit of Korean Patent Application No. 10-2018-0123080 filed in the Korean Intellectual Property Office on Oct. 16, 2018, the entire contents of which are incorporated herein by reference.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer has in many cases a multi-layered structure composed of different materials in order to improve the efficiency and stability of the organic light emitting device, and for example, may be composed of a hole injection layer, a hole transport layer, a light emitting layer, an electron transport layer, an electron injection layer, and the like. In such a structure of the organic light emitting device, if a voltage is applied between the two electrodes, holes are injected from the positive electrode into the organic material layer and electrons are injected from the negative electrode into the organic material layer, and when the injected holes and electrons meet each other, an exciton is formed, and light is emitted when the exciton falls down again to a ground state.

There is a continuous need for developing a new material for the aforementioned organic light emitting device.

[Prior Art Document] US Patent Application Publication No. 2004-0251816

DETAILED DESCRIPTION OF THE INVENTION

Technical Problem

The present specification provides an organic compound and an organic light emitting device including the same.

Technical Solution

An exemplary embodiment of the present specification provides a compound represented by the following Formula 1.

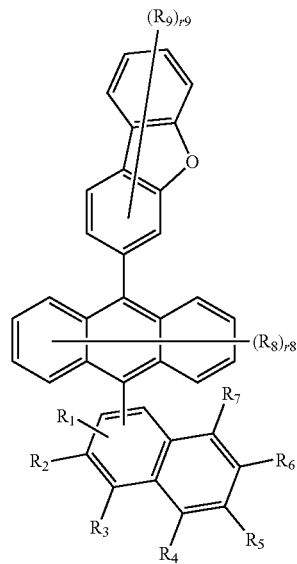

[Formula 1]

In Formula 1, $R_1$ to $R_7$ are the same as or different from each other, and are each independently hydrogen, deuterium, or a substituted or unsubstituted aryl group, $R_8$ and $R_9$ are the same as or different from each other, and are each independently hydrogen or deuterium, r8 is an integer from 0 to 8, r9 is an integer from 0 to 7, and when r8 and r9 are each 2 or higher, the substituents in the parenthesis are the same as or different from each other, the following compound is excluded from the compound represented by Formula 1, provided that at least one of $R_1$ to $R_7$ is a substituted or unsubstituted aryl group.

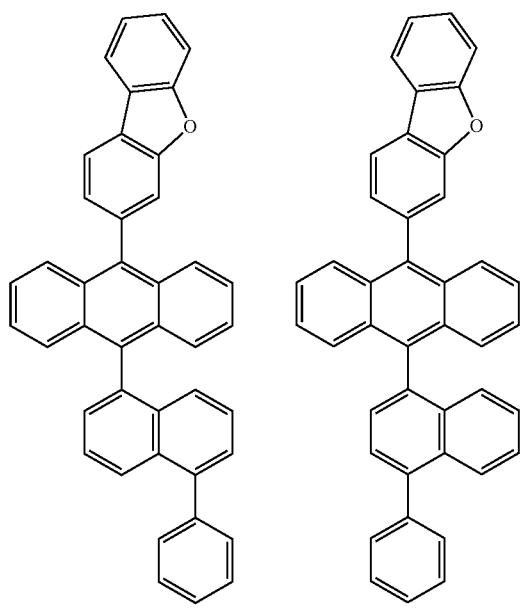

-continued

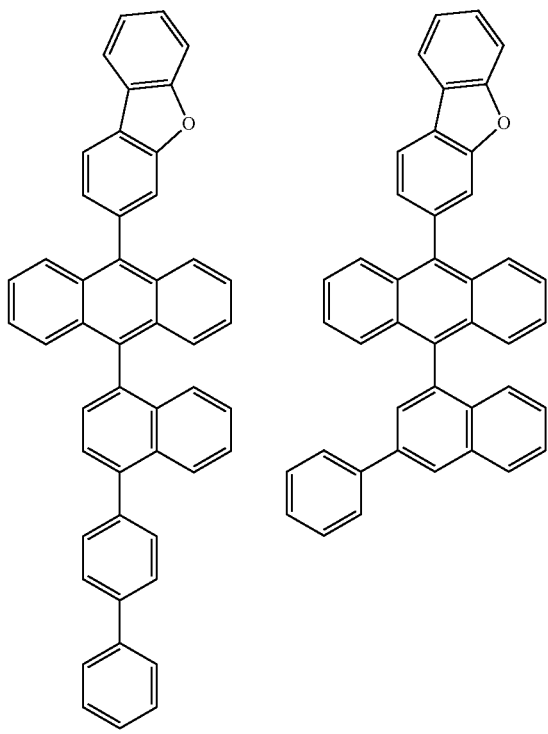

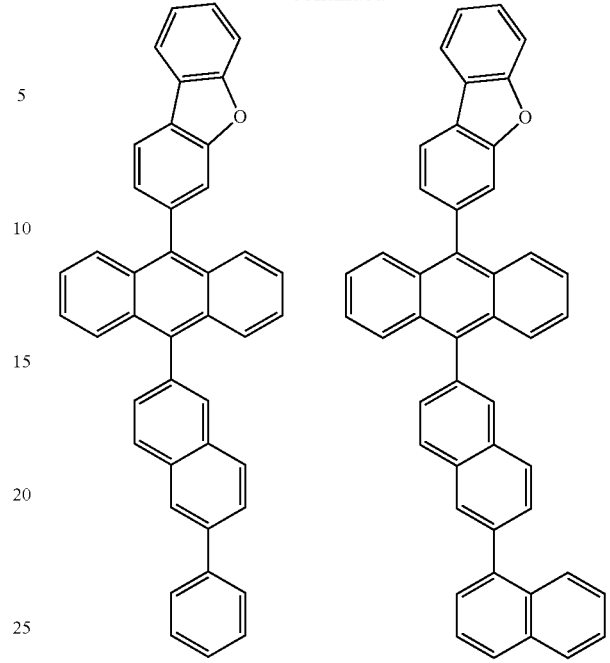

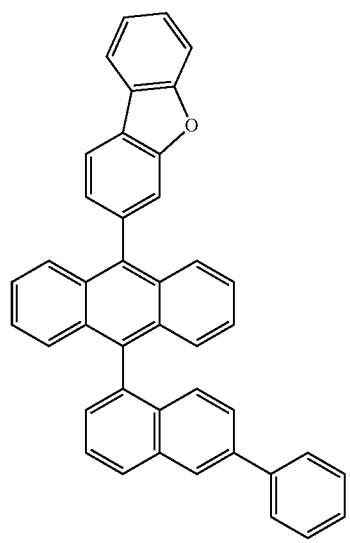

Further, the present specification provides an organic light emitting device including: a first electrode; a second electrode provided to face the first electrode; and an organic light emitting layer having one or more layers provided between the first electrode and the second electrode, in which one or more layers of the organic material layer include the compound.

Advantageous Effects

The compound according to an exemplary embodiment of the present specification may be used as a material for an organic material layer of an organic light emitting device, and it is possible to improve efficiency, achieve a low driving voltage, and/or improve service life characteristics, in the organic light emitting device by using the compound.

BRIEF DESCRIPTION OF DRAWINGS

FIG. 1 illustrates an organic light emitting device according to an exemplary embodiment of the present specification.
FIG. 2 illustrates an organic light emitting device according to an exemplary embodiment of the present specification.
FIG. 3 is a view illustrating the HOMO and LUMO of dibenzofuran.

EXPLANATION OF REFERENCE NUMERALS AND SYMBOLS

1: Substrate
2: First electrode
3: Organic material layer
4: Second electrode
5: Hole injection layer
6: Hole transport layer
7: Electron blocking layer
8: Light emitting layer 9: Electron transport layer
10: Electron injection layer

BEST MODE

Hereinafter, the present specification will be described in more detail.

The present specification provides the compound represented by Formula 1.

The compound represented by Formula 1 of the present specification is characterized in that the position No. 3 of dibenzofuran and naphthalene are bonded to the central anthracene, and an aryl group is substituted on naphthalene. The position No. 3 of dibenzofuran is a moiety where both the HOMO and LUMO are located, affects the HOMO and LUMO of anthracene, and thus enables excellent transport of holes and electrons, which is required by a host material of a light emitting layer.

Further, the morphology of a film, the distance between host materials, and the like can be adjusted by substituting various aryl groups on naphthalene, so that when the compound represented by Formula 1 is applied to an organic light emitting device, the device having a low voltage, a long service life, and high efficiency may be obtained.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

In the present specification,

means a moiety bonded to another substituent or a bonding portion.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a nitrile group; an alkyl group; a silyl group; an alkoxy group; an arylamine group; and aryl group; and a heterocyclic group, being substituted with a substituent to which two or more substituents among the exemplified substituents are linked, or having no substituent. For example, "the substituent to which two or more substituents are linked" may be an aryl group substituted with an aryl group, an aryl group substituted with a heteroaryl group, a heterocyclic group substituted with an aryl group, an aryl group substituted with an alkyl group, and the like.

In the present specification, an alkyl group may be straight-chained or branched, and the number of carbon atoms thereof is not particularly limited, but is preferably 1 to 30. Specifically, the number of carbon atoms thereof is preferably 1 to 20. More specifically, the number of carbon atoms thereof is preferably 1 to 10. Specific examples thereof include: a methyl group; an ethyl group; a propyl group; an n-propyl group; an isopropyl group; a butyl group; an n-butyl group; an isobutyl group; a tert-butyl group; a sec-butyl group; a 1-methylbutyl group; a 1-ethylbutyl group; a pentyl group; an n-pentyl group; an isopentyl group; a neopentyl group; a tert-pentyl group; a hexyl group; an n-hexyl group; a 1-methylpentyl group; a 2-methylpentyl group; a 4-methyl-2-pentyl group; a 3,3-dimethylbutyl group; a 2-ethylbutyl group; a heptyl group; an n-heptyl group; a 1-methylhexyl group; a cyclopentylmethyl group; a cyclohexylmethyl group; an octyl group; an n-octyl group; a tert-octyl group; a 1-methylheptyl group; a 2-ethylhexyl group; a 2-propylpentyl group; an n-nonyl group; a 2,2-dimethylheptyl group; a 1-ethylpropyl group; a 1,1-dimethylpropyl group; an isohexyl group; a 2-methylpentyl group; a 4-methylhexyl group; a 5-methylhexyl group; and the like, but are not limited thereto.

In the present specification, an alkoxy group may be straight-chained, branched, or cyclic. The number of carbon atoms of the alkoxy group is not particularly limited, but is preferably 1 to 30. Specifically, the number of carbon atoms thereof is preferably 1 to 20. More specifically, the number of carbon atoms thereof is preferably 1 to 10. Specific examples thereof include a methoxy group; an ethoxy group; an n-propoxy group; an i-propyloxy group; an n-butoxy group; an isobutoxy group; a tert-butoxy group; a sec-butoxy group; an n-pentyloxy group; an neopentyloxy group; an isopentyloxy group; an n-hexyloxy group; a 3,3-dimethylbutyloxy group; a 2-ethylbutyloxy group; an n-octyloxy group; an n-nonyloxy group; an n-decyloxy group; a benzyloxy group; a p-methylbenzyloxy group; and the like, but are not limited thereto.

In the present specification, a silyl group may be represented by a formula of —SiRaRbRc, and Ra, Rb, and Rc are the same as or different from each other, and may be each independently hydrogen; a substituted or unsubstituted alkyl group; or a substituted or unsubstituted aryl group. Specific examples of the silyl group include a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group; and the like, but are not limited thereto.

In the present specification, an aryl group is not particularly limited, but has preferably 6 to 30 carbon atoms, and more preferably 6 to 20 carbon atoms. The aryl group may be monocyclic or polycyclic. When the aryl group is a monocyclic aryl group, the number of carbon atoms thereof is not particularly limited, but is preferably 6 to 30. More specifically, the number of carbon atoms thereof is preferably 6 to 20. Specific examples of the monocyclic aryl group include a phenyl group; a biphenyl group; a terphenyl group; and the like, but are not limited thereto. When the aryl group is a polycyclic aryl group, the number of carbon atoms thereof is not particularly limited, but is preferably 10 to 30, and more specifically, preferably 10 to 20 carbon atoms. Specific examples of the polycyclic aryl group include a naphthyl group; an anthracenyl group; a phenanthryl group; a triphenyl group; a pyrenyl group; a phenalenyl group; a perylenyl group; a chrysenyl group; a fluorenyl group; and the like, but are not limited thereto.

In the present specification, a heteroaryl group includes one or more atoms other than carbon, that is, one or more heteroatoms, and specifically, the heteroatom may include one or more atoms selected from the group consisting of O, N, Se, S, and the like. The number of carbon atoms thereof is not particularly limited, but is preferably 2 to 30, and more preferably 2 to 20, and the heteroaryl group may be monocyclic or polycyclic. Examples of the heteroaryl group include a thiophene group; a furanyl group; a pyrrole group; an imidazolyl group; a thiazolyl group; an oxazolyl group; an oxadiazolyl group; a pyridyl group; a bipyridyl group; a pyrimidyl group; a triazinyl group; a triazolyl group; an acridyl group; a pyridazinyl group; a pyrazinyl group; a qinolinyl group; a quinazolinyl group; a quinoxalinyl group; a phthalazinyl group; a pyridopyrimidyl group; a pyridopyrazinyl group; a pyrazinopyrazinyl group; an isoquinolinyl group; an indolyl group; a carbazolyl group; a benzoxazolyl group; a benzimidazolyl group; a benzothiazolyl group; a benzocarbazolyl group; a benzothiophene group; a dibenzothiophene group; a benzofuranyl group; a phenanthrolinyl group; an isoxazolyl group; a thiadiazolyl group; a phenothiazinyl group; a dibenzofuranyl group; and the like, but are not limited thereto.

In the present specification, an amine group may be selected from the group consisting of —NH₂; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group; a dimethylamine group; an ethylamine group; a diethylamine group; a phenylamine group; a naphthylamine group; a biphenylamine group; an anthracenylamine group; a 9-methylanthracenylamine group; a diphenylamine group; an N-phenylnaphthylamine group; a ditolylamine group; an N-phenyltolylamine group; a triphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group; and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In an exemplary embodiment of the present specification, Formula 1 is represented by the following Formula 1-1 or 1-2.

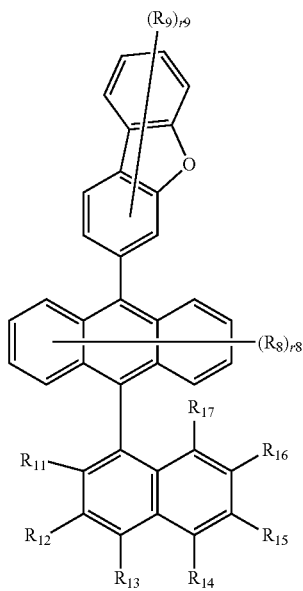

[Formula 1-1]

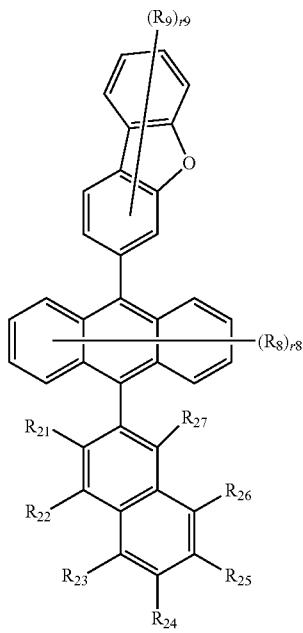

[Formula 1-2]

In Formulae 1-1 and 1-2, the definitions of R8, R9, r8, and r9 are the same as those defined for Formula 1, $R_{11}$ to $R_{17}$ and $R_{21}$ to $R_{27}$ are the same as or different from each other, and are each independently hydrogen, deuterium, or a substituted or unsubstituted aryl group.

In an exemplary embodiment of the present specification, $R_1$ to $R_7$ are the same as or different from each other, and are each independently hydrogen, deuterium, or a substituted or unsubstituted aryl group.

In an exemplary embodiment of the present specification, $R_1$ to $R_7$ are the same as or different from each other, and are each independently hydrogen, deuterium, or a substituted or unsubstituted aryl group having 6 to 30 carbon atoms.

In an exemplary embodiment of the present specification, $R_1$ to $R_7$ are the same as or different from each other, and are each independently hydrogen, deuterium, a substituted or unsubstituted monocyclic aryl group having 6 to 30 carbon atoms, or a substituted or unsubstituted polycyclic aryl group having 10 to 30 carbon atoms.

In an exemplary embodiment of the present specification, $R_1$ to $R_7$ are the same as or different from each other, and are each independently hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracene group, a substituted or unsubstituted phenanthrene group, or a substituted or unsubstituted triphenylene group.

In an exemplary embodiment of the present specification, $R_1$ to $R_7$ are the same as or different from each other, and are each independently hydrogen, deuterium, a phenyl group, a biphenyl group, a terphenyl group, a naphthyl group, an anthracene group, a phenanthrene group, or a triphenylene group.

In an exemplary embodiment of the present specification, $R_1$ to $R_7$ are the same as or different from each other, and are each independently hydrogen, deuterium, a phenyl group, a biphenyl group, or a naphthyl group. In an exemplary embodiment of the present specification, $R_1$ to $R_7$ are the same as or different from each other, and are each independently hydrogen, deuterium, or any one selected from the following (1) to (6).

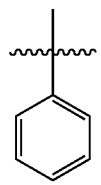

(1)

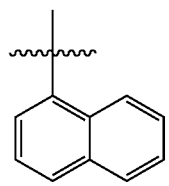

(2)

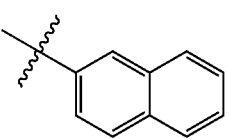

(3)

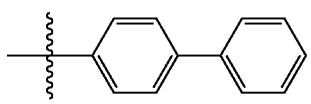

(4)

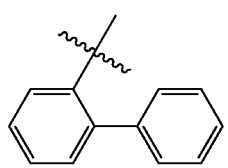

(5)

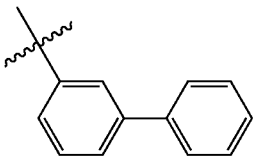

(6)

In an exemplary embodiment of the present specification, one or more of $R_1$ to $R_7$ are a substituted or unsubstituted aryl group, and the others are hydrogen or deuterium.

In the compound of Formula 1, both the HOMO and LUMO are located in anthracene. Therefore, a case where any one or more of $R_1$ to $R_7$ are an aryl group is advantageous for adjusting the film shape, the intermolecular distance or the like while not significantly impairing electromagnetic characteristics of the No. 3 dibenzofuran—anthracene—naphthalene skeleton, as compared to other substituents such as an alkyl group and a heteroaryl group.

In an exemplary embodiment of the present specification, when any one of $R_1$ to $R_7$ is a biphenyl group, at least one pair of the groups from the anthracene group of Formula 1 to the end phenyl group of the biphenyl group occupies ortho or meta position. When any one of $R_1$ to $R_7$ is a biphenyl group, in the case where the groups from the anthracene structure of Formula 1 to the end phenyl group of the biphenyl group are all in para positions, the deposition temperature excessively increases due to the increased molecular length, which causes a problem with process. In contrast, when at least one pair of the groups from the anthracene structure of Formula 1 to the end phenyl group of the biphenyl group form ortho or meta substitution, the problem with the process with respect to the para bond may be solved.

Further, when ortho or meta substitution is formed, the crystallinity of the molecule is reduced as compared to the para bond, and thus, amorphous characteristics are improved when a film is formed by depositing a compound. While a material having high crystallinity is deposited film characteristics are non-uniform during the deposition, so that the material aggregates or a trap which disturbs the movement of electric charges occurs, and these traps cause a degradation phenomenon of the material, thereby reducing the service life of a device. A compound including a biphenyl group of ortho or meta substitution may solve the aforementioned problems, and have long service life characteristics of a device.

In an exemplary embodiment of the present specification, any one of $R_1$ to $R_7$ is the following (5) or (6)

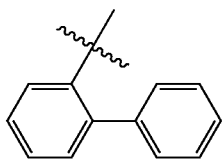

(5)

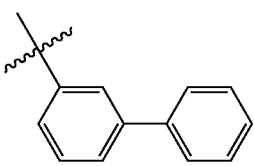

(6)

In an exemplary embodiment of the present specification, when any one of $R_1$ to $R_3$ is a biphenyl group, at least one pair of the groups from the anthracene structure of Formula 1 to the end phenyl group of the biphenyl group forms ortho or meta substitution.

In an exemplary embodiment of the present specification, when any one of $R_4$ to $R_7$ is a biphenyl group, at least one pair of the groups from the anthracene structure of Formula 1 to the end phenyl group of the biphenyl group forms ortho or meta substitution.

In an exemplary embodiment of the present specification, when any one of $R_{11}$ to $R_{13}$ is a biphenyl group, at least one pair of the groups from the anthracene structure of Formula 1-1 to the end phenyl group of the biphenyl group forms ortho or meta substitution.

In an exemplary embodiment of the present specification, Formula 1 is represented by the following Formula 2-1 or 2-2.

[Formula 2-1]

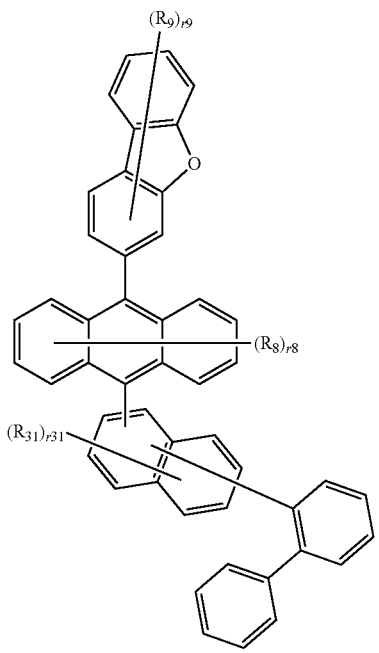

[Formula 2-2]

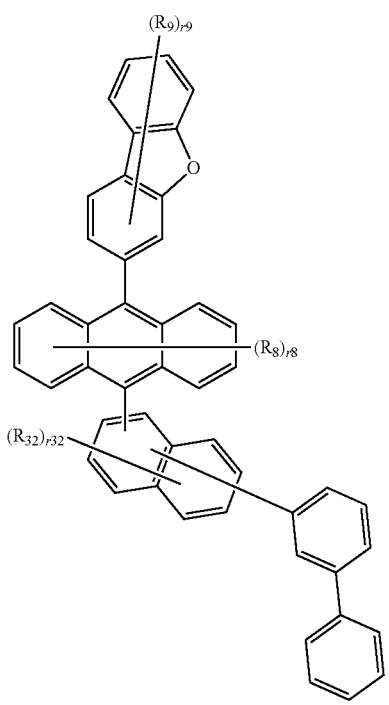

In Formulae 2-1 and 2-2, $R_8$, $R_9$, r8, and r9 are the same as those defined for Formula 1, $R_{31}$ and $R_{32}$ are the same as or different from each other, and are each independently hydrogen, deuterium, or a substituted or unsubstituted aryl group, and r31 and r32 are each an integer from 0 to 6, and when r31 is 2 or higher, $R_{31}$'s are the same as or different from each other, and when r32 is 2 or higher, $R_{32}$'s are the same as or different from each other.

In an exemplary embodiment of the present specification, $R_{31}$ and $R_{32}$ are the same as or different from each other, and are each independently hydrogen or deuterium.

In an exemplary embodiment of the present specification, $R_{31}$ and $R_{32}$ are hydrogen.

In an exemplary embodiment of the present specification, $R_{31}$ and $R_{32}$ are deuterium.

In an exemplary embodiment of the present specification, $R_{11}$ to $R_{17}$ are the same as or different from each other, and are each independently hydrogen, deuterium, or a substituted or unsubstituted aryl group having 6 to 30 carbon atoms.

In an exemplary embodiment of the present specification, $R_{11}$ to $R_{17}$ are the same as or different from each other, and are each independently hydrogen, deuterium, a substituted or unsubstituted monocyclic aryl group having 6 to 30 carbon atoms, or a substituted or unsubstituted polycyclic aryl group having 10 to 30 carbon atoms.

In an exemplary embodiment of the present specification, one or more of $R_{11}$ to $R_{17}$ are a substituted or unsubstituted aryl group having 6 to 30 carbon atoms, and the others are hydrogen or deuterium.

In an exemplary embodiment of the present specification, one of $R_{11}$ to $R_{17}$ is a substituted or unsubstituted aryl group having 6 to 30 carbon atoms, and the others are hydrogen or deuterium.

In an exemplary embodiment of the present specification, two of $R_{11}$ to $R_{17}$ are a substituted or unsubstituted aryl group having 6 to 30 carbon atoms, and the others are hydrogen or deuterium.

In an exemplary embodiment of the present specification, $R_{11}$ to $R_{17}$ are the same as or different from each other, and are each independently hydrogen, a phenyl group, a biphenyl group, or a naphthyl group.

In an exemplary embodiment of the present specification, $R_{11}$ is a substituted or unsubstituted monocyclic aryl group having 6 to 30 carbon atoms; or a substituted or unsubstituted polycyclic aryl group having 10 to 30 carbon atoms.

In an exemplary embodiment of the present specification, $R_{12}$ is a substituted or unsubstituted monocyclic aryl group having 10 to 30 carbon atoms, or a substituted or unsubstituted polycyclic aryl group having 10 to 30 carbon atoms.

In an exemplary embodiment of the present specification, $R_{13}$ is a substituted or unsubstituted monocyclic aryl group having 10 to 30 carbon atoms, or a substituted or unsubstituted polycyclic aryl group having 10 to 30 carbon atoms.

In an exemplary embodiment of the present specification, $R_{14}$ is a substituted or unsubstituted monocyclic aryl group having 10 to 30 carbon atoms, or a substituted or unsubstituted polycyclic aryl group having 10 to 30 carbon atoms.

In an exemplary embodiment of the present specification, $R_{15}$ is a substituted or unsubstituted monocyclic aryl group having 10 to 30 carbon atoms, or a substituted or unsubstituted polycyclic aryl group having 10 to 30 carbon atoms.

In an exemplary embodiment of the present specification, $R_{16}$ is a substituted or unsubstituted monocyclic aryl group having 6 to 30 carbon atoms; or a substituted or unsubstituted polycyclic aryl group having 10 to 30 carbon atoms.

In an exemplary embodiment of the present specification, $R_{17}$ is a substituted or unsubstituted monocyclic aryl group having 6 to 30 carbon atoms, or a substituted or unsubstituted polycyclic aryl group having 10 to 30 carbon atoms.

In an exemplary embodiment of the present specification, $R_{21}$ to $R_{27}$ are the same as or different from each other, and are each independently hydrogen or a substituted or unsubstituted aryl group having 6 to 30 carbon atoms.

In an exemplary embodiment of the present specification, $R_{21}$ to $R_{27}$ are the same as or different from each other, and are each independently hydrogen, a substituted or unsubstituted monocyclic aryl group having 6 to 30 carbon atoms, or a substituted or unsubstituted polycyclic aryl group having 10 to 30 carbon atoms.

In an exemplary embodiment of the present specification, one or more of $R_{21}$ to $R_{27}$ are a substituted or unsubstituted aryl group having 6 to 30 carbon atoms, and the others are hydrogen or deuterium.

In an exemplary embodiment of the present specification, one of $R_{21}$ to $R_{27}$ is a substituted or unsubstituted aryl group having 6 to 30 carbon atoms, and the others are hydrogen or deuterium.

In an exemplary embodiment of the present specification, two of $R_{21}$ to $R_{27}$ are a substituted or unsubstituted aryl group having 6 to 30 carbon atoms, and the others are hydrogen or deuterium.

In an exemplary embodiment of the present specification, $R_{21}$ is a substituted or unsubstituted monocyclic aryl group having 6 to 30 carbon atoms, or a substituted or unsubstituted polycyclic aryl group having 10 to 30 carbon atoms.

In an exemplary embodiment of the present specification, $R_{22}$ is a substituted or unsubstituted monocyclic aryl group having 6 to 30 carbon atoms, or a substituted or unsubstituted polycyclic aryl group having 10 to 30 carbon atoms.

In an exemplary embodiment of the present specification, $R_{23}$ is a substituted or unsubstituted monocyclic aryl group having 6 to 30 carbon atoms, or a substituted or unsubstituted polycyclic aryl group having 10 to 30 carbon atoms.

In an exemplary embodiment of the present specification, $R_{24}$ is a substituted or unsubstituted monocyclic aryl group having 10 to 30 carbon atoms, or a substituted or unsubstituted polycyclic aryl group having 10 to 30 carbon atoms.

In an exemplary embodiment of the present specification, $R_{25}$ is a substituted or unsubstituted monocyclic aryl group having 6 to 30 carbon atoms, or a substituted or unsubstituted polycyclic aryl group having 10 to 30 carbon atoms.

In an exemplary embodiment of the present specification, $R_{26}$ is a substituted or unsubstituted monocyclic aryl group having 6 to 30 carbon atoms, or a substituted or unsubstituted polycyclic aryl group having 10 to 30 carbon atoms.

In an exemplary embodiment of the present specification, $R_{27}$ is a substituted or unsubstituted monocyclic aryl group having 6 to 30 carbon atoms, or a substituted or unsubstituted polycyclic aryl group having 10 to 30 carbon atoms.

In an exemplary embodiment of the present specification, two or more of $R_1$ to $R_7$ are a substituted or unsubstituted aryl group.

The case where two or more of $R_1$ to $R_7$ are an aryl group has long service life characteristics because the molecular weight is high, the glass transition temperature is increased, and thus thermal stability in a film is enhanced as compared to the case where only one of $R_1$ to $R_7$ is an aryl group.

In an exemplary embodiment of the present specification, two or more of $R_1$ to $R_7$ are any one selected from the following (1) to (6).

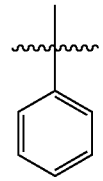

(1)

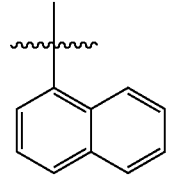

(2)

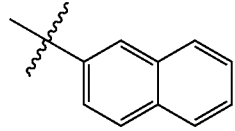

(3)

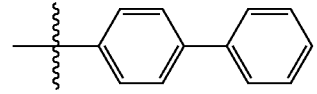

(4)

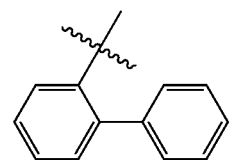

(5)

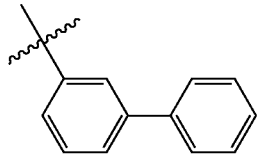

(6)

In an exemplary embodiment of the present specification, two or more of $R_1$ to $R_7$ are a phenyl group. In an exemplary embodiment of the present specification, two or more of $R_1$ to $R_7$ are a biphenyl group.

In an exemplary embodiment of the present specification, two or more of $R_1$ to $R_7$ are a naphthyl group.

In an exemplary embodiment of the present specification, two of $R_1$ to $R_7$ are any one selected from the following (1) to (6).

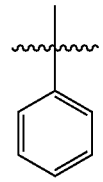

(1)

-continued (2)

(3)

(4)

(5)

(6)

In an exemplary embodiment of the present specification, $R_{11}$ and $R_{12}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{12}$ and $R_{13}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{13}$ and $R_{14}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{14}$ and $R_{15}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{15}$ and $R_{16}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{16}$ and $R_{17}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{11}$ and $R_{13}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{12}$ and $R_{14}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{13}$ and $R_{15}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{14}$ and $R_{16}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{15}$ and $R_{17}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{11}$ and $R_{14}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{12}$ and $R_{15}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{13}$ and $R_{16}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{14}$ and $R_{17}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{11}$ and $R_{15}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{12}$ and $R_{16}$ are the same as or different from each other, and are each independently a substituted or unsubstituted mono- In an exemplary embodiment of the present specification, $R_{13}$ and $R_{17}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, two of $R_{11}$ to $R_{17}$ are the same as or different from each other, and are each independently a substituted or unsubstituted monocyclic aryl group having 6 to 30 carbon atoms or a substituted or unsubstituted polycyclic aryl group having 10 to 30 carbon atoms, and the others are hydrogen.

In an exemplary embodiment of the present specification, $R_{21}$ and $R_{22}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{22}$ and $R_{23}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{23}$ and $R_{24}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{24}$ and $R_{25}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{25}$ and $R_{26}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{26}$ and $R_{27}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{21}$ and $R_{23}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{22}$ and $R_{24}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{23}$ and $R_{25}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{24}$ and $R_{26}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{25}$ and $R_{27}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{21}$ and $R_{24}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{22}$ and $R_{25}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{23}$ and $R_{26}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{24}$ and $R_{27}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{21}$ and $R_{25}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{22}$ and $R_{26}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{23}$ and $R_{27}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{21}$ and $R_{25}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{22}$ and $R_{26}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, $R_{23}$ and $R_{27}$ are the same as or different from each other, and are each independently a substituted or unsubstituted monocyclic aryl group having 6 to 30 carbon atoms or a substituted or unsubstituted polycyclic aryl group having 10 to 30 carbon atoms.

In an exemplary embodiment of the present specification, when the other substituents are all hydrogen except for any one substituent of $R_{12}$, $R_{13}$, $R_{14}$, and $R_{15}$, the substituent which is not hydrogen among $R_{12}$, $R_{13}$, $R_{14}$, and $R_{15}$ is a biphenyl group or a naphthyl group.

In an exemplary embodiment of the present specification, the compound represented by Formula 1 is any one selected from the following compounds.

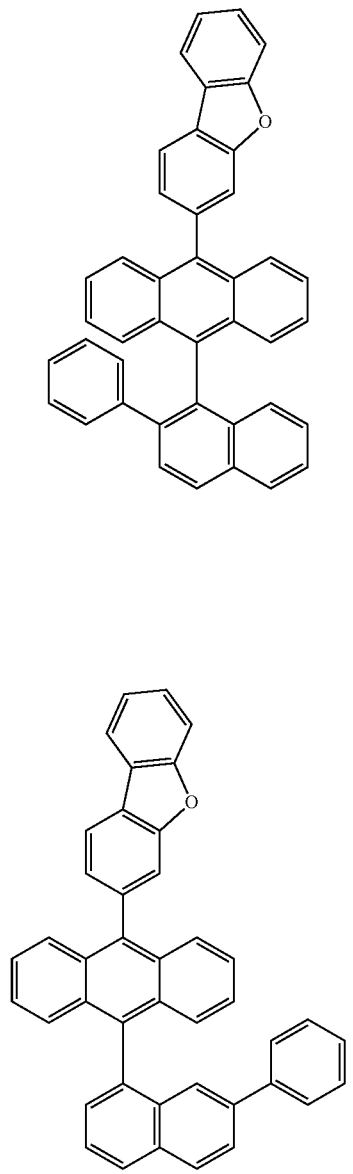

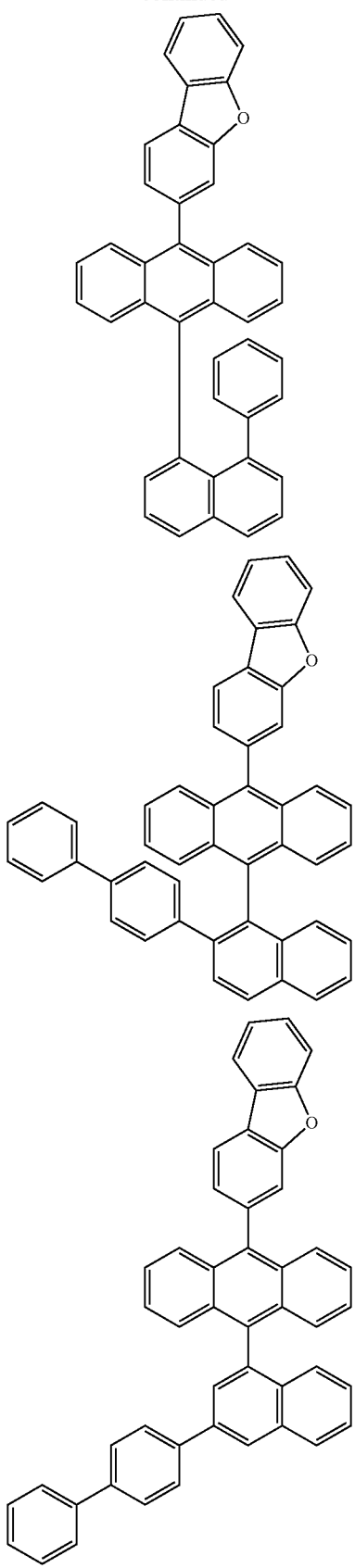

-continued
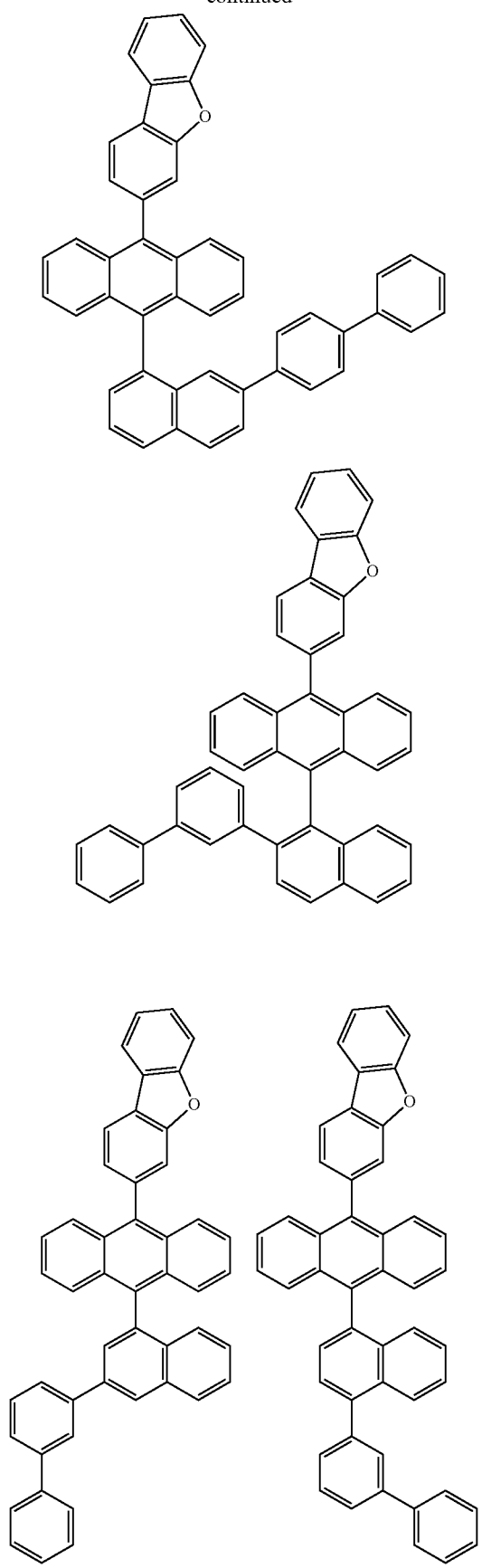
-continued
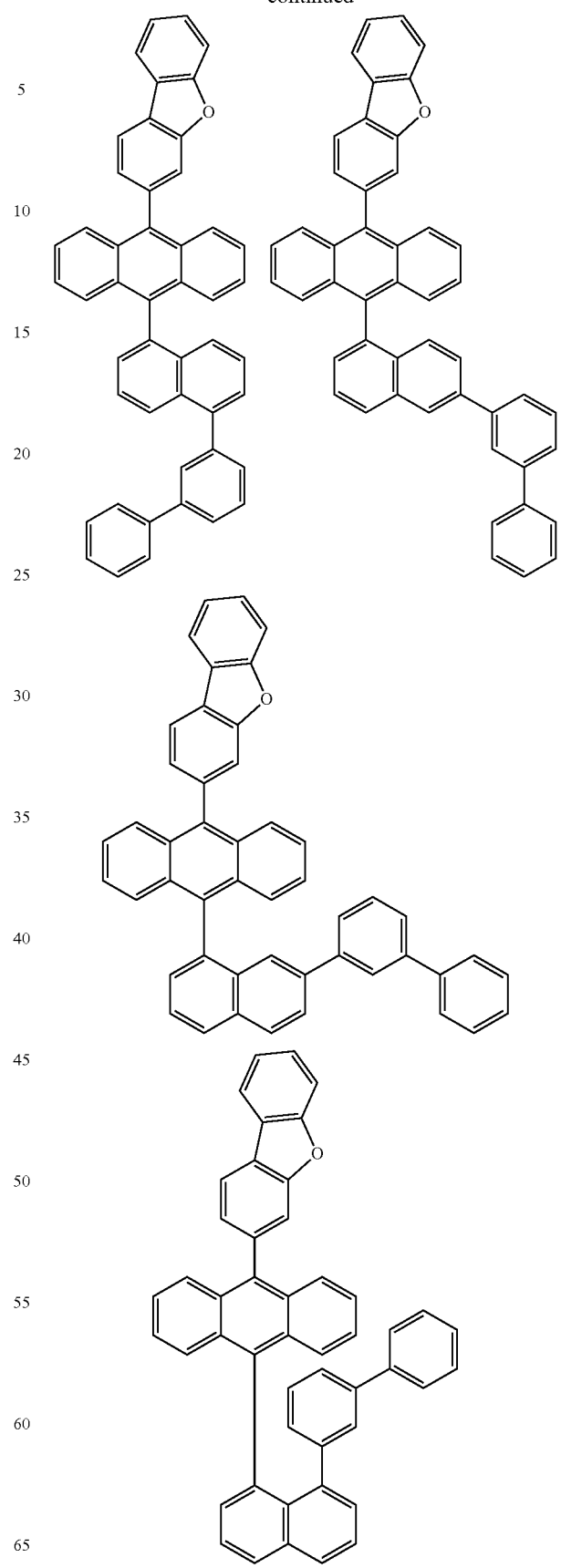

-continued
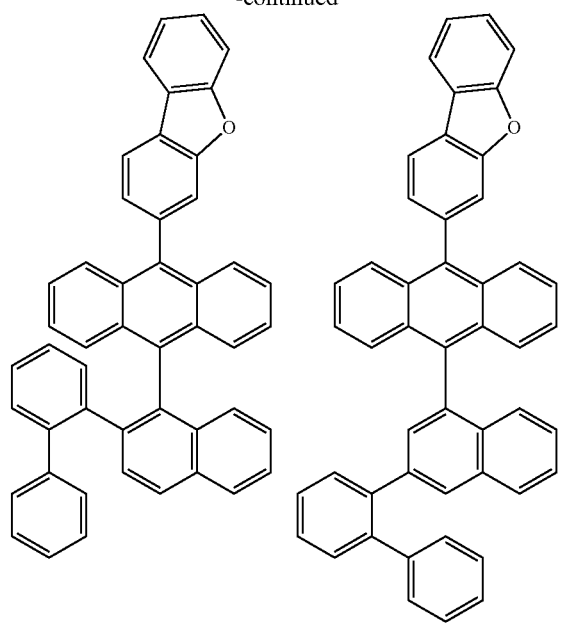
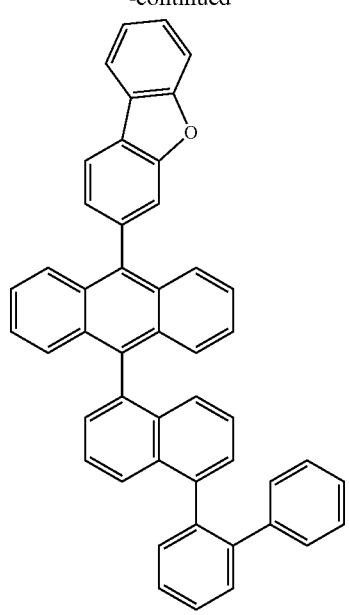
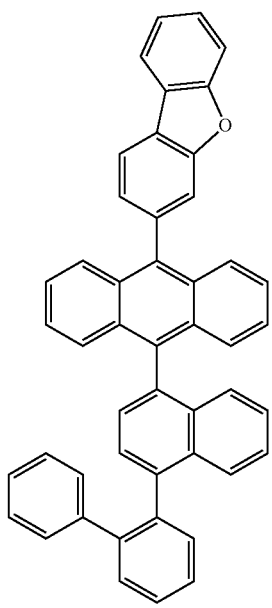
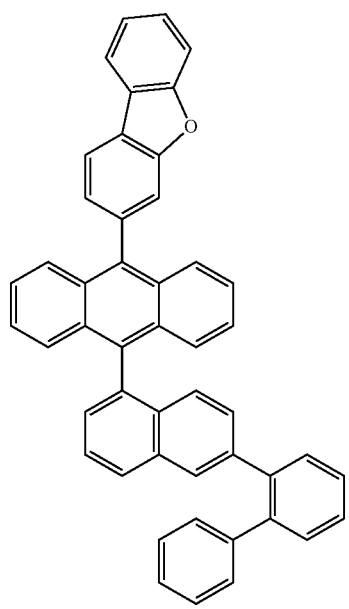

25
-continued
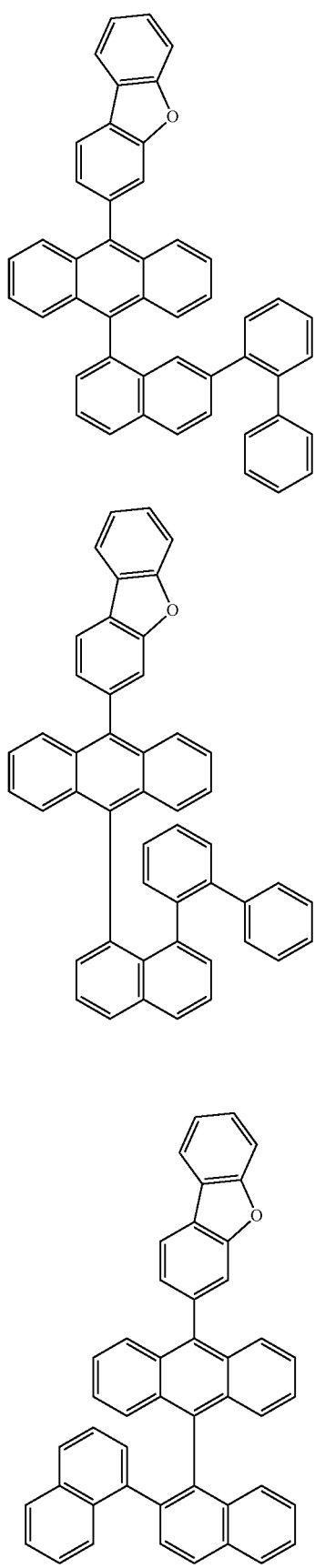
26
-continued
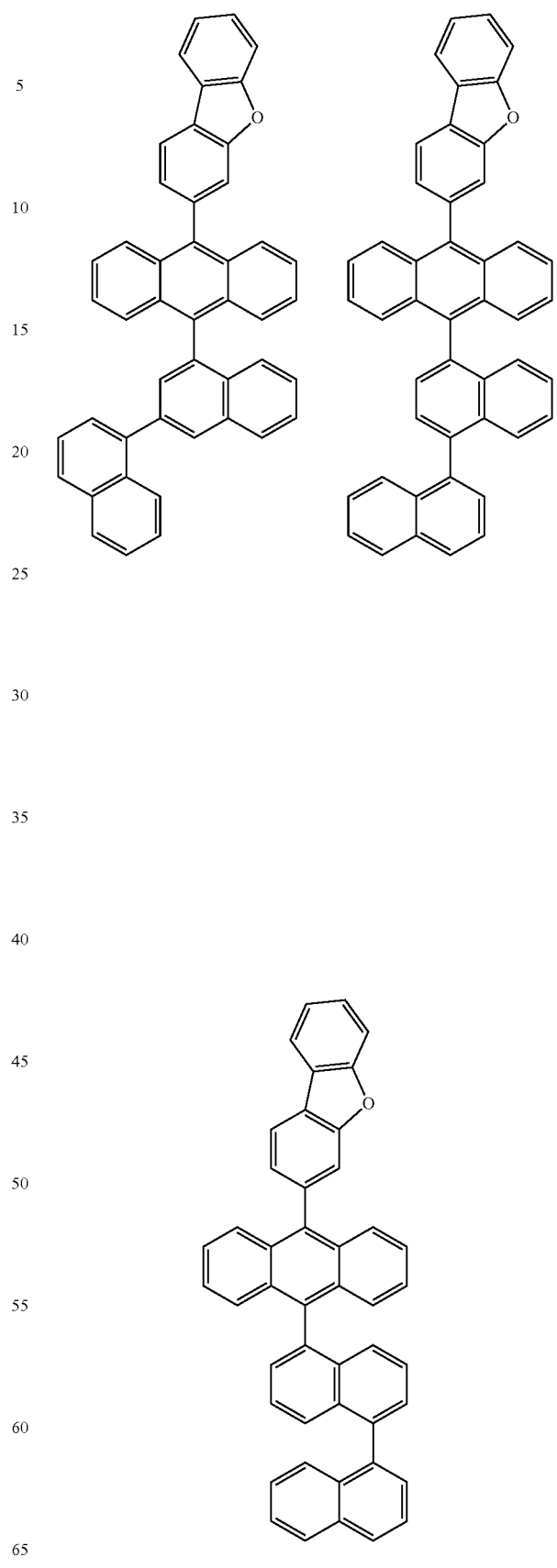

-continued
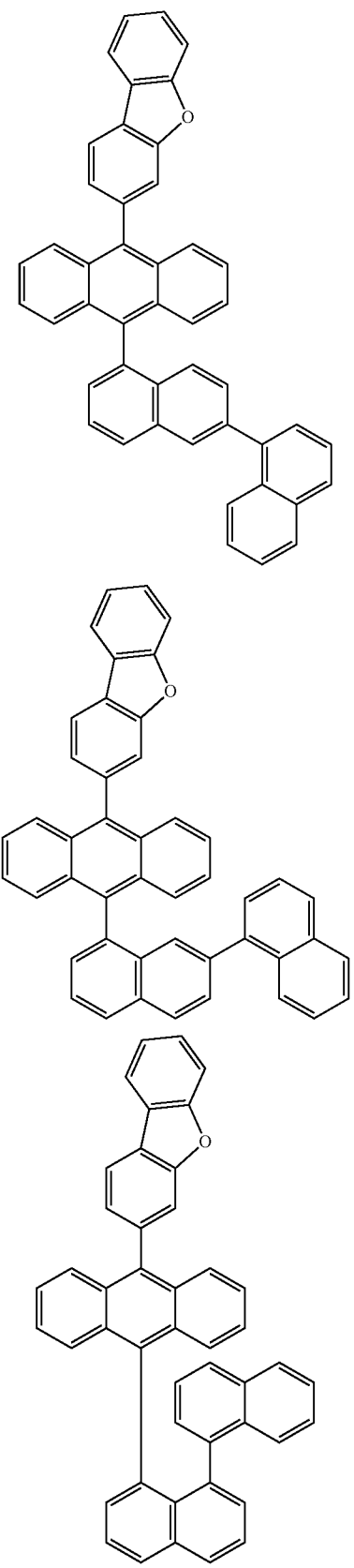
-continued
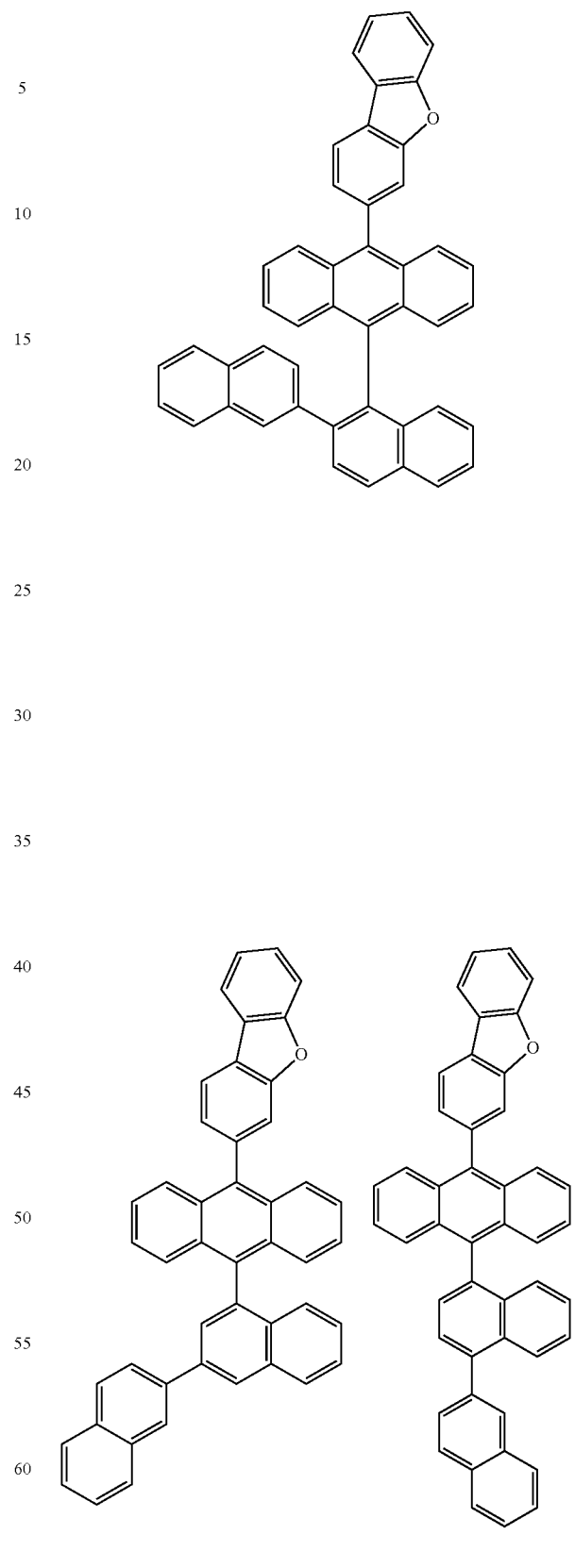

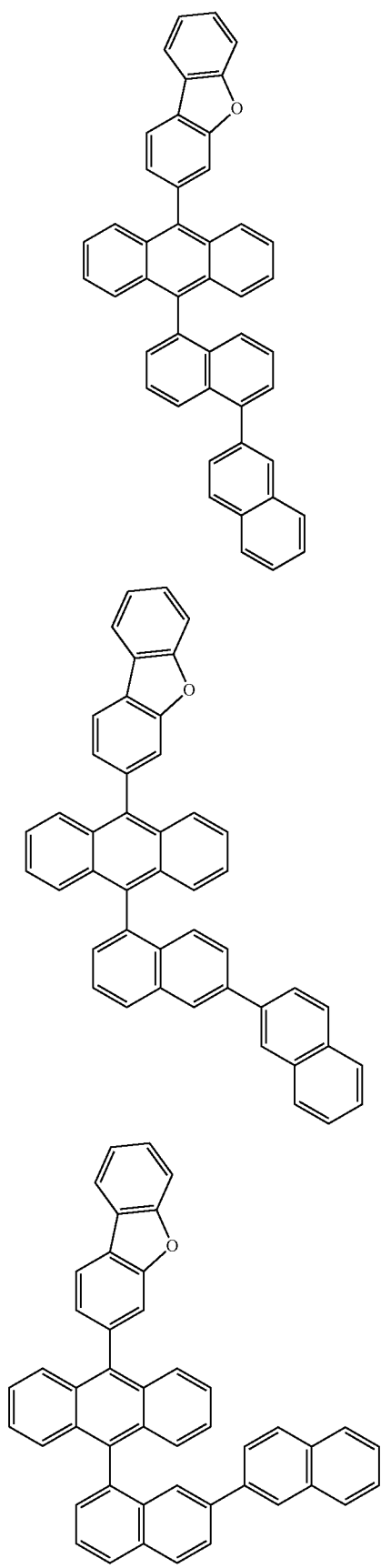
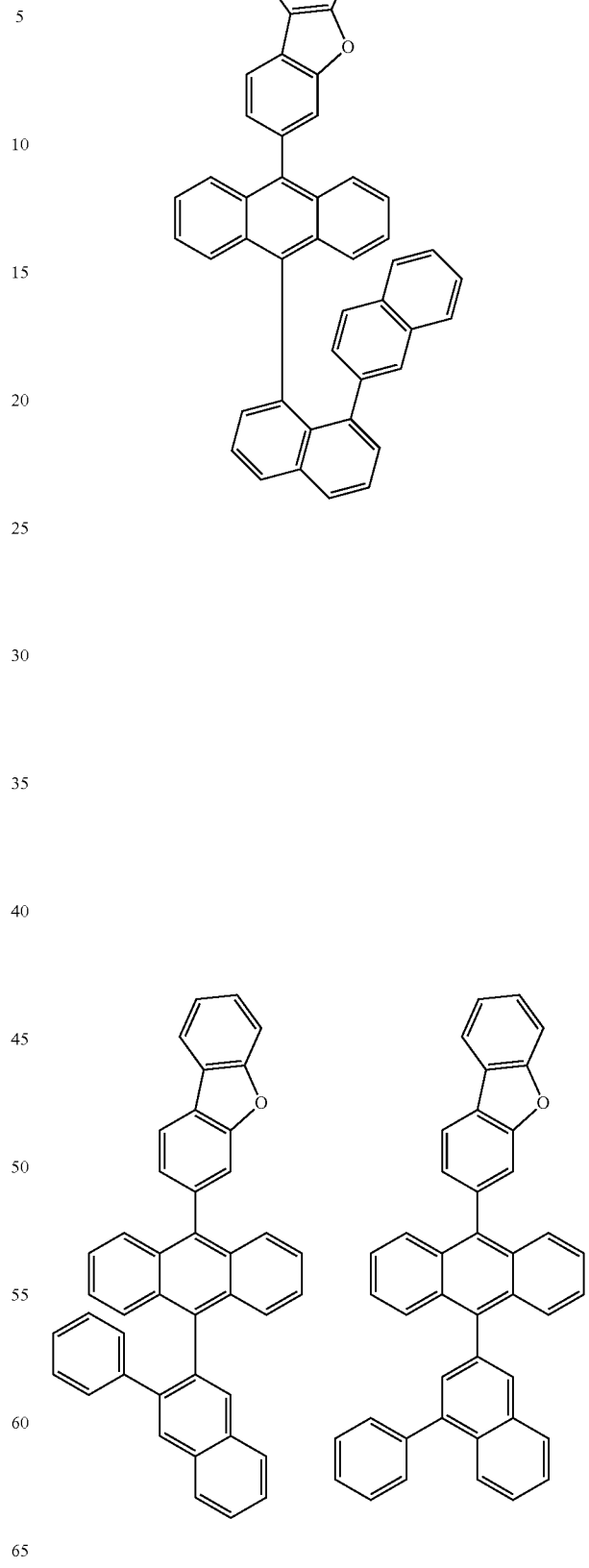

31
-continued
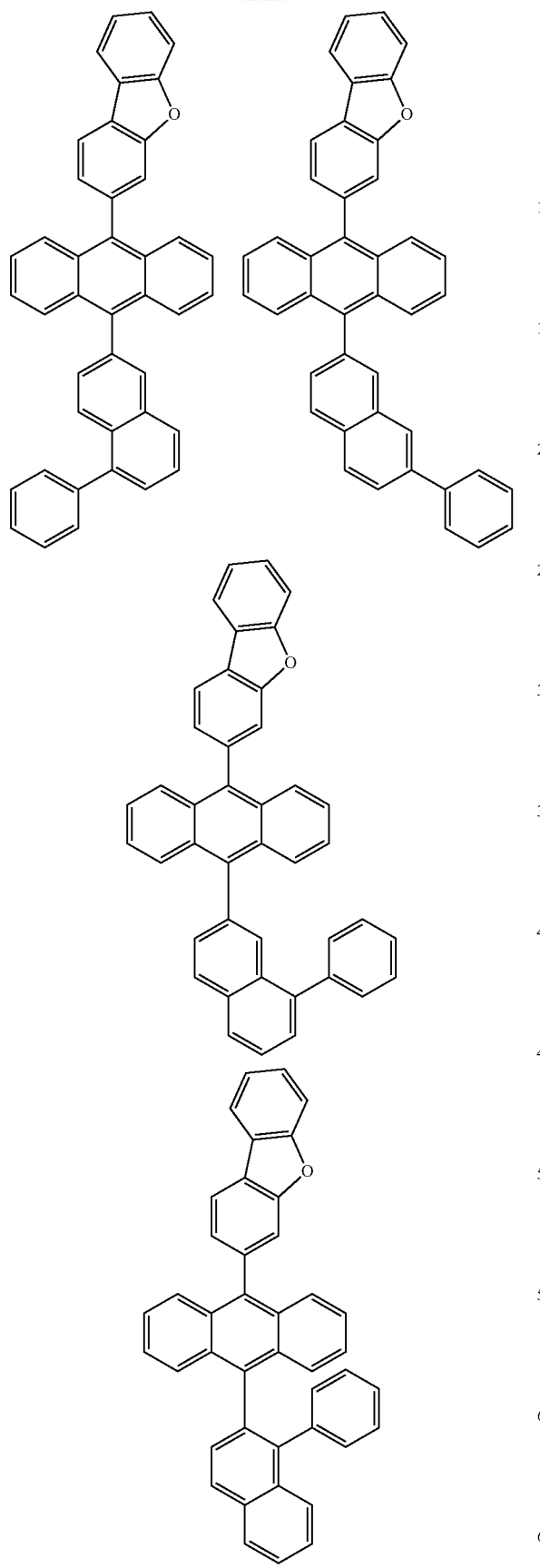
32
-continued

33
-continued
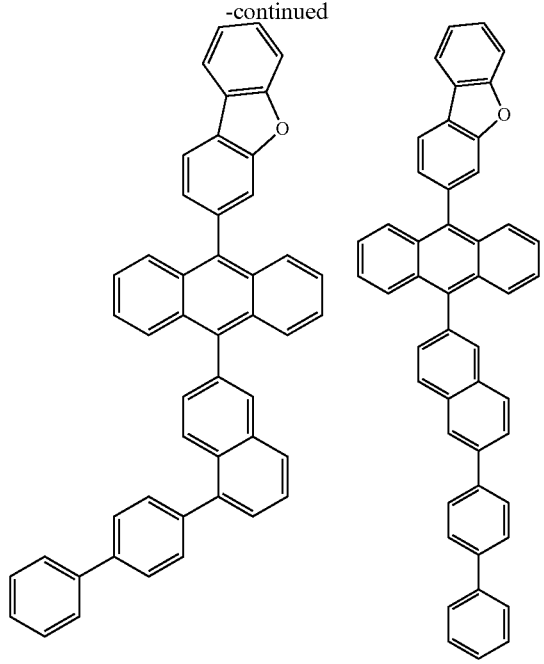
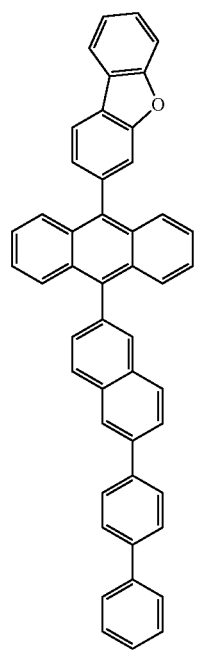
34
-continued
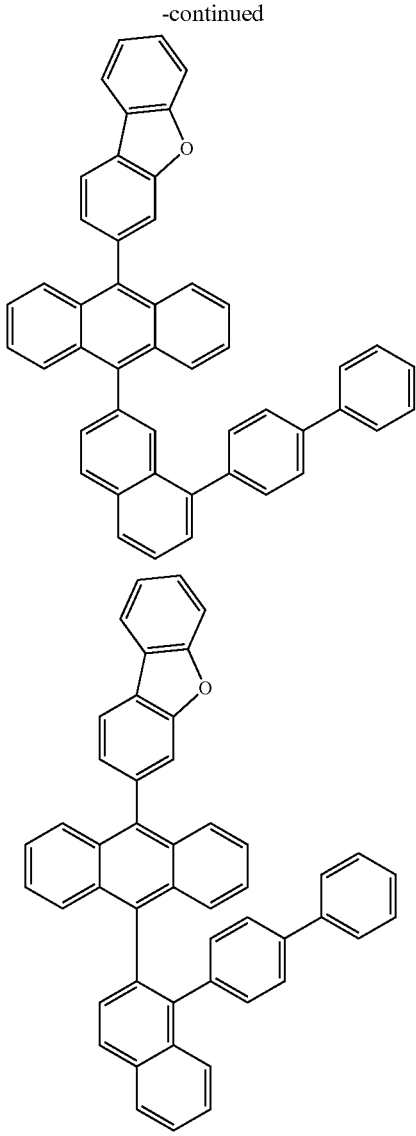
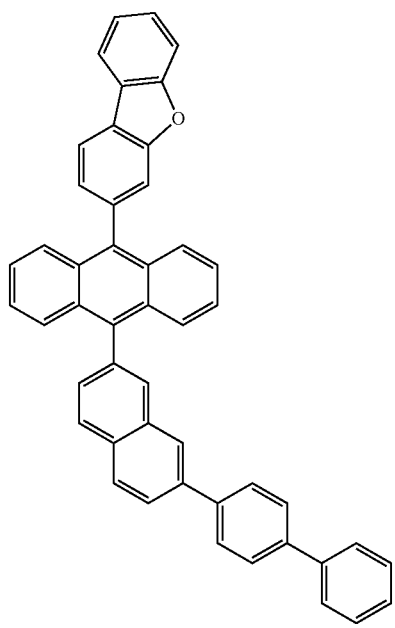

35
-continued
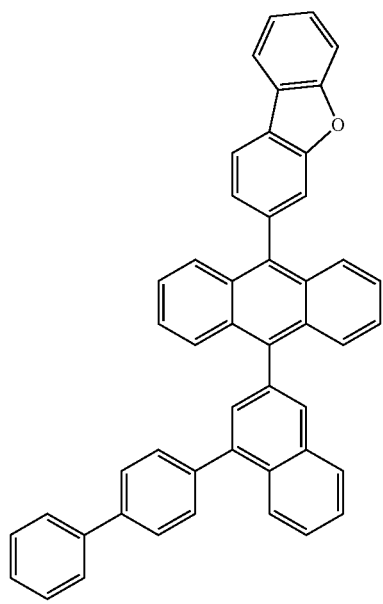
36
-continued
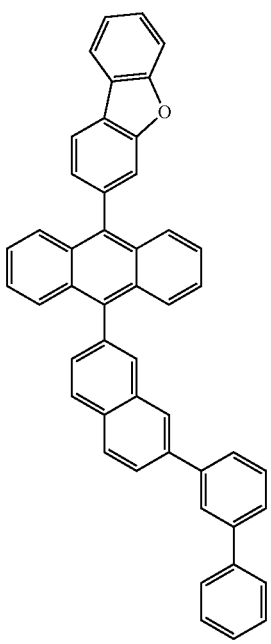
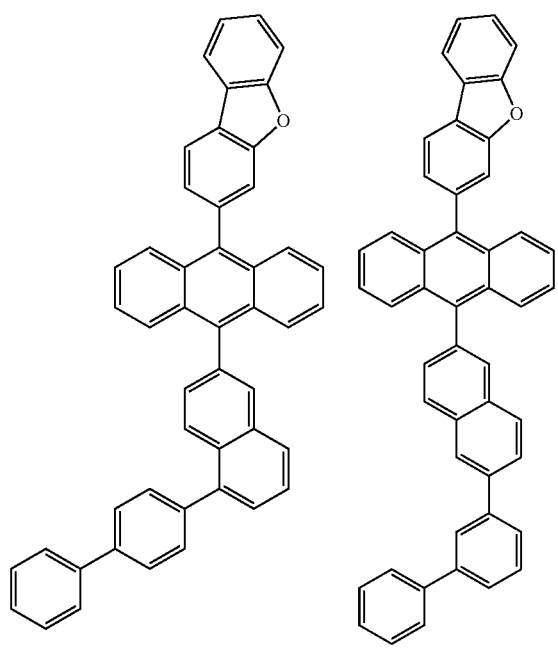
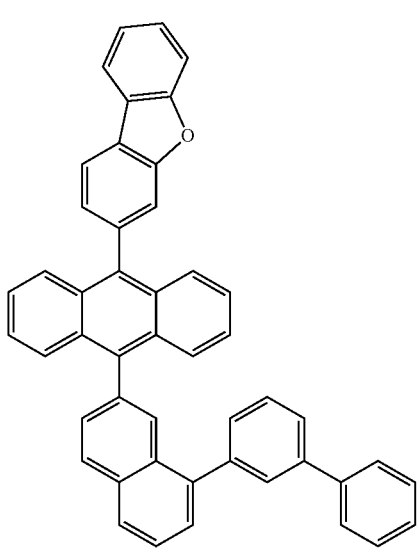

37
-continued
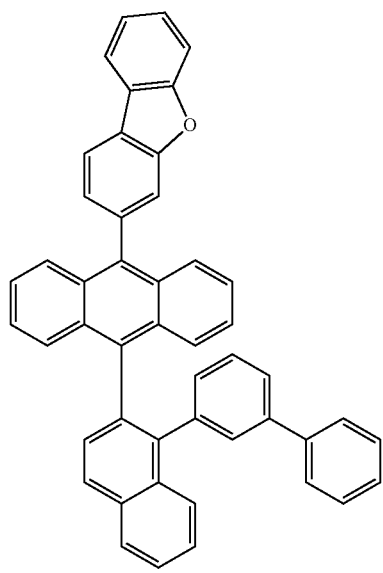
38
-continued
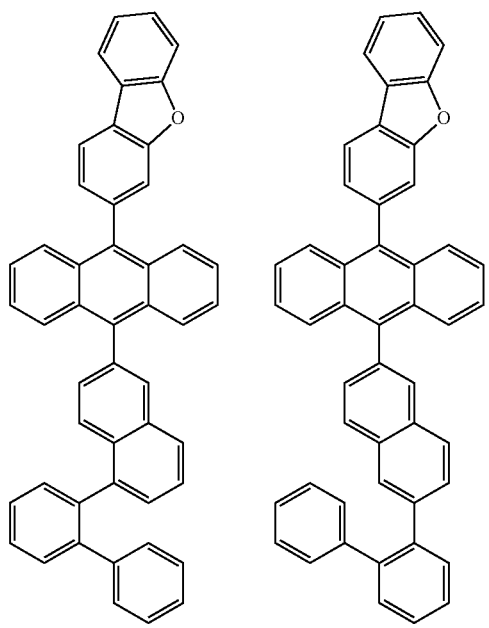
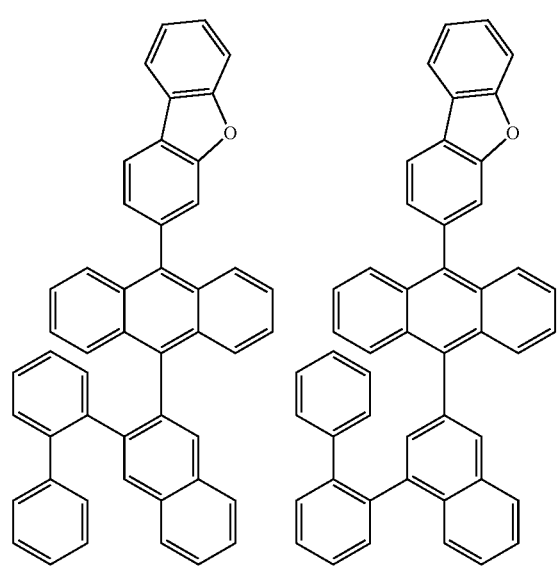
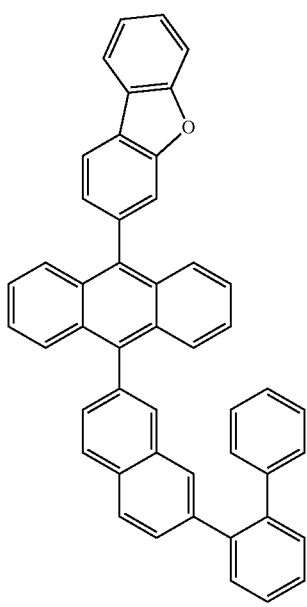

39
-continued
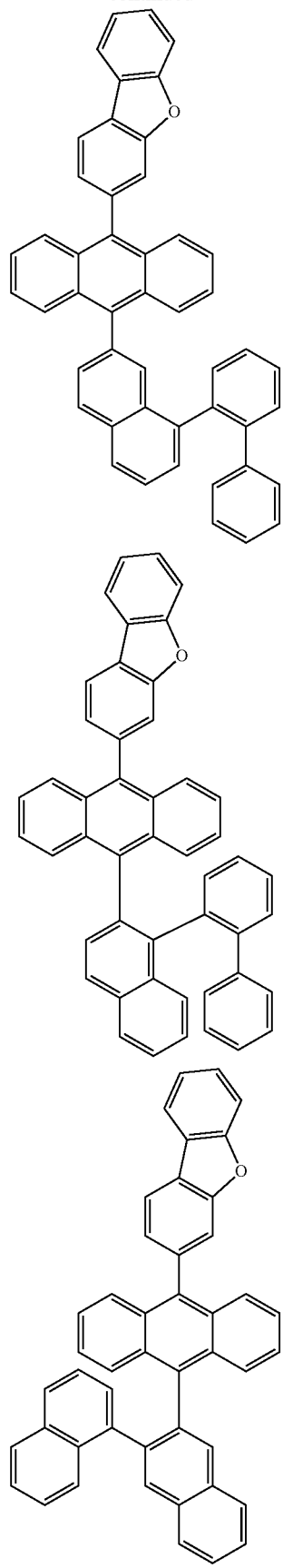
40
-continued
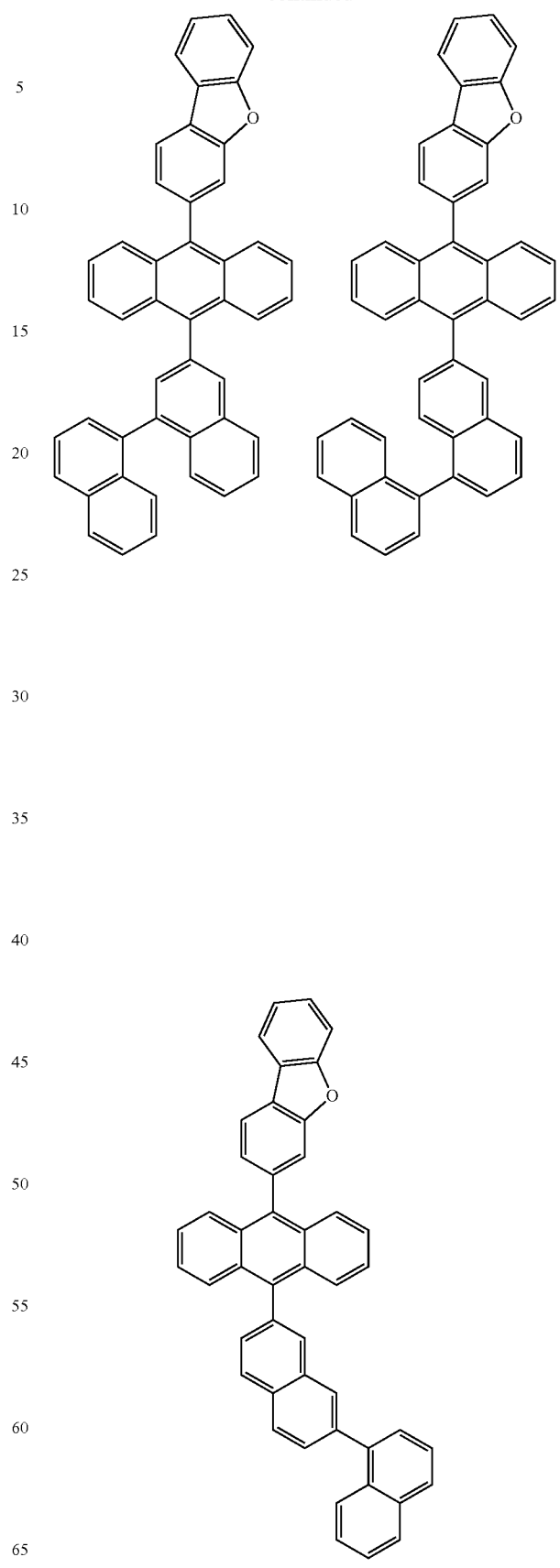

41
-continued
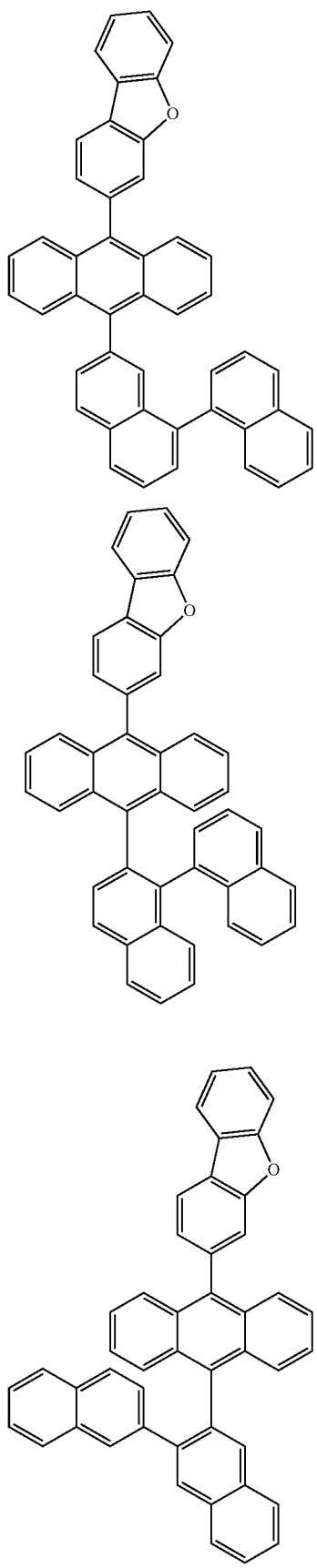
42
-continued

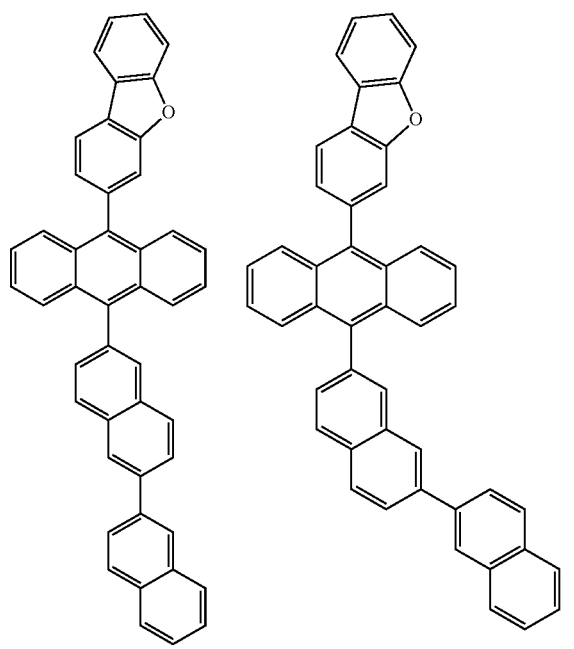
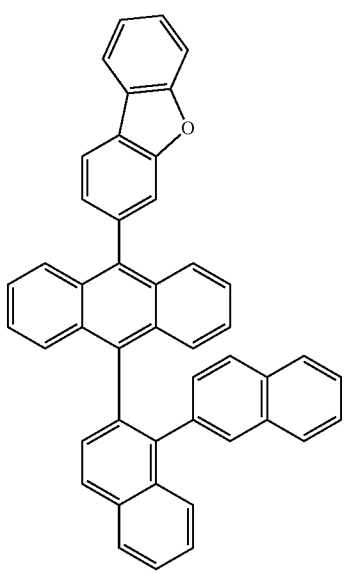
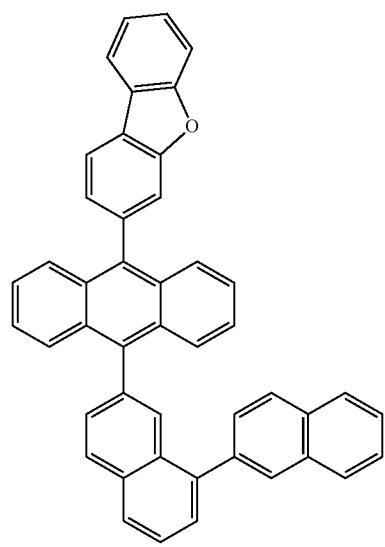
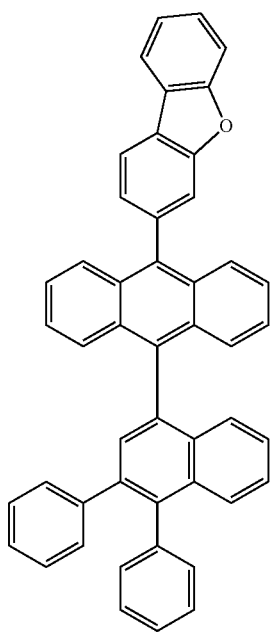

45
-continued
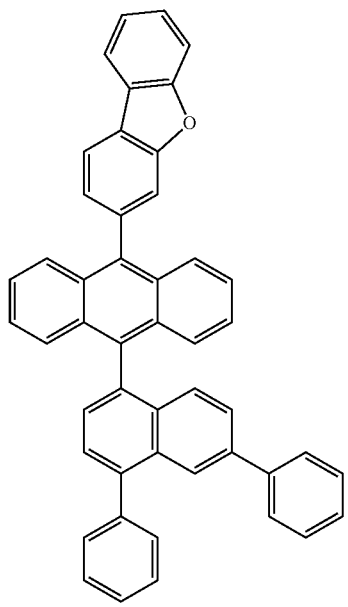
46
-continued
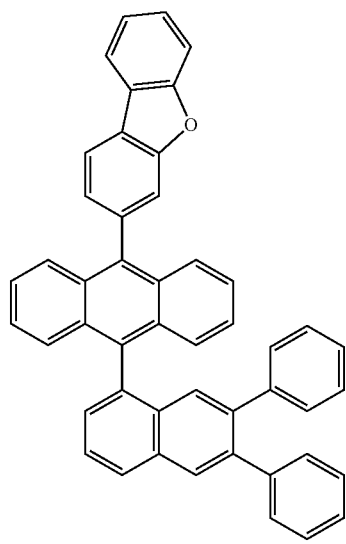
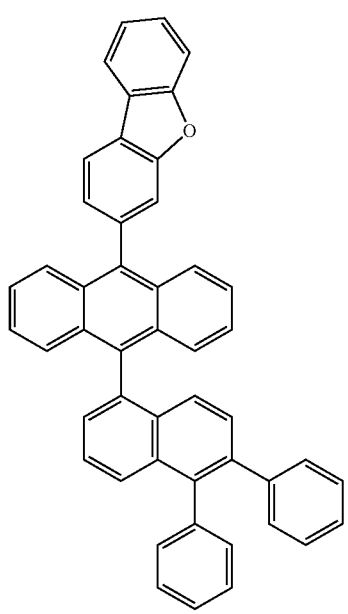
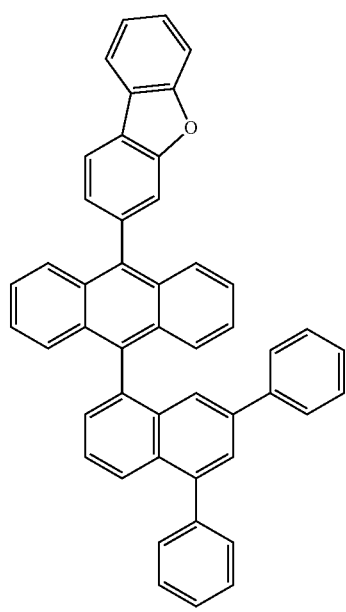

47
-continued
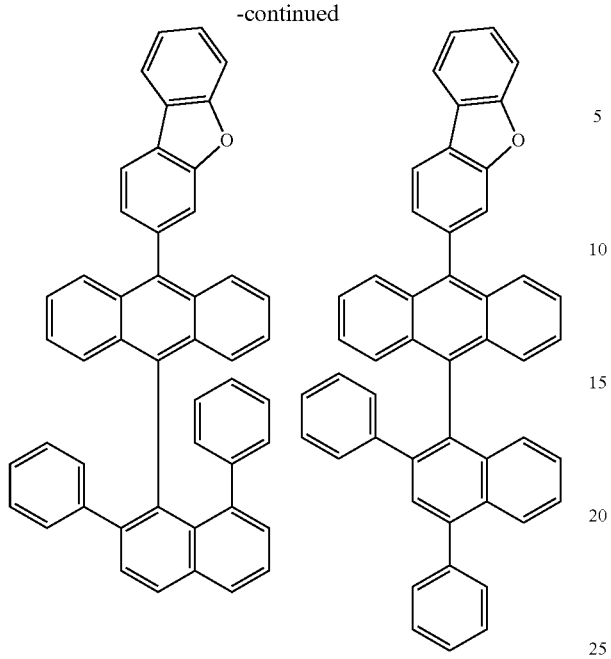
48
-continued
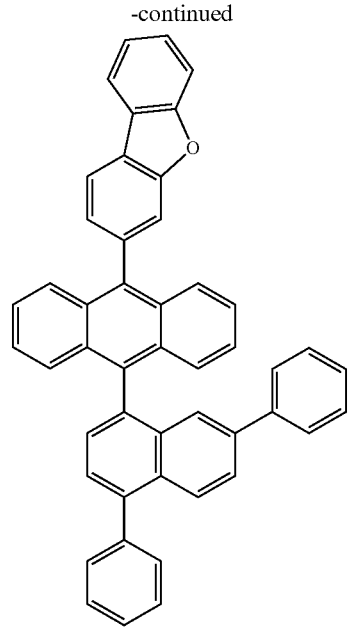
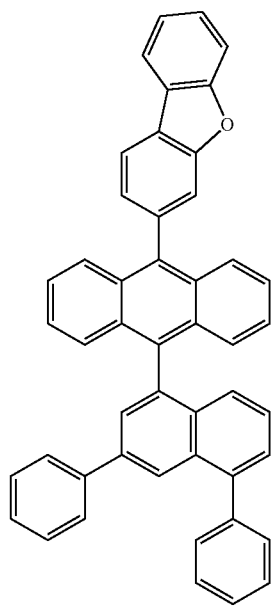
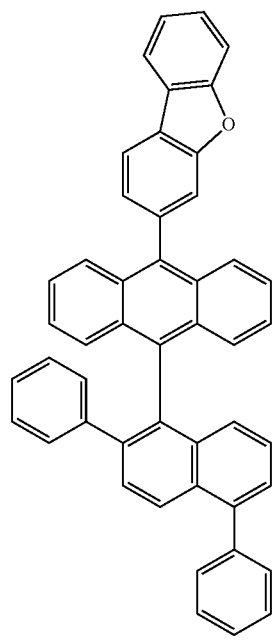

-continued
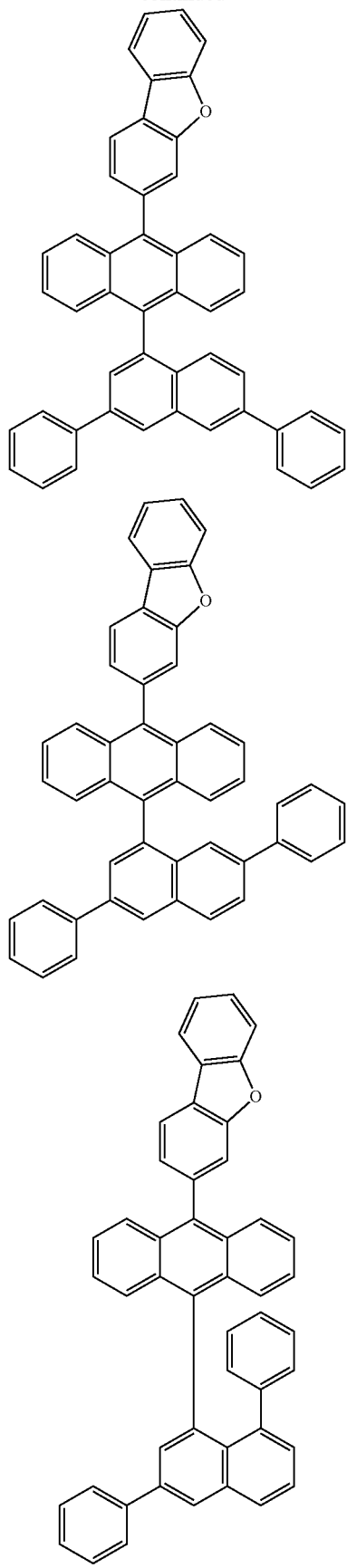
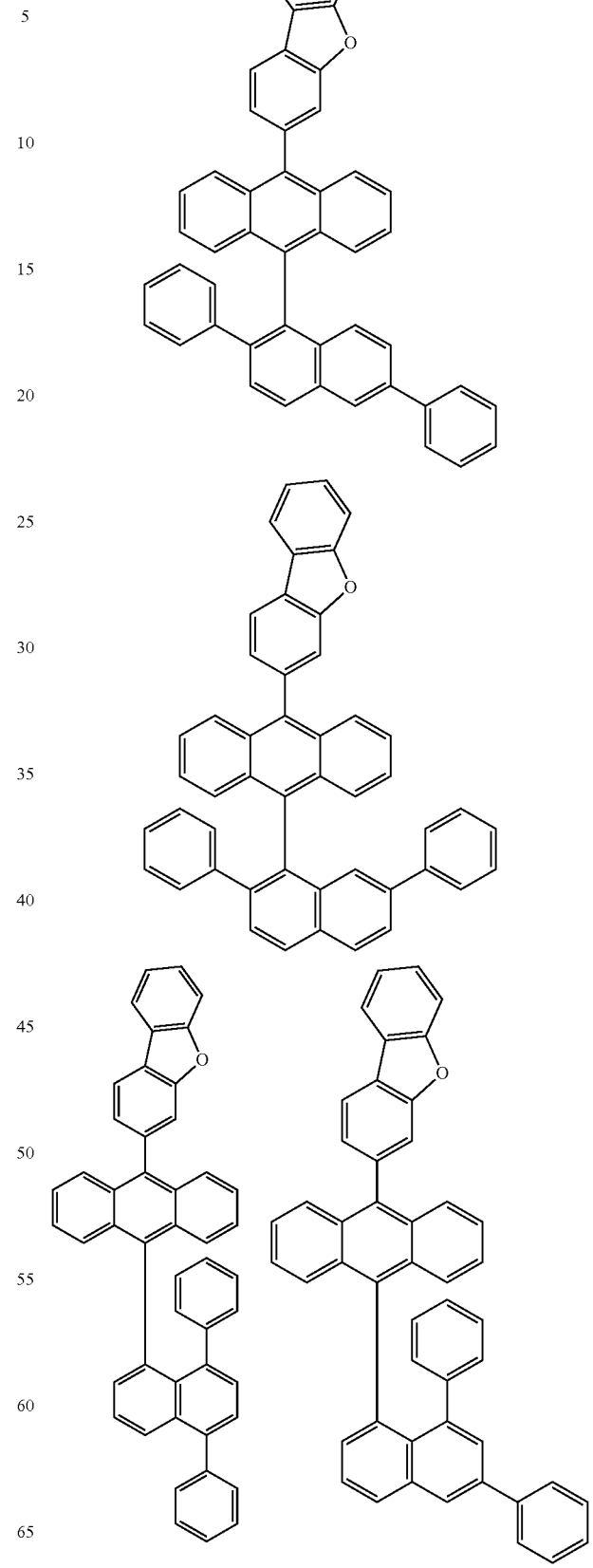

-continued
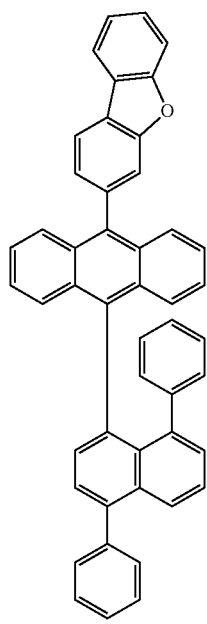
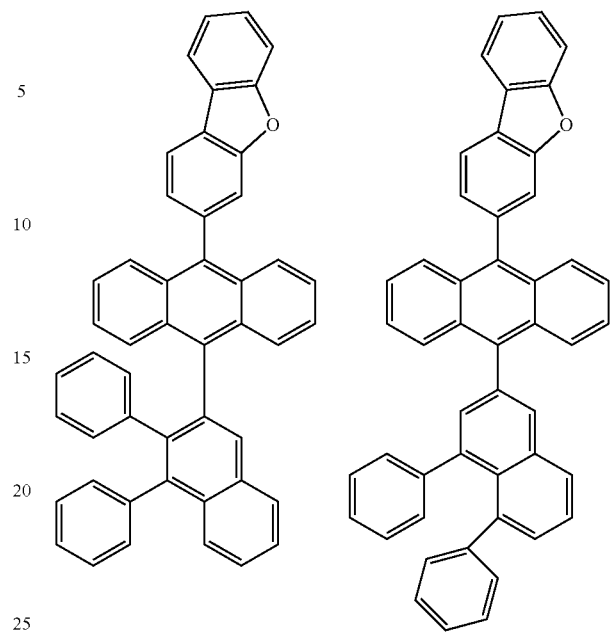
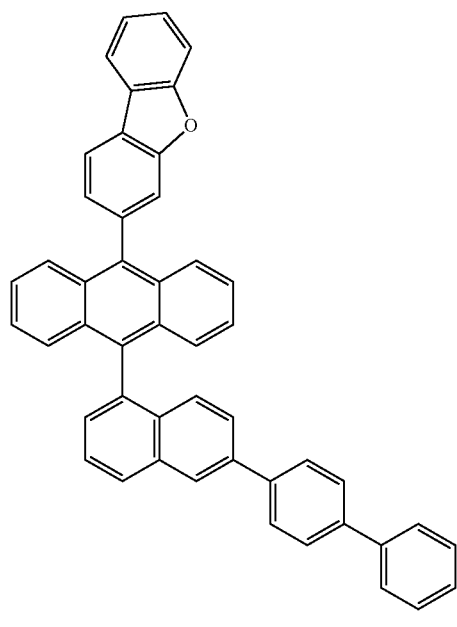
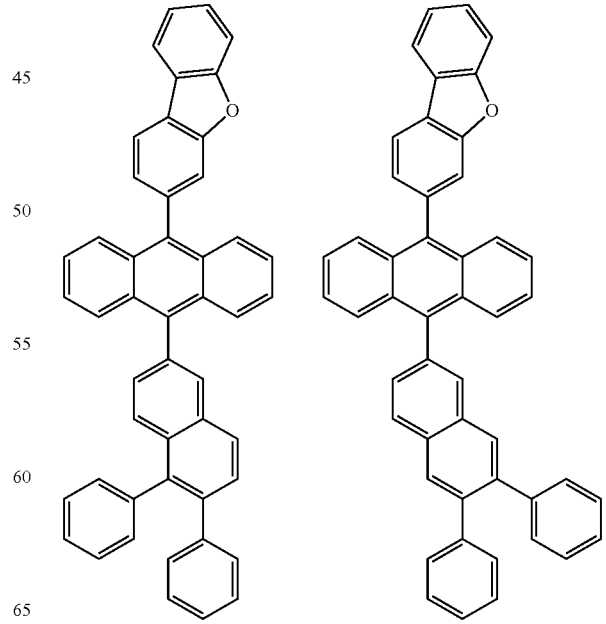

53
-continued
54
-continued
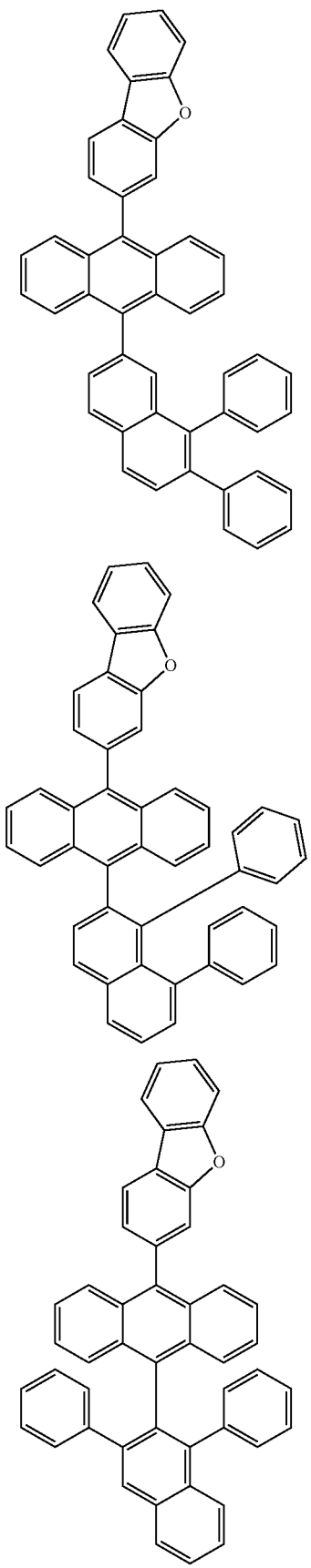
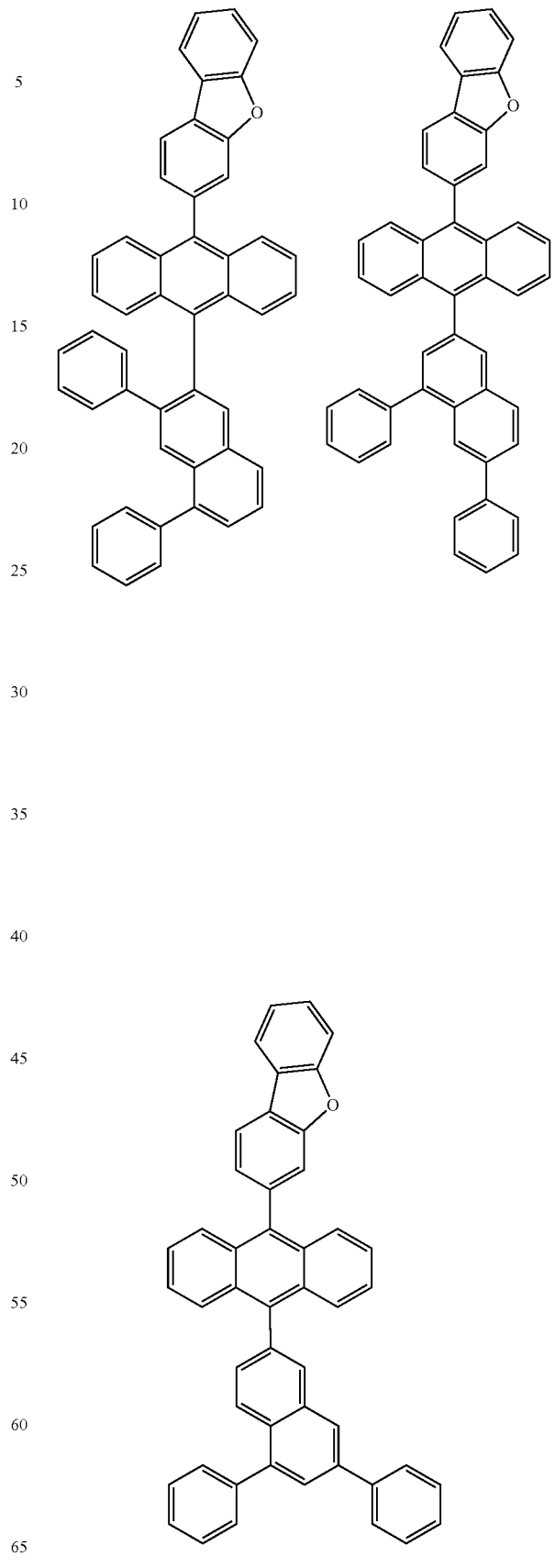

-continued
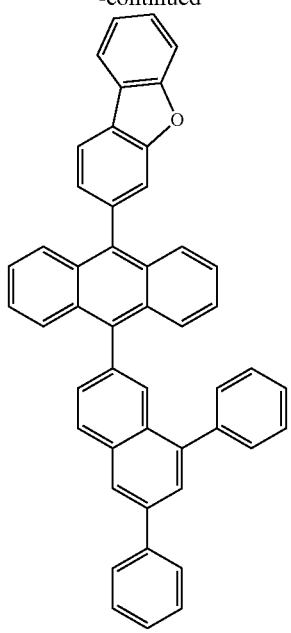
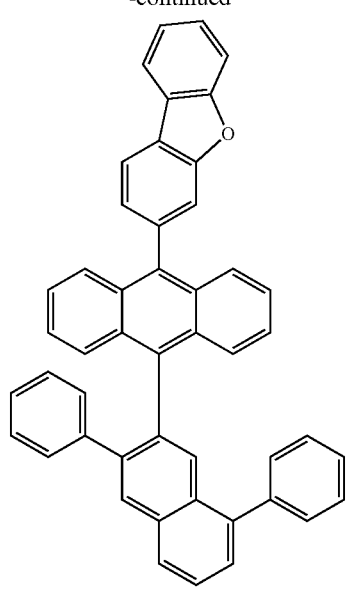
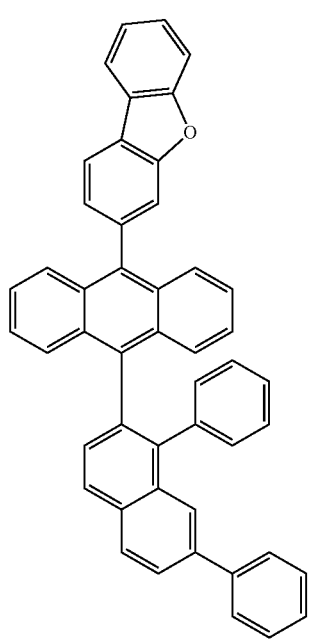
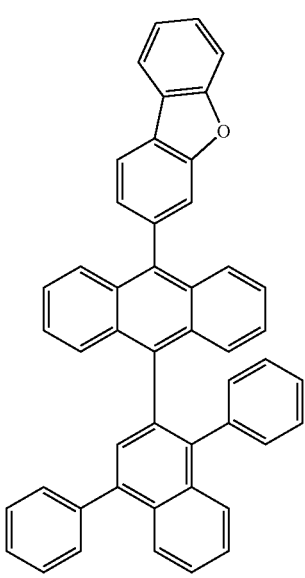

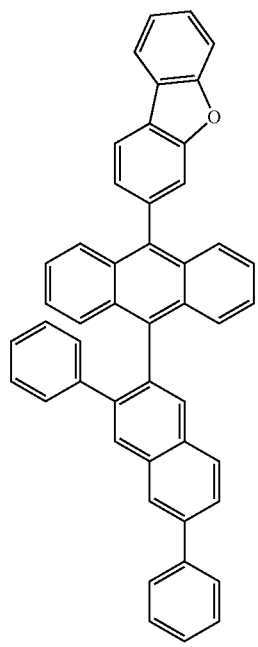
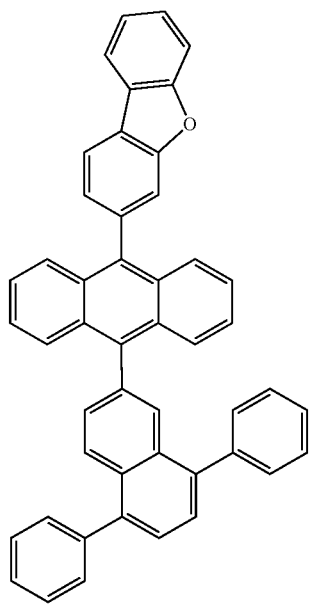
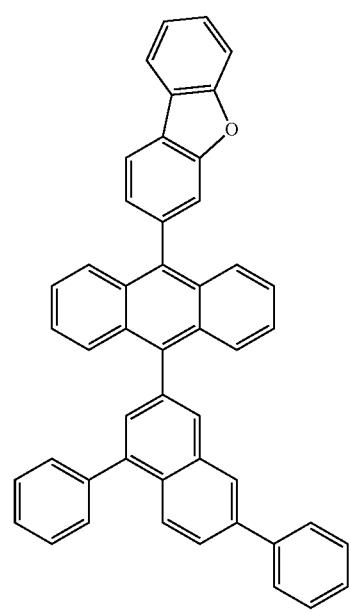

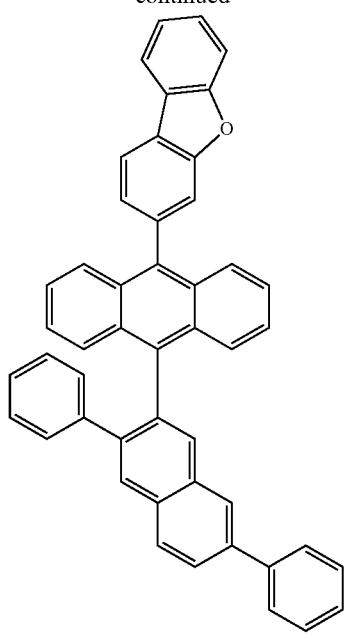

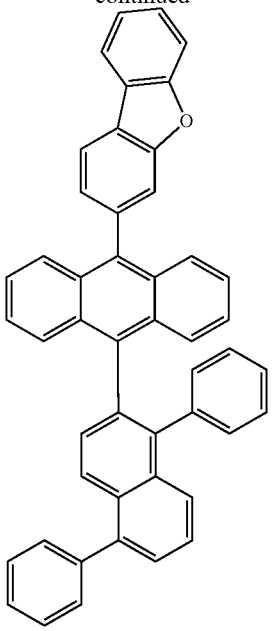

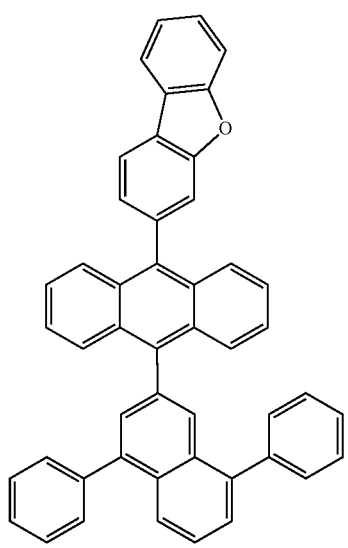

The organic light emitting device of the present invention includes: a first electrode; a second electrode provided to face the first electrode; and an organic material layer having one or two or more layers provided between the first electrode and the second electrode, and one or more layers of the organic material layer may include the above-described compound.

For example, the structure of the organic light emitting device of the present invention may have a structure as illustrated in FIGS. 1 and 2, but is not limited thereto.

FIG. 1 exemplifies a structure of an organic light emitting device in which a first electrode 2, an organic material layer 3, and a second electrode 4 are sequentially stacked on a substrate 1.

FIG. 1 exemplifies an organic light emitting device, and the organic light emitting device is not limited thereto.

FIG. 2 exemplifies a structure of an organic light emitting device in which a first electrode 2, a hole injection layer 5, a hole transport layer 6, an electron blocking layer 7, a light emitting layer 8, an electron transport layer 9, an electron injection layer 10, and a second electrode 4 are sequentially stacked on a substrate 1.

FIG. 2 exemplifies an organic light emitting device, and the organic light emitting device is not limited thereto, and may further include an additional organic material layer between the light emitting 5 and the second electrode 4.

In an exemplary embodiment of the present invention, the organic material layer includes a light emitting layer, and the light emitting layer includes the compound of Formula 1.

The organic light emitting device of the present invention includes a light emitting layer, and the light emitting layer may include a host and a dopant at a mass ratio of 99:1 to 80:20.

In an exemplary embodiment of the present invention, the organic material layer includes a light emitting layer, and the light emitting layer includes the compound of Formula 1 as a host.

In an exemplary embodiment of the present invention, the organic material layer includes a light emitting layer, and the light emitting layer includes the compound of Formula 1 as a blue host.

In an exemplary embodiment of the present specification, the light emitting layer includes a compound of the following Formula A as a dopant.

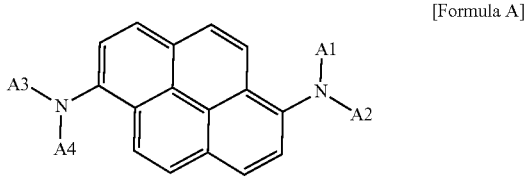

[Formula A]

In Formula A,

A1 to A4 are the same as or different from each other, and are each independently a substituted or unsubstituted aryl group, or a substituted or unsubstituted heteroaryl group.

In an exemplary embodiment of the present invention, A1 to A4 are the same as or different from each other, and are each independently a substituted or unsubstituted aryl group having 6 to 30 carbon atoms; or a substituted or unsubstituted heteroaryl group having 3 to 30 carbon atoms.

In an exemplary embodiment of the present invention, A1 to A4 are the same as or different from each other, and are each independently a phenyl group, a biphenyl group, a terphenyl group, an anthracene group, a phenanthrene group, a fluorene group, a triphenylene group, a carbazole group, a dibenzofuran group, or a dibenzothiophene group.

In an exemplary embodiment of the present invention, A1 to A4 are the same as or different from each other, and are each independently a biphenyl group, or a dibenzofuran group.

In an exemplary embodiment of the present invention, the organic material layer may include a hole injection layer, a hole transport layer, or a hole injection and transport layer, and the hole injection layer, the hole transport layer, or the hole injection and transport layer may include the compound of Formula 1.

In an exemplary embodiment of the present invention, the organic material layer may include an electron injection layer, an electron transport layer, or an electron injection and transport layer, and the electron injection layer, the electron transport layer, or the electron injection and transport layer may include the compound of Formula 1.

In an exemplary embodiment of the present invention, the organic material layer may include an electron blocking layer or a hole blocking layer, and the electron blocking layer or the hole blocking layer may include the compound of Formula 1.

For example, the organic light emitting device according to the present invention may be manufactured by depositing a metal or a metal oxide having conductivity, or an alloy thereof on a substrate to form a positive electrode, forming an organic material layer including a hole injection layer, a hole transport layer, a light emitting layer, and an electron transport layer and an organic material layer including the compound of Formula 1 thereon, and then depositing a material, which may be used as a negative electrode, thereon, by using a physical vapor deposition (PVD) method such as sputtering or e-beam evaporation. In addition to the method described above, an organic light emitting device may also be made by sequentially depositing a negative electrode material, an organic material layer, and a positive electrode material on a substrate.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylcompound), poly[3,4-(ethylene-1,2-dioxy)compound](PEDT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or LiO$_2$/Al; and the like, but are not limited thereto.

The hole injection material is a material which may proficiently receive holes from a positive electrode at low voltage, and the highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline and polycompound-based conductive polymer, and the like, but are not limited thereto.

The hole transport material is suitably a material having high hole mobility which may receive holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is a material which may receive holes and electrons from a hole transport layer and an electron transport layer, and combine the holes and the electrons to emit light in a visible ray region, and is preferably a material having high quantum efficiency for fluorescence or phosphorescence. Specific examples thereof include: 8-hydroxy-quinoline aluminum complexes (Alq$_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

When the organic light emitting device includes a plurality of organic material layers, the organic material layers may be formed of the same material or different materials.

The organic light emitting device of the present specification may be manufactured by the materials and methods known in the art, except that one or more layers of the organic material layer are formed by using the compound.

The present specification also provides a method for manufacturing an organic light emitting device formed by using the compound.

Examples of the dopant material include aromatic compounds, styrylamine compounds, boron complexes, fluoranthene compounds, metal complexes, and the like. Specifically, the aromatic compound is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include iridium complexes, platinum complexes, and the like, but are not limited thereto.

The electron transport layer is a layer which accepts electrons from an electron injection layer and transports the electrons to a light emitting layer, and an electron transport material is suitably a material having high electron mobility which may proficiently accept electrons from a cathode and transfer the electrons to a light emitting layer. Specific examples thereof include: Al complexes of 8-hydroxyquinoline; complexes including Alq3; organic radical compounds; hydroxyflavone-metal complexes, and the like, but are not limited thereto. The electron transport layer may be used with any desired cathode material, as used according to the related art. In particular, appropriate examples of the cathode material include a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a cathode, and may be generally formed under the same conditions as those of the hole injection layer. Specific examples thereof include oxadiazole derivatives or triazole derivatives, phenanthroline derivatives, BCP, aluminum complexes, and the like, but are not limited thereto.

The organic light emitting device according to the present specification may be a top emission type, a bottom emission type, or a dual emission type according to the materials to be used.

The organic light emitting device of the present invention may be manufactured using typical manufacturing methods and materials of an organic light emitting device, except that the above-described compound is used to form an organic material layer having one or more layers.

[Best Mode]

The preparation method of the compound of Formula 1 and the manufacture of an organic light emitting device using the same will be specifically described in the following Examples. However, the following Examples are provided for exemplifying the present invention, and the scope of the present invention is not limited thereby. In the following reaction formulae, with respect to the type and number of substituent, various types of intermediates may be synthesized as a person skilled in the art appropriately selects a publicly-known starting material. As the type of reaction and the reaction condition, those known in the art may be used.

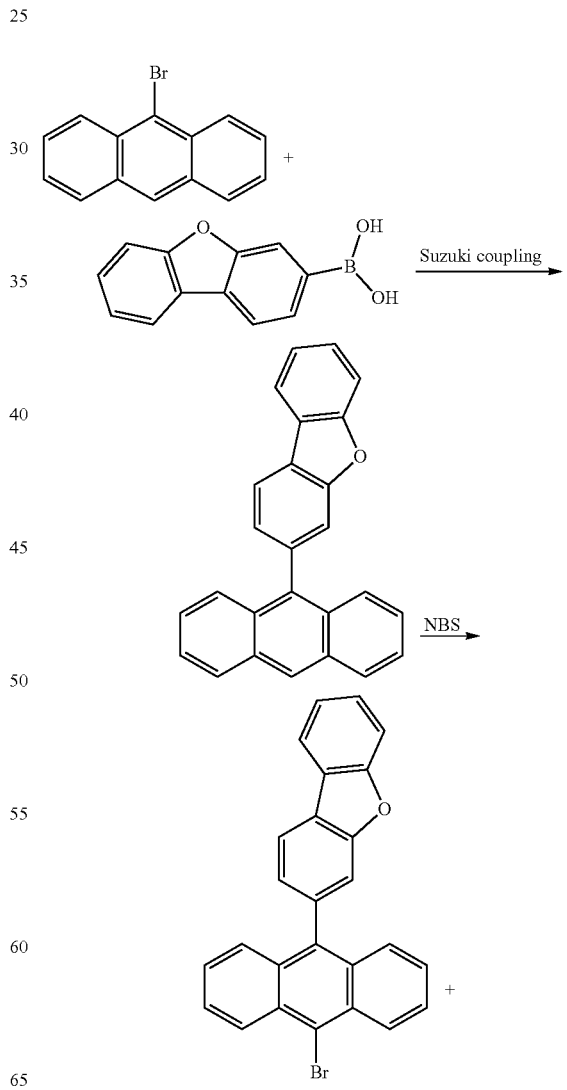

-continued

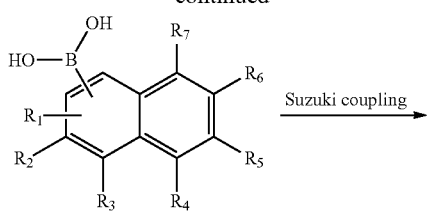

Suzuki coupling

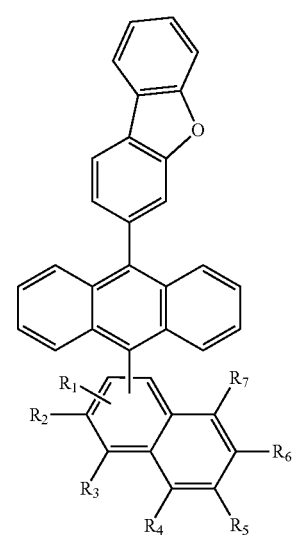

When the preparation formula described in the Examples of the present specification and the intermediates are appropriately combined based on a typical technology common sense, all of the compounds of Formula 1 described in the present specification can be all prepared.

PREPARATION EXAMPLES

<Preparation Example 1> Preparation of Compound 1

(Preparation Example 1-1) Preparation of Compound 1-1

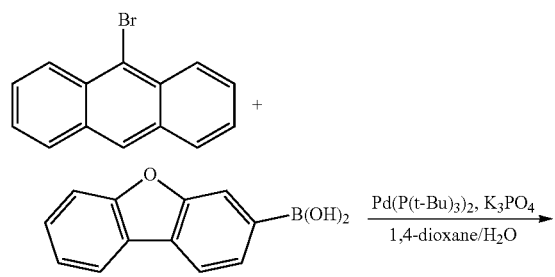

Pd(P(t-Bu)₃)₂, K₃PO₄
1,4-dioxane/H₂O

-continued

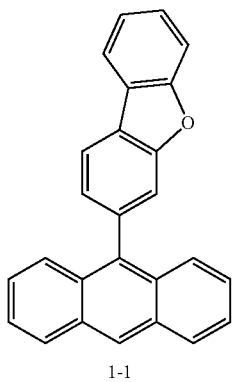

1-1

9-bromoanthracene (20.0 g, 77.8 mmol) and dibenzo[b,d]furan-3-ylboronic acid (18.1 g, 85.6 mmol) were dissolved in 300 ml of 1,4-dioxane, K₃PO₄ (49.5 g, 233.3 mmol) was dissolved in 150 ml of H₂O, and the resulting solutions were put into a 3-neck flask. Pd(P(t-Bu)₃)₂ (0.8 g, 1.6 mmol) was added thereto, and the resulting mixture was stirred under an argon atmosphere reflux condition for 8 hours. When the reaction was terminated, the flask was cooled to room temperature, and then the reaction solution was transferred to a separatory funnel and extracted with water and ethyl acetate. The extract was dried over MgSO₄, filtered and concentrated, and then the sample was purified with silica gel column chromatography to obtain 20.1 g of Compound 1-1 (yield 75%, MS[M+H]⁺=344).

(Preparation Example 1-2) Preparation of Compound 1-2

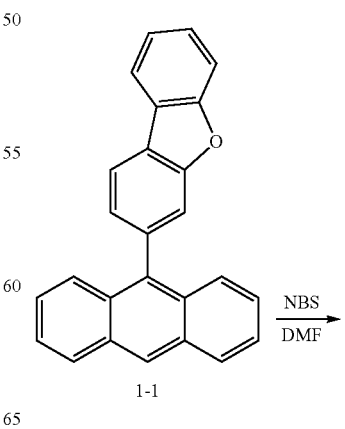

NBS
DMF 1-1

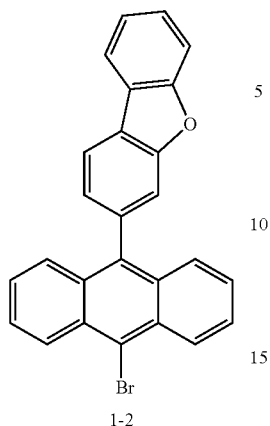

1-2

Compound 1-1 (20.0 g, 58.1 mmol), NBS (10.9 g, 61.0 mmol), 400 mL of DMF were put into a 2-neck flask, and stirred at room temperature under an argon atmosphere for 8 hours. After the reaction was terminated, the reaction solution was transferred to a separatory funnel and the organic layer was extracted with water and ethyl acetate. The extract was dried over $MgSO_4$, filtered, and concentrated, and then the sample was purified with silica gel column chromatography to obtain 21.6 g of Compound 1-2 (yield 88%, MS[M+H]$^+$=423).

(Preparation Example 1-3) Preparation of Compound 1

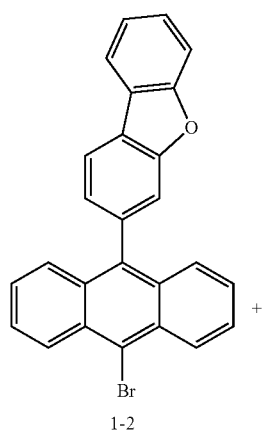

1-2

+

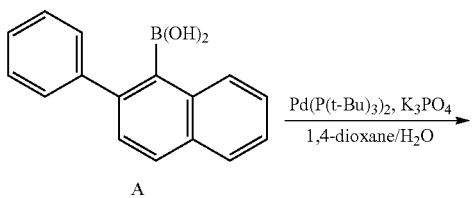

A

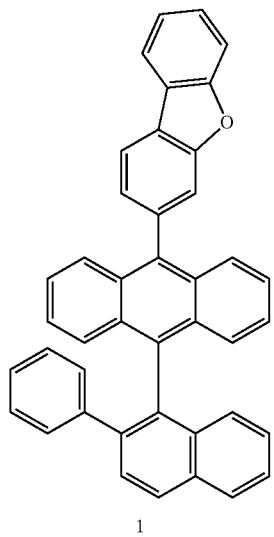

1

Compound 1-2 (20.0 g, 47.2 mmol) and Intermediate A (12.9 g, 52.0 mmol) were dissolved in 300 ml of 1,4-dioxane, $K_3PO_4$ (30.1 g, 141.7 mmol) was dissolved in 150 ml of $H_2O$, and the resulting solutions were put into a 3-neck flask. Pd(P(t-Bu)$_3$)$_2$ (0.5 g, 0.9 mmol) was added thereto, and the resulting mixture was stirred under an argon atmosphere reflux condition for 8 hours. When the reaction was terminated, the flask was cooled to room temperature, and then the reaction solution was transferred to a separatory funnel and extracted with water and ethyl acetate. The extract was dried over $MgSO_4$, filtered and concentrated, and then the sample was purified with silica gel column chromatography and then subjected to sublimation purification to obtain 8.0 g of Compound 1 (yield 31%, MS[M+H]$^+$=546).

<Preparation Example 2> Preparation of Compound 2

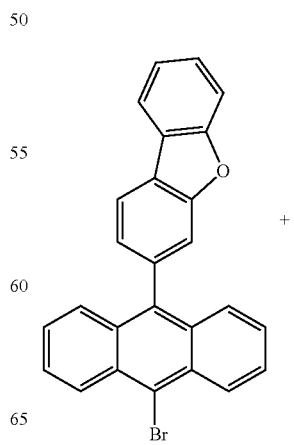

+

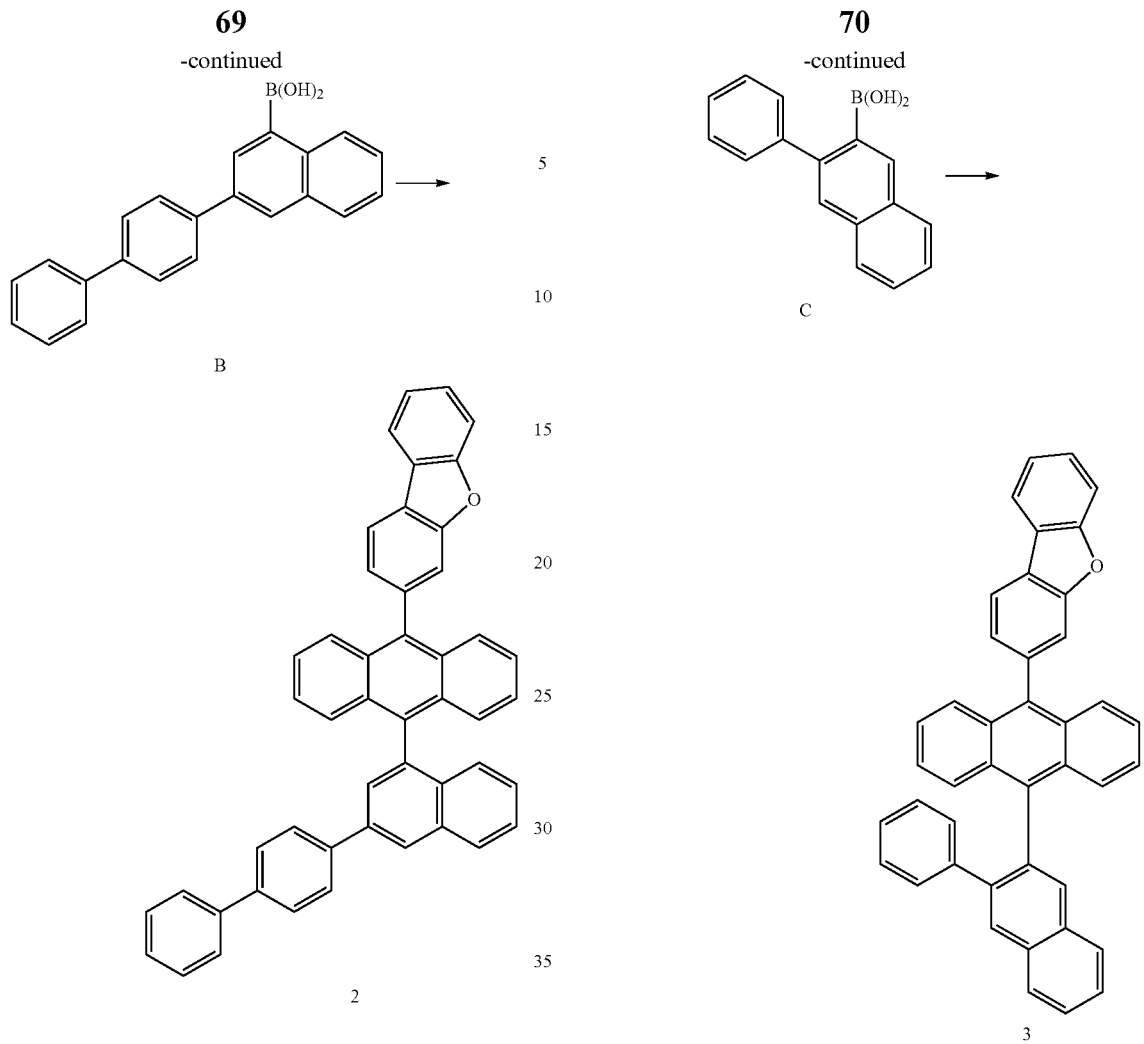

8.2 g of Compound 2 was prepared using the same method as the method of preparing Compound 1, except that in (Preparation Example 1-3), Intermediate A was changed into Intermediate B and Intermediate B was used (yield 28% MS[M+H]⁺=622).

<Preparation Example 3> Preparation of Compound 3

7.7 g of Compound 3 was prepared using the same method as the method of preparing Compound 1, except that in (Preparation Example 1-3), Intermediate A was changed into Intermediate C and Intermediate C was used (yield 30%, MS [M+H]⁺=546).

<Preparation Example 4> Preparation of Compound 4

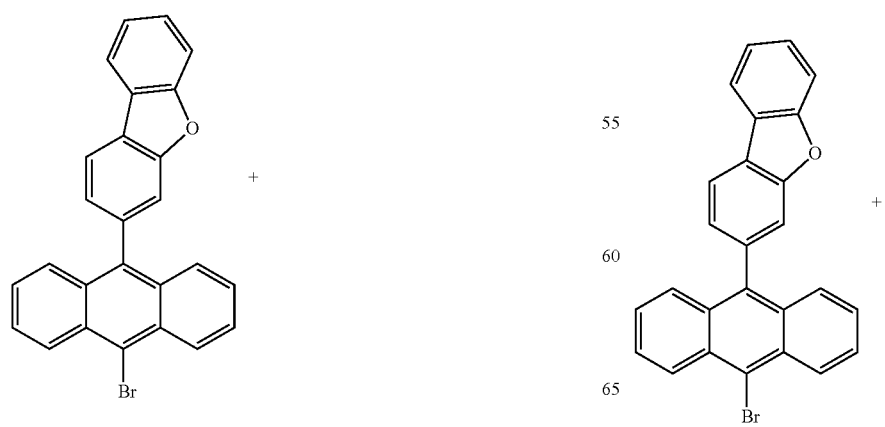

-continued

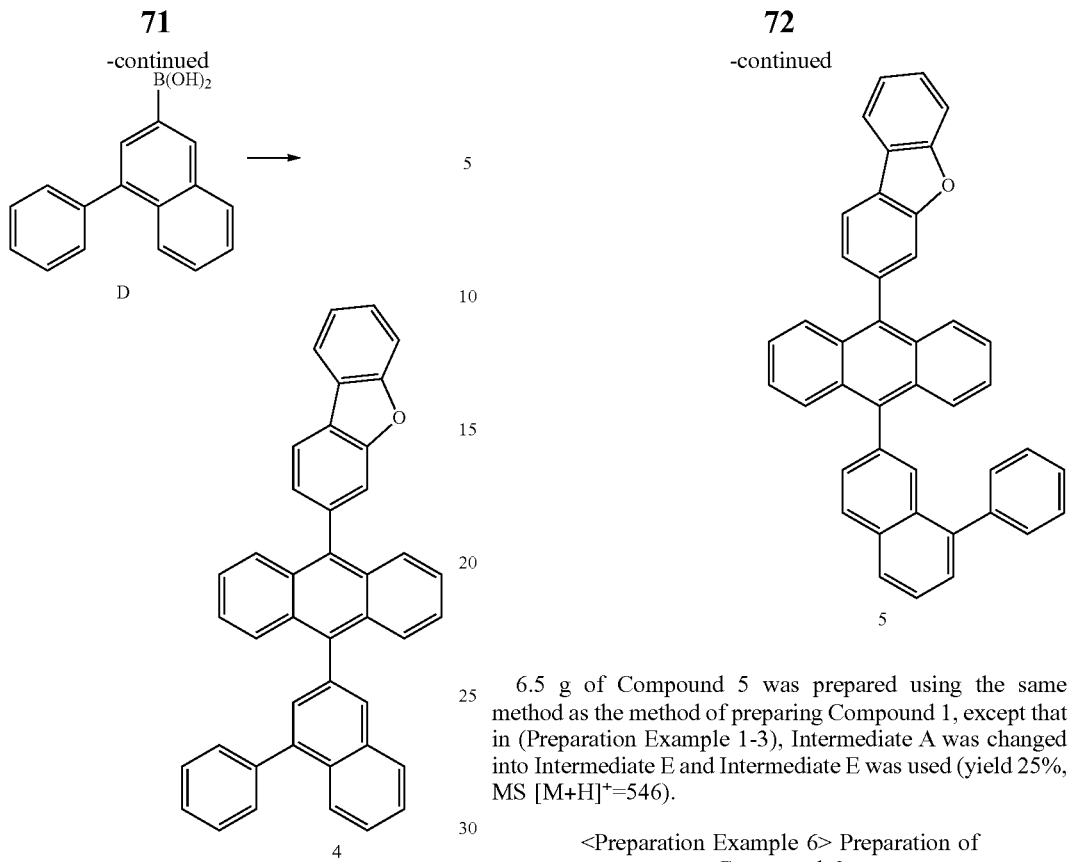

8.5 g of Compound 4 was prepared using the same method as the method of preparing Compound 1, except that in (Preparation Example 1-3), Intermediate A was changed into Intermediate D and Intermediate D was used (yield 33%, MS [M+H]⁺=546).

<Preparation Example 5> Preparation of Compound 5

-continued

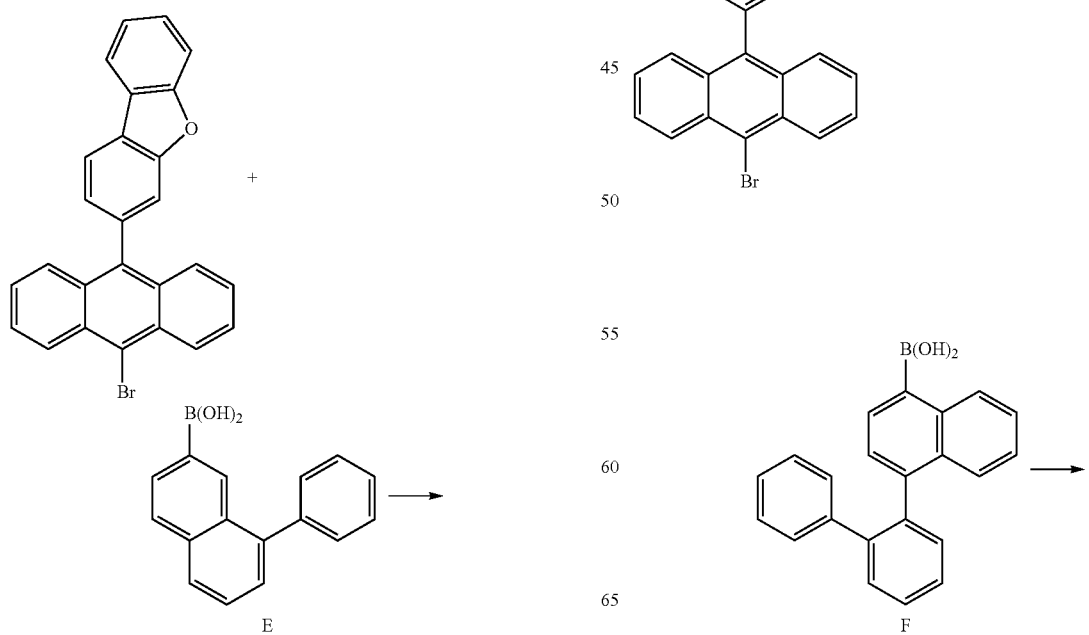

6.5 g of Compound 5 was prepared using the same method as the method of preparing Compound 1, except that in (Preparation Example 1-3), Intermediate A was changed into Intermediate E and Intermediate E was used (yield 25%, MS [M+H]⁺=546).

<Preparation Example 6> Preparation of Compound 6

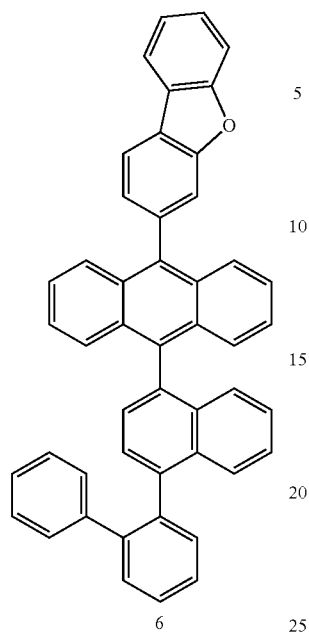

6

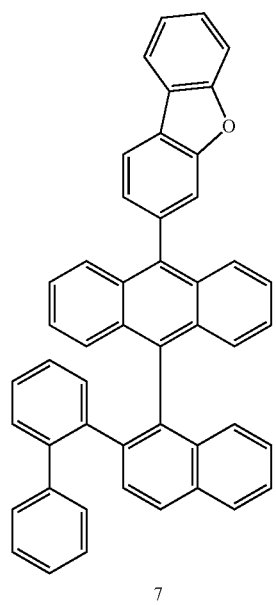

7

8.2 g of Compound 6 was prepared using the same method as the method of preparing Compound 1, except that in (Preparation Example 1-3), Intermediate A was changed into Intermediate F and Intermediate F was used (yield 28%, MS[M+H]⁺=622).

9.4 g of Compound 7 was prepared using the same method as the method of preparing Compound 1, except that in (Preparation Example 1-3), Intermediate A was changed into Intermediate G and Intermediate G was used (yield 32%, MS [M+H]⁺=622).

<Preparation Example 7> Preparation of Compound 7

<Preparation Example 8> Preparation of Compound 8

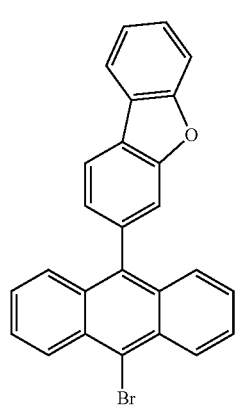

+

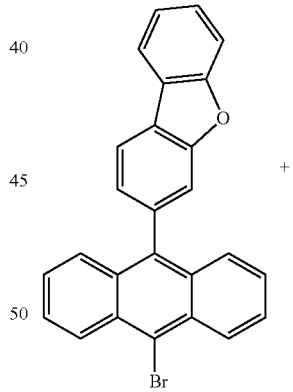

+

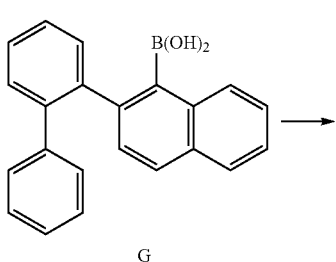

G

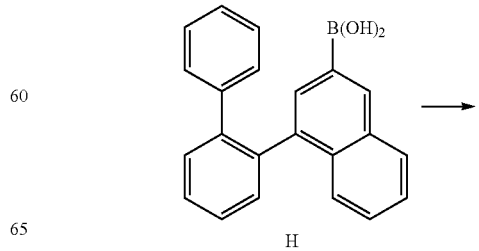

H

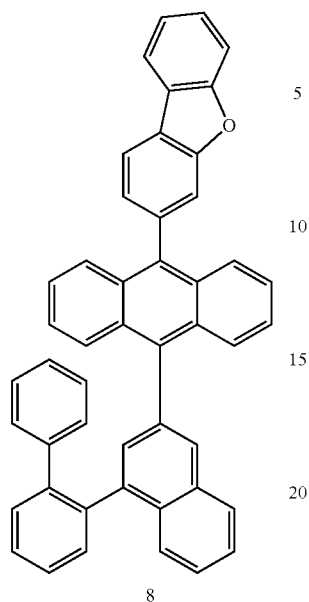

8.8 g of Compound 8 was prepared using the same method as the method of preparing Compound 1, except that in (Preparation Example 1-3), Intermediate A was changed into Intermediate H and Intermediate H was used (yield 30%, MS[M+H]$^+$=622).

<Preparation Example 9> Preparation of Compound 9

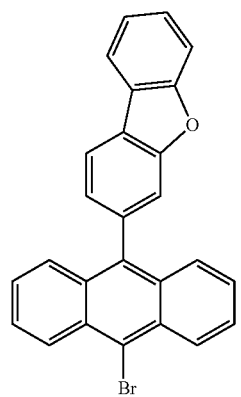

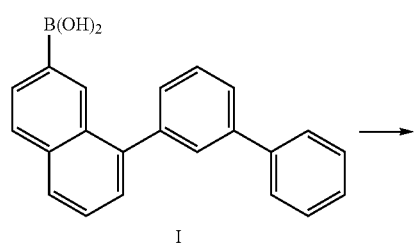

8.2 g of Compound 9 was prepared using the same method as the method of preparing Compound 1, except that in (Preparation Example 1-3), Intermediate A was changed into Intermediate I and Intermediate I was used (yield 28%, MS [M+H]$^+$=622).

<Preparation Example 10> Preparation of Compound 10

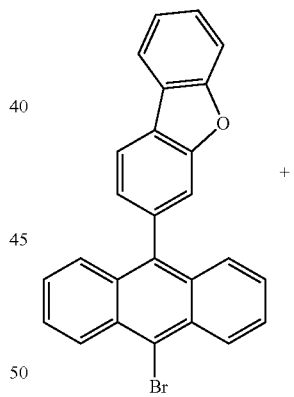

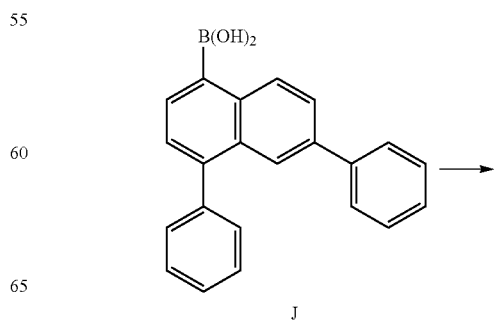

-continued

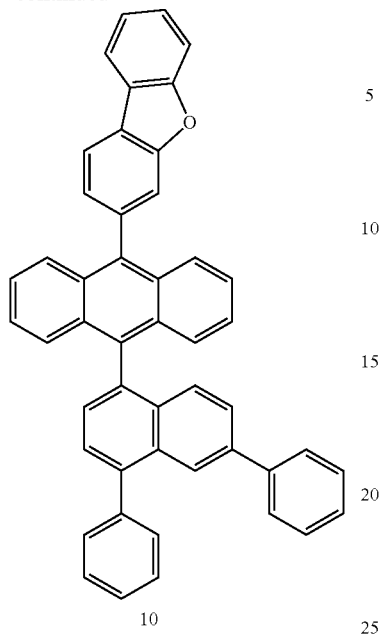

10

7.1 g of Compound 10 was prepared using the same method as the method of preparing Compound 1, except that in (Preparation Example 1-3), Intermediate A was changed into Intermediate J and Intermediate J was used (yield 24%, MS [M+H]⁺=622).

<Preparation Example 11> Preparation of Compound 11

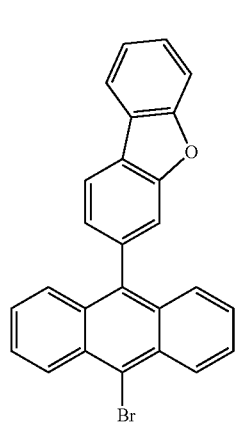

-continued

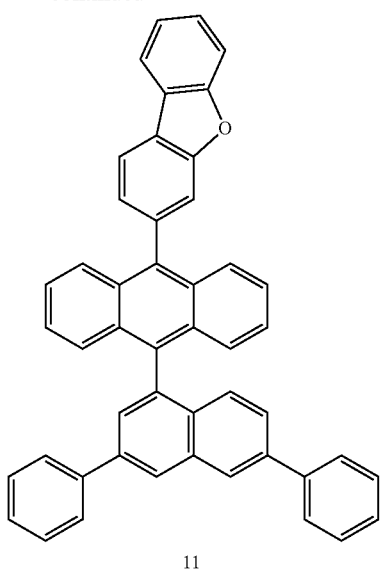

11

9.4 g of Compound 11 was prepared using the same method as the method of preparing Compound 1, except that in (Preparation Example 1-3), Intermediate A was changed into Intermediate K and Intermediate K was used (yield 32%, MS[M+H]⁺=622).

<Preparation Example 12> Preparation of Compound 12

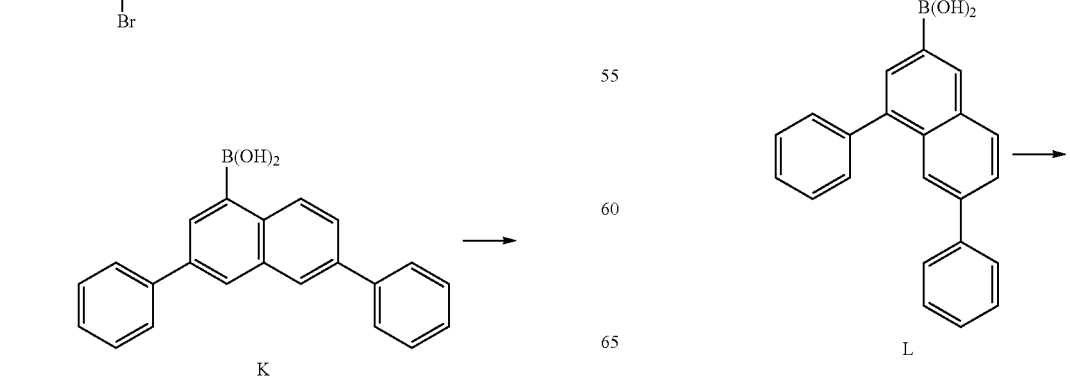

-continued

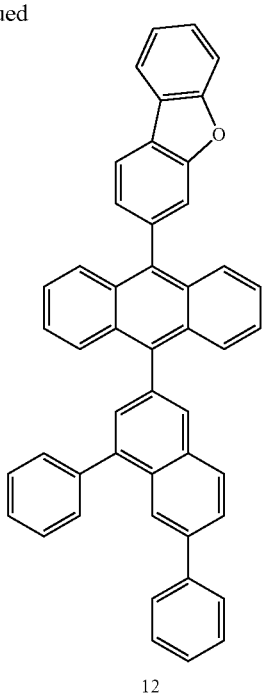

12

6.5 g of Compound 12 was prepared using the same method as the method of preparing Compound 1, except that in (Preparation Example 1-3), Intermediate A was changed into Intermediate L and Intermediate L was used (yield 22%, MS [M+H]⁺=622).

EXPERIMENTAL EXAMPLES

Comparative Example 1

A glass substrate thinly coated with indium tin oxide (ITO) to have a thickness of 1,400 Å was put into distilled water in which a detergent was dissolved, and ultrasonically washed. In this case, a Decon™ CON705 product manufactured by the Fischer Co., was used as the detergent, and distilled water twice filtered using a 0.22-μm sterilizing filter manufactured by Millipore Co., was used as the distilled water. After the ITO was washed for 30 minutes, ultrasonic washing was repeated twice by using distilled water for 10 minutes. After washing with distilled water was completed, the substrate was ultrasonically cleaned with each solvent of isopropyl alcohol, acetone and methanol for 10 minutes, dried, and then transported to a plasma cleaner. Furthermore, the substrate was cleaned by using oxygen plasma for 5 minutes, and then was transported to a vacuum deposition machine.

The following HT and PD were thermally vacuum-deposited to have a thickness of 100 Å at a weight ratio of 95:5 on the transparent ITO electrode, which was thus prepared, thereby forming a hole injection layer, and only the HT material was subsequently vacuum-deposited to have a thickness of 1100 Å, thereby forming a hole transport layer. A compound represented by the following EB was thermally vacuum-deposited as an electron blocking layer thereon to have a thickness of 50 Å. Subsequently, BH-A and a compound represented by the following BD were vacuum-deposited as a light emitting layer at a weight ratio of 96:4 to have a thickness of 200 Å. Subsequently, ET and a compound represented by Liq were thermally vacuum-deposited as an electron transport layer at a weight ratio of 1:1 to have a thickness of 360 Å, and subsequently, the following compound represented by Liq was vacuum-deposited to have a thickness of 5 Å, thereby forming an electron injection layer. A negative electrode was formed by subsequently depositing magnesium and silver at a weight ratio of 10:1 to have a thickness of 220 Å and aluminum to have a thickness of 1,000 Å on the electron injection layer, thereby manufacturing an organic light emitting device.

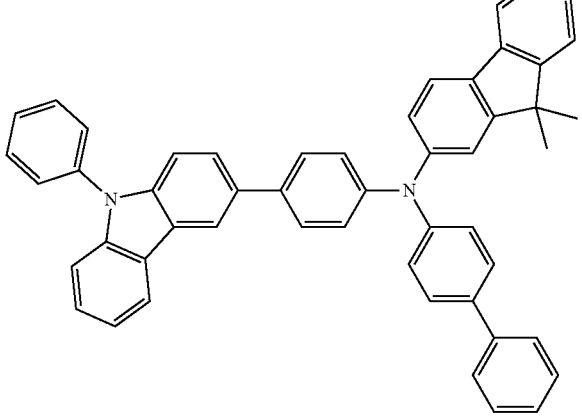

HT

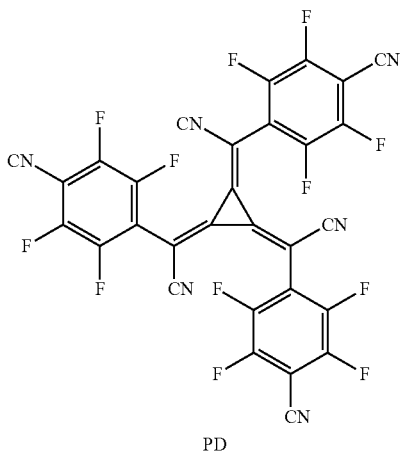

PD

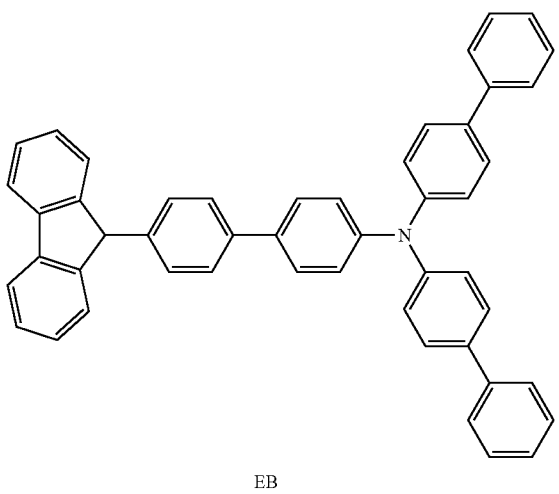

EB

-continued

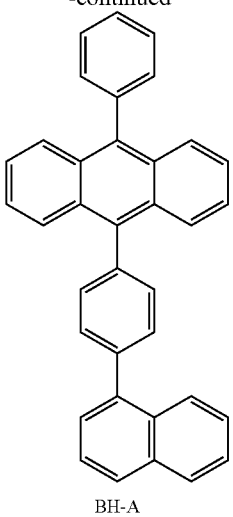
BH-A

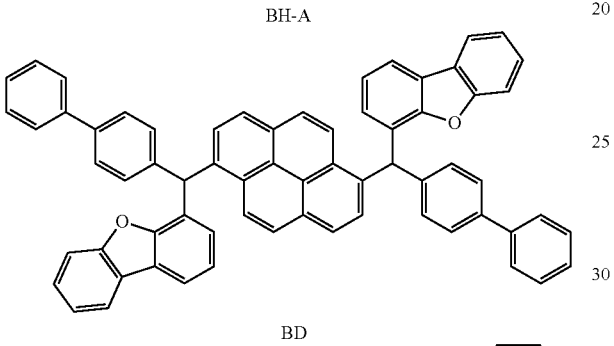
BD

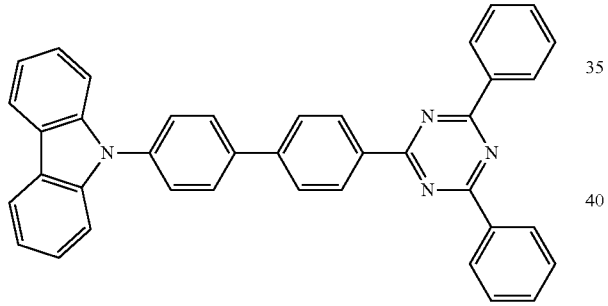
ET

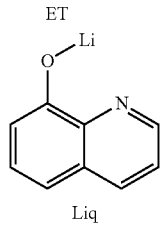
Liq

<Experimental Example 1> to <Example 12>

Organic light emitting devices were manufactured in the same manner as in Comparative Example 1, except that in Comparative Example 1, the compounds described in Table 1 were used instead of BH-1 as a host compound of the light emitting layer.

<Comparative Example 2> to <Comparative Example 11>

Organic light emitting devices were manufactured in the same manner as in Comparative Example 1, except that in Comparative Example 1, the compounds described in Table 1 were used instead of BH-A as a host compound of the light emitting layer. Further, the respective compounds of BH-B to BH-K in the following Table 1 are as follows.

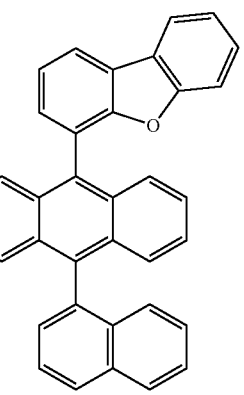
BH-B

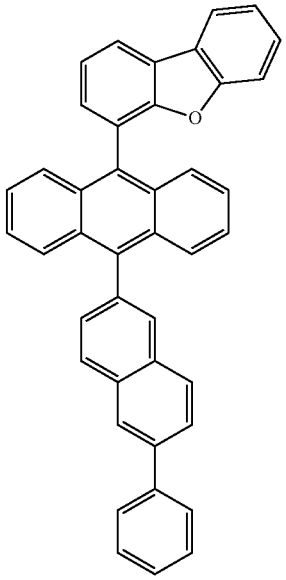
BH-C

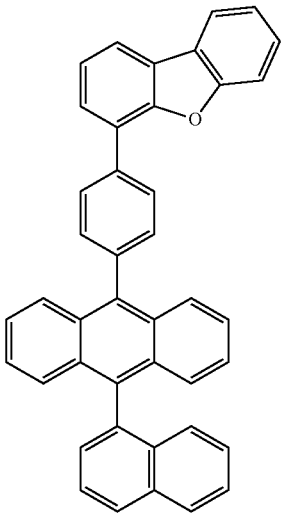
BH-D

BH-E
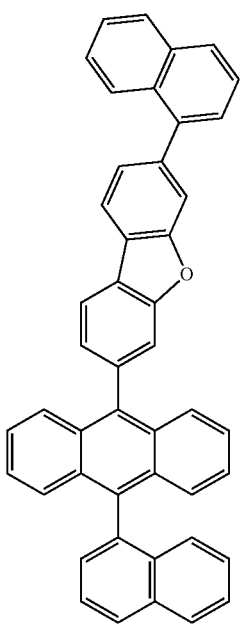
BH-F
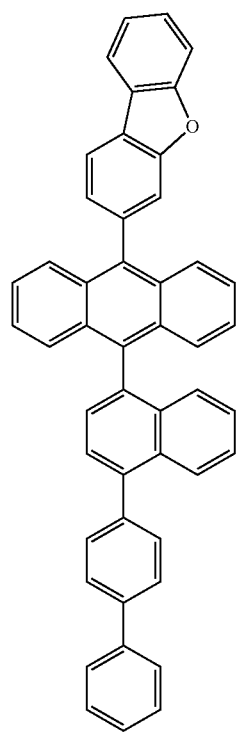
BH-G
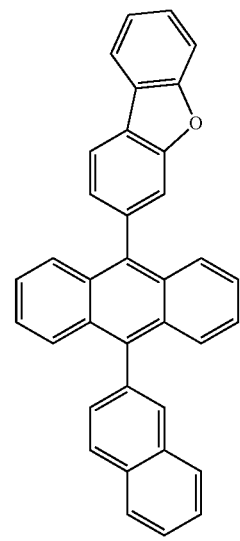
BH-H
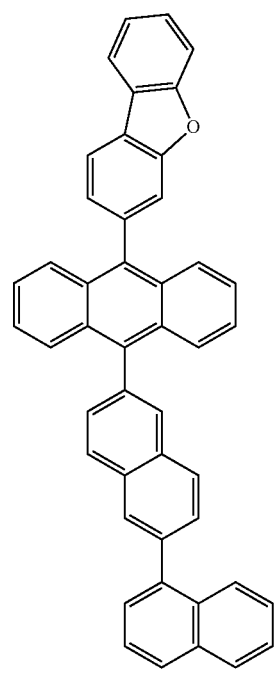
BH-I
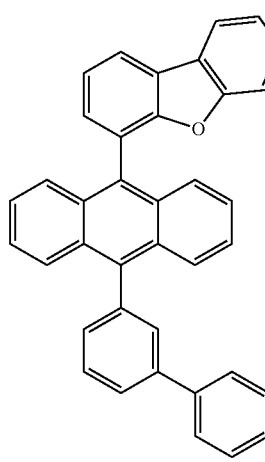

BH-J

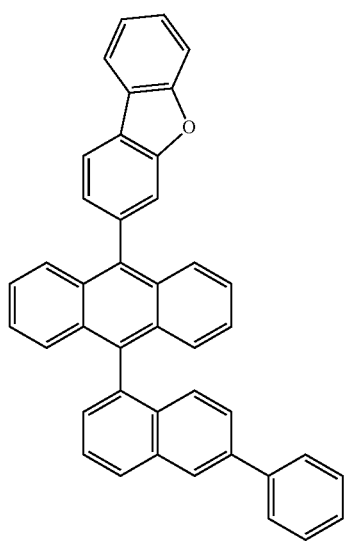

BH-K

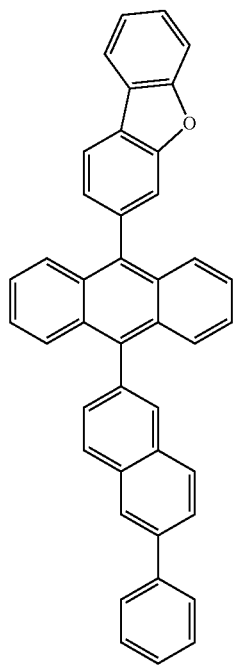

The voltage, efficiency, and service life (T95) were measured by applying a current to the organic light emitting devices manufactured in the Experimental Examples and Comparative Examples, and the results thereof are shown in the following Table 1. In this case, the voltage and efficiency were measured by applying a current density of 10 mA/cm$^2$, and T95 means the time taken for the initial luminance to be reduced to 95% at a current density of 20 mA/cm$^2$.

TABLE 1

| | Host Material | Voltage (V) (@10 mA/cm$^2$) | Efficiency (cd/A) (@10 mA/cm$^2$) | Service life (T95, hr) (@20 mA/cm$^2$) |
|---|---|---|---|---|
| Experimental Example 1 | Compound 1 | 4.65 | 6.07 | 65 |
| Experimental Example 2 | Compound 2 | 4.67 | 6.05 | 60 |
| Experimental Example 3 | Compound 3 | 4.69 | 6.09 | 66 |
| Experimental Example 4 | Compound 4 | 4.69 | 6.04 | 68 |
| Experimental Example 5 | Compound 5 | 4.68 | 6.13 | 67 |
| Experimental Example 6 | Compound 6 | 4.60 | 6.31 | 85 |
| Experimental Example 7 | Compound 7 | 4.61 | 6.35 | 88 |
| Experimental Example 8 | Compound 8 | 4.62 | 6.36 | 80 |
| Experimental Example 9 | Compound 9 | 4.63 | 6.33 | 91 |
| Experimental Example 10 | Compound 10 | 4.53 | 6.51 | 70 |
| Experimental Example 11 | Compound 11 | 4.51 | 6.50 | 76 |
| Experimental Example 12 | Compound 12 | 4.55 | 6.53 | 78 |
| Comparative Example 1 | BH-A | 4.95 | 5.33 | 45 |
| Comparative Example 2 | BH-B | 5.62 | 5.10 | 25 |
| Comparative Example 3 | BH-C | 5.55 | 5.21 | 20 |
| Comparative Example 4 | BH-D | 5.70 | 3.12 | 10 |
| Comparative Example 5 | BH-E | 4.90 | 3.51 | 15 |
| Comparative Example 6 | BH-F | 4.65 | 5.12 | 53 |
| Comparative Example 7 | BH-G | 4.70 | 5.10 | 51 |
| Comparative Example 8 | BH-H | 4.68 | 5.06 | 40 |
| Comparative Example 9 | BH-I | 5.66 | 4.80 | 26 |
| Comparative Example 10 | BH-J | 4.66 | 6.00 | 53 |
| Comparative Example 11 | BH-K | 4.69 | 5.79 | 51 |

It can be seen that when compared to the results of Comparative Examples 2 to 4, a material bonded to anthracene at the position No. 3 of dibenzofuran exhibits lower voltage characteristics than at the position No. 4 thereof. Quantum calculations were performed on the dibenzofuran material, and the molecular orbitals thereof are shown in FIG. 3. The quantum calculations were performed by the density functional theory (DFT) of Schrodinger Material Science Suite program, and in this case, B3LYP and 6-31G* were used as the functional and the basis function, respectively. As can be seen in FIG. 3, the position No. 3 of dibenzofuran is a position where both the highest occupied molecular orbital (HOMO) and the lowest unoccupied molecular orbital (LUMO) are located, and affects both the molecular orbital functions when bonded to anthracene. Since the host material for the light emitting layer transports both holes and electrons, the dibenzofuran bond at the position No. 3 enables excellent transport of holes and electron, and particularly, the HOMO is also located at the position No. 3 unlike the other positions, and thus the dibenzofuran bond at the position No. 3 has an effect of lowering the driving voltage by increasing the HOMO energy level of the molecule and facilitating the injection of holes.

In the structure of Formula 1, the molecular weight is higher when any one or more of $R_1$ to $R_7$ are an aryl group than that when all of $R_1$ to $R_7$ are hydrogen. In general, when the molecular weight is increased, the glass transition temperature is increased, thermal stability in the film is enhanced, and thus longer service life characteristics are possessed.

However, when any one of $R_1$ to $R_7$ is a biphenyl group, in the case where all of the groups from the anthracene structure of Formula 1 to the end phenyl group of the biphenyl group are in para positions, the deposition temperature is excessively increased due to the increased molecular length, which causes a problem with process.

To avoid these problems, it is important to use a substituent whose deposition temperature is not excessively increased while having a high glass transition temperature. When any one of $R_1$ to $R_7$ is a biphenyl group, the case where any one pair of the groups from the anthracene structure of Formula 1 to the end phenyl group of the biphenyl group is in ortho or meta position, or two or more of $R_1$ to $R_7$ are each an aryl group corresponds to a substituent having a deposition temperature at a suitable level while having a high glass transition temperature.

The substituent imparts an effect of increasing the intermolecular distance to the molecule having the increased length due to the bond between anthracene and the position No. 3 of dibenzofuran, and which affects the intermolecular distance of a dopant, and thereby providing an effect of suppressing the reduction in efficiency caused by self-quenching. Consequently, when the compound of Formula 1 is used as a blue light emitting layer host of an organic light emitting device, the device with a low voltage, high efficiency, and long service life can be obtained.

Furthermore, it can be seen that Compounds 6 to 9 (Experimental Examples 6 to 9) including a biphenyl group having an ortho or meta substitution are excellent in amorphous characteristics of the compounds, thereby providing excellent service life characteristics of the device.

The invention claimed is:
1. A compound represented by the following Formula 1:

[Formula 1]

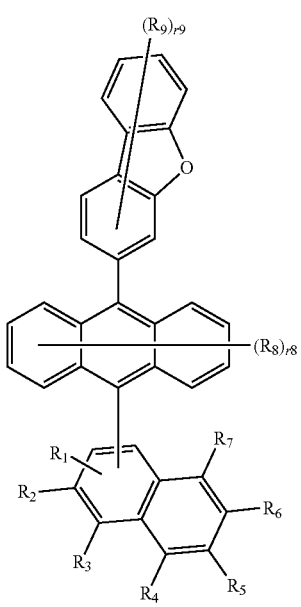

wherein in Formula 1, $R_1$ to $R_7$ are the same as or different from each other, and are each independently hydrogen, deuterium, or a substituted or unsubstituted aryl group, $R_8$ and $R_9$ are the same as or different from each other, and are each independently hydrogen or deuterium, r8 is an integer from 0 to 8, r9 is an integer from 0 to 7, and when r8 and r9 are each 2 or higher, the substituents in the parenthesis are the same as or different from each other, the following compounds are excluded from the compound represented by Formula 1, provided that at least one of $R_1$ to $R_7$ is a substituted or unsubstituted aryl group,

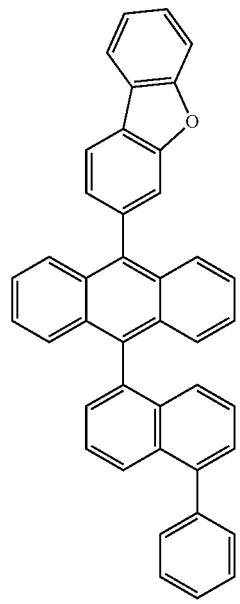

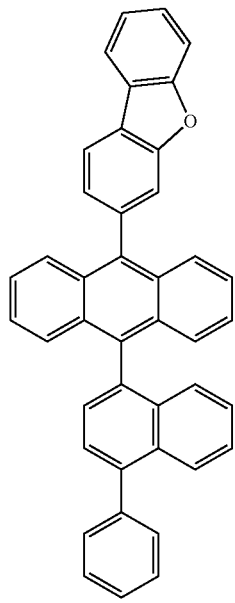

-continued
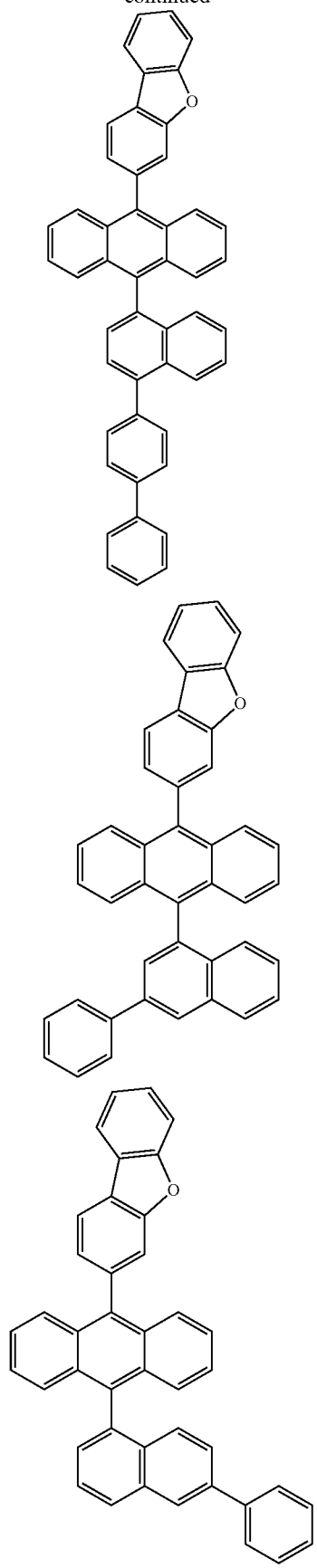
-continued
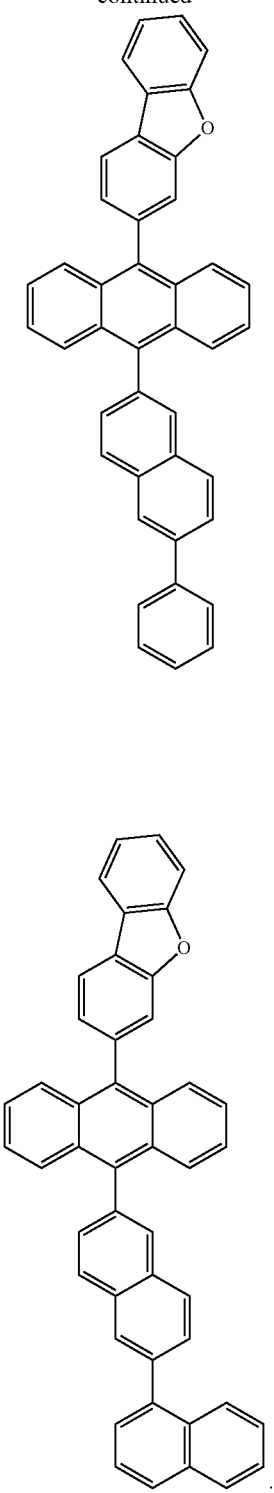
2. The compound of claim 1, wherein Formula 1 is represented by the following Formula 1-1 or 1-2:

[Formula 1-1]

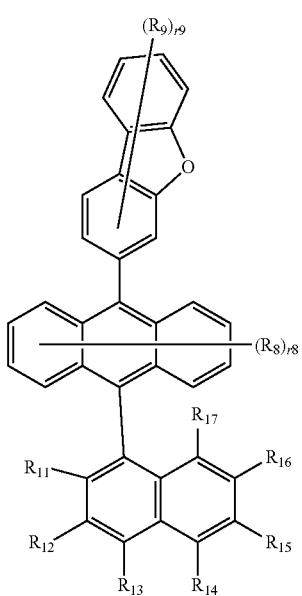

[Formula 1-2]

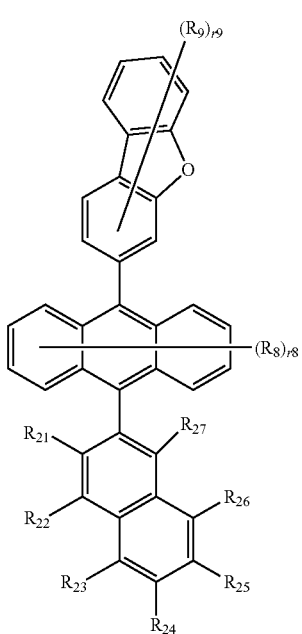

wherein in Formulae 1-1 and 1-2,
the definitions of $R_8$, $R_9$, r8 and r9 are the same as those defined for Formula 1, and
$R_{11}$ to $R_{17}$ and $R_{21}$ to $R_{27}$ are the same as or different from each other, and are each independently hydrogen, deuterium, or a substituted or unsubstituted aryl group.

3. The compound of claim 1, wherein $R_1$ to $R_7$ are the same as or different from each other, and are each independently hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracene group, a substituted or unsubstituted phenanthrene group, or a substituted or unsubstituted triphenylene group.

4. The compound of claim 1, wherein one of $R_1$ to $R_7$ is a biphenyl group, and at least one pair of groups from the anthracene group of Formula 1 to the end phenyl group of the biphenyl group forms ortho or meta substitution.

5. The compound of claim 1, wherein two or more of $R_1$ to $R_7$ are a substituted or unsubstituted aryl group.

6. The compound of claim 1, wherein the compound represented by Formula 1 is any one selected from the following compounds:

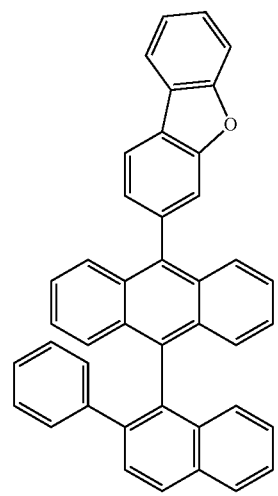

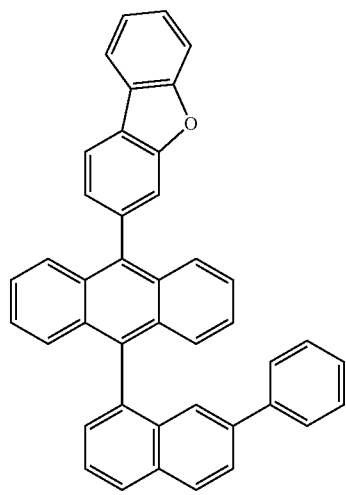

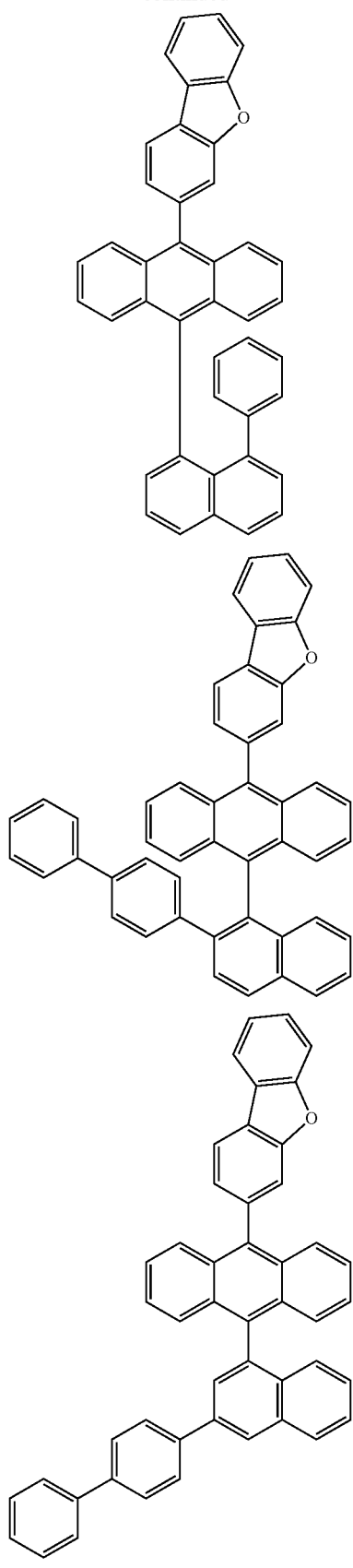
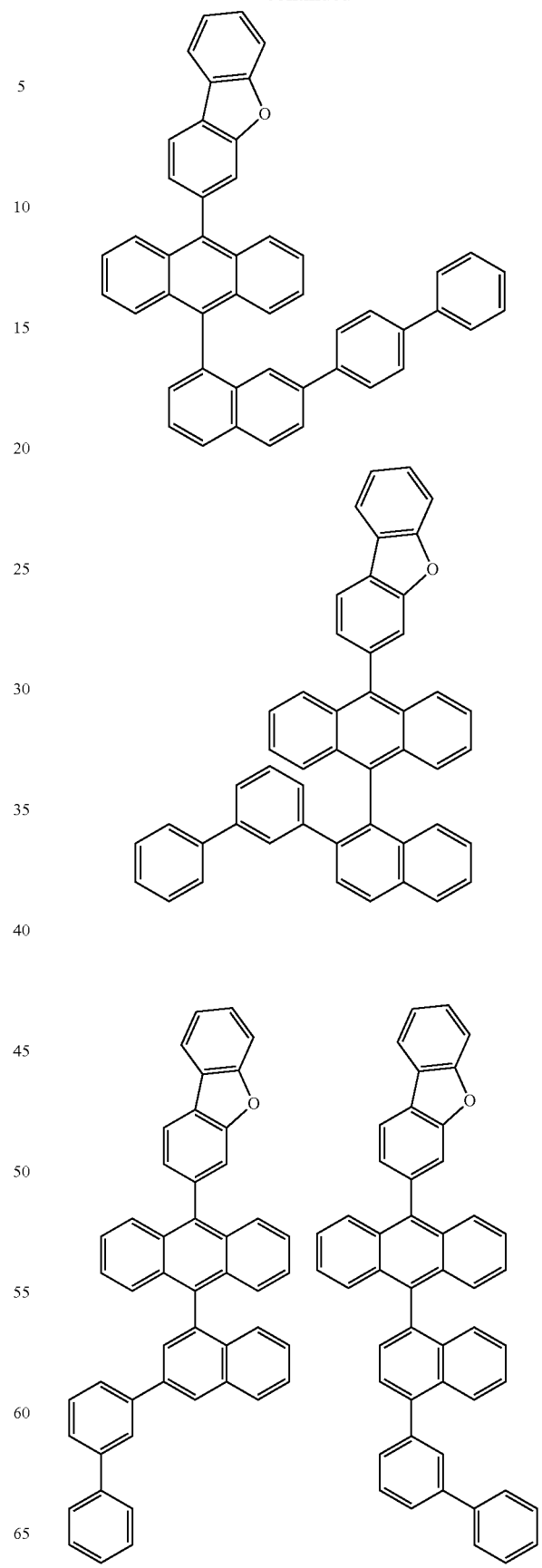

95
-continued
96
-continued
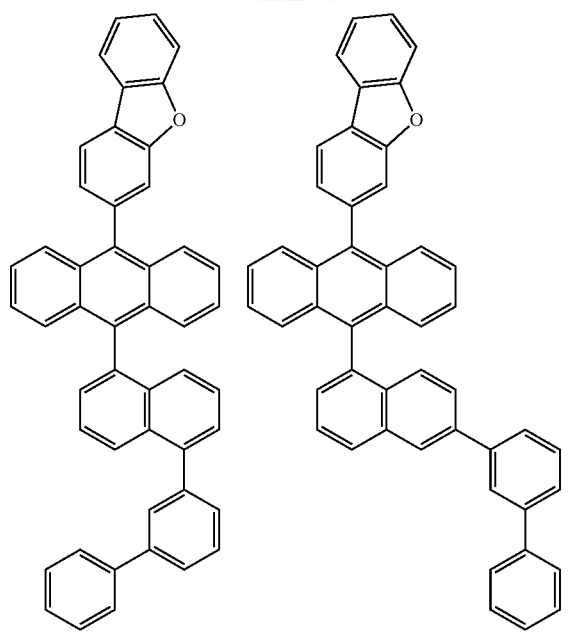
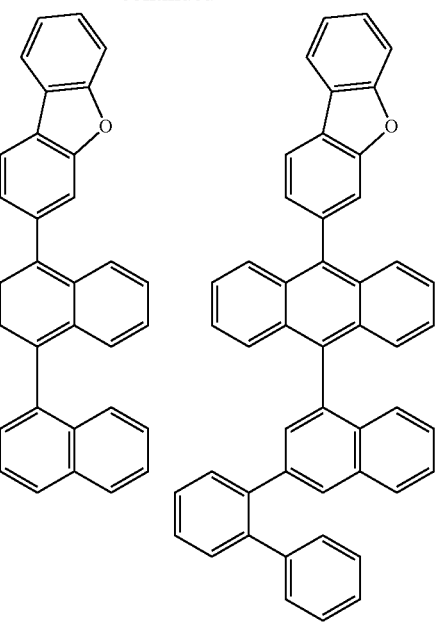
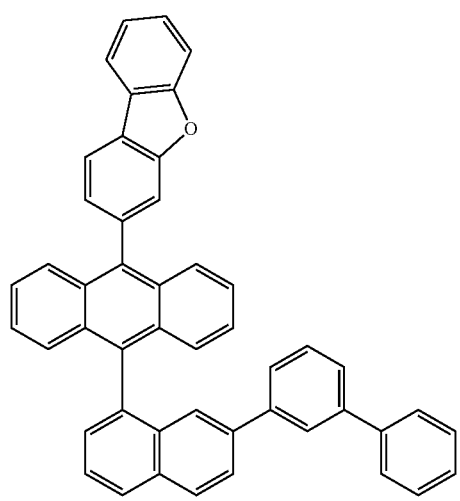
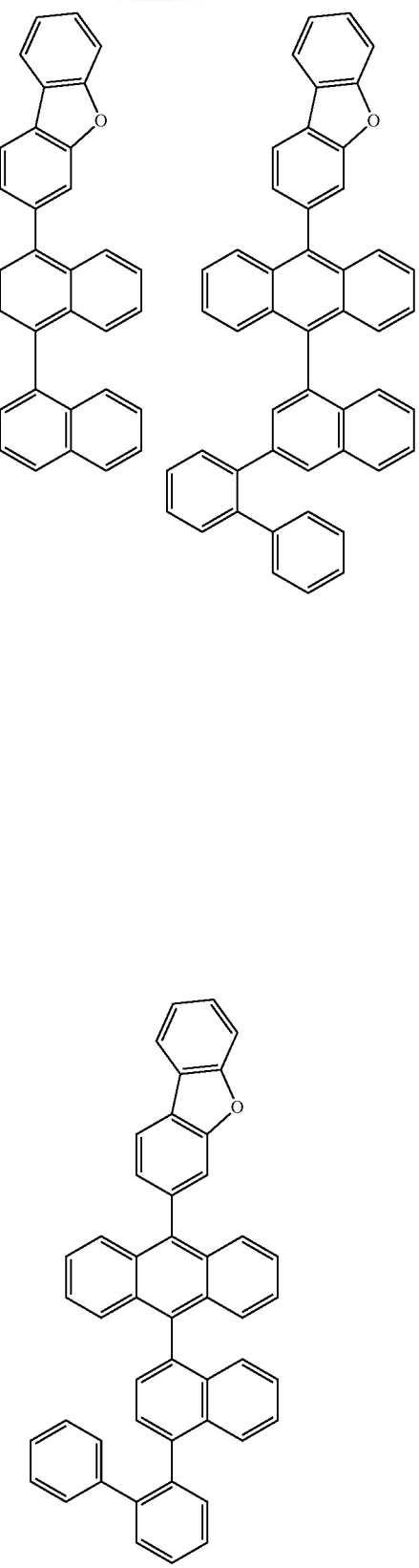

97
-continued
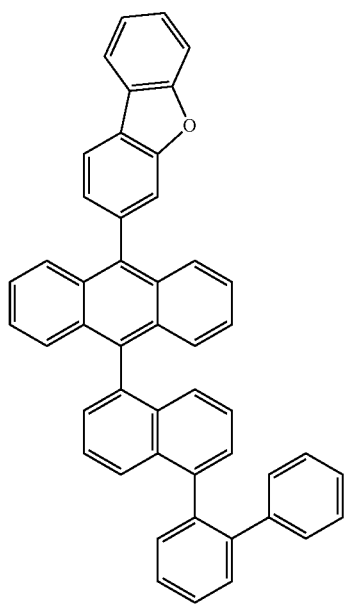
98
-continued
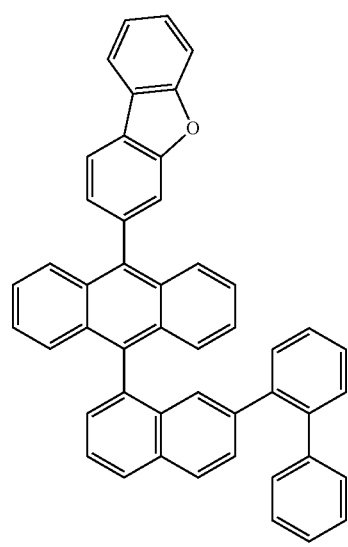
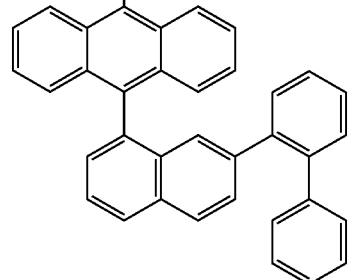
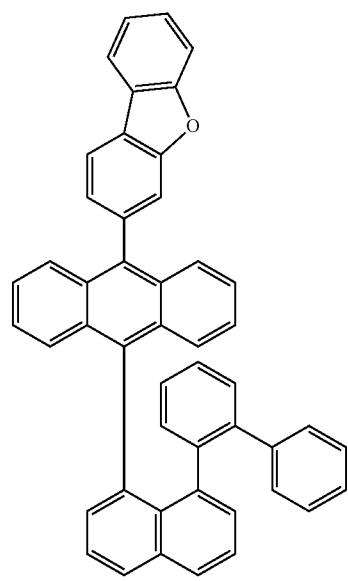
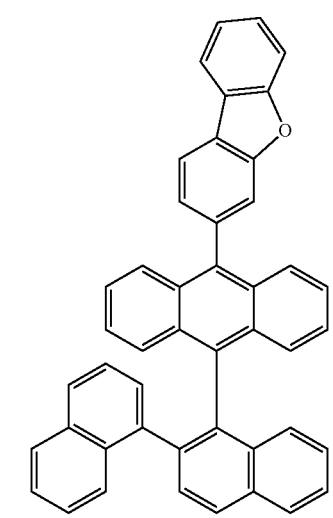

99
-continued
100
-continued
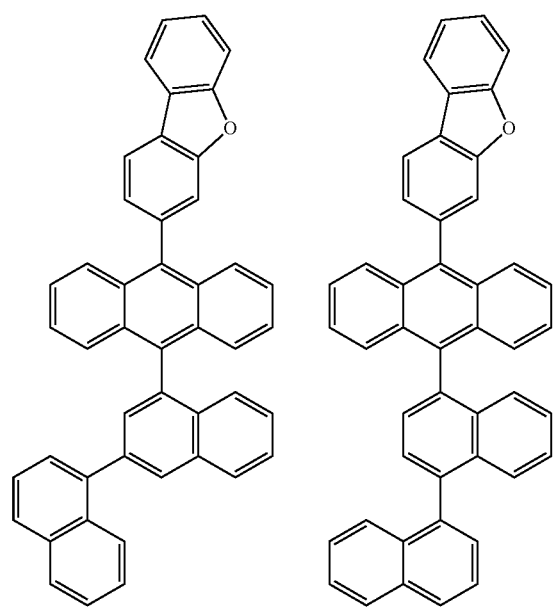
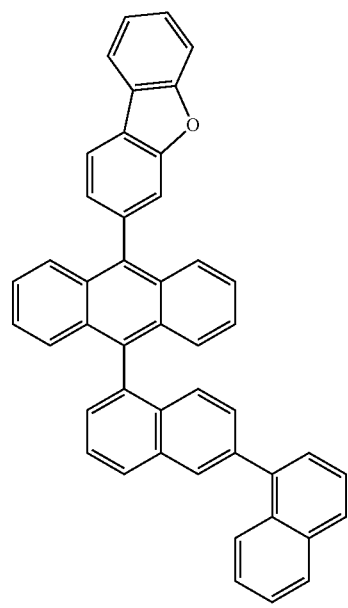

101
-continued
102
-continued
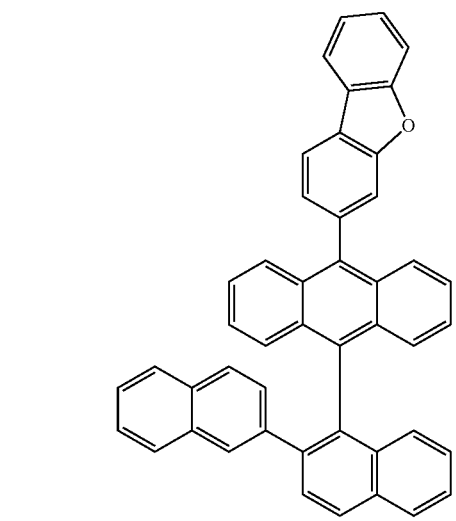
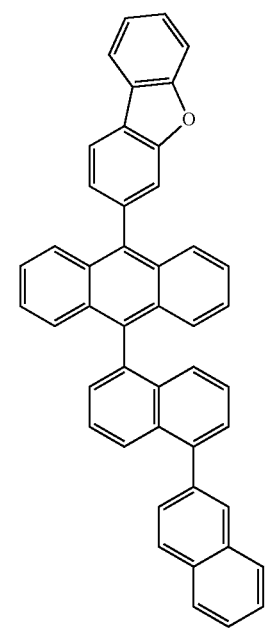
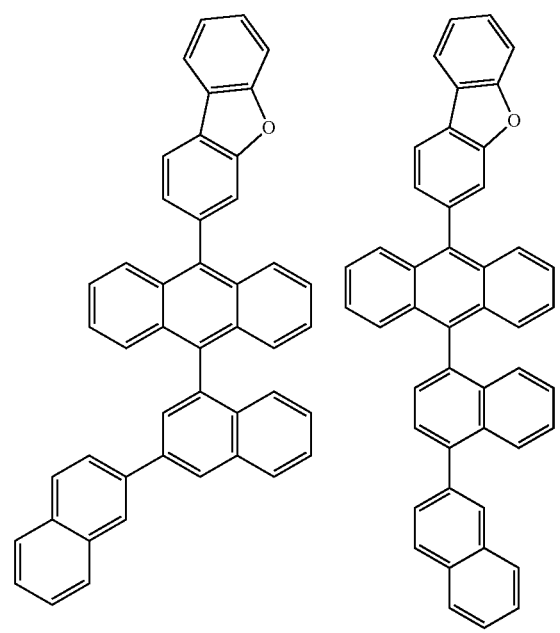
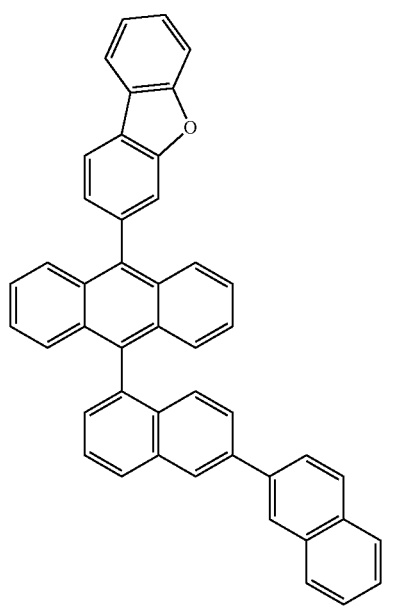
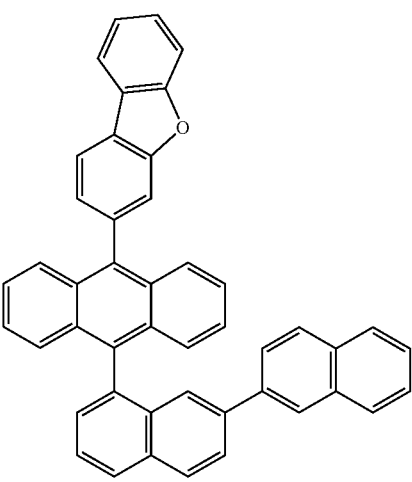

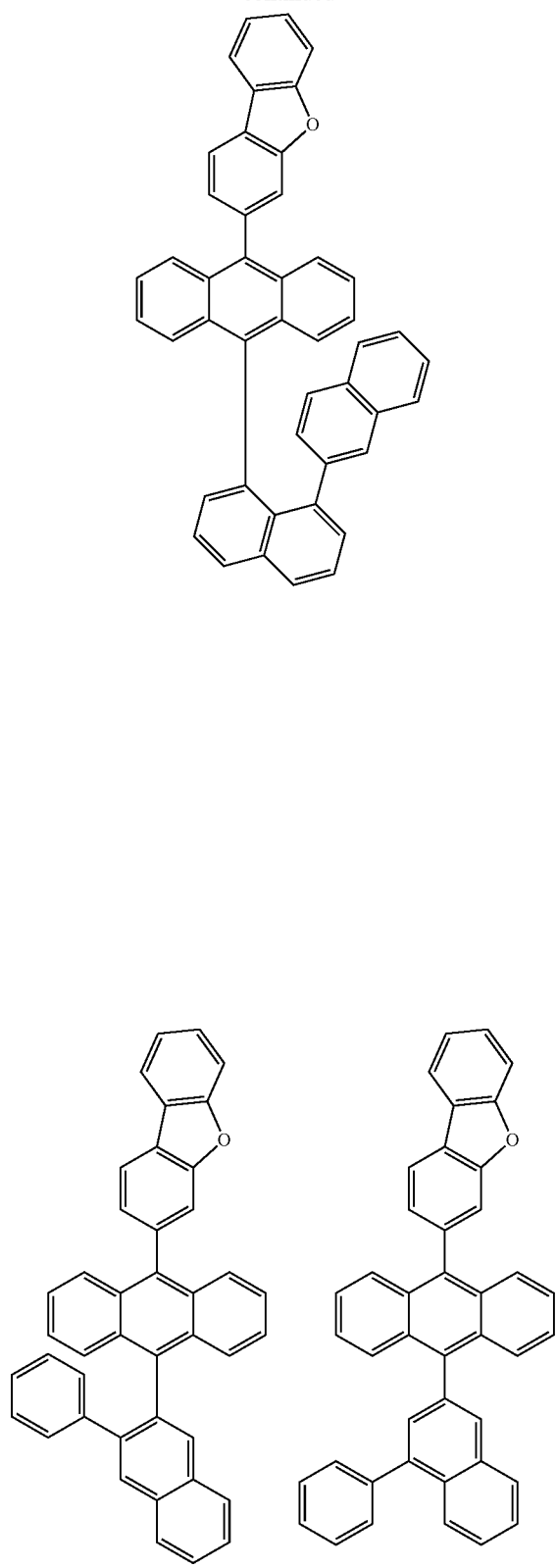
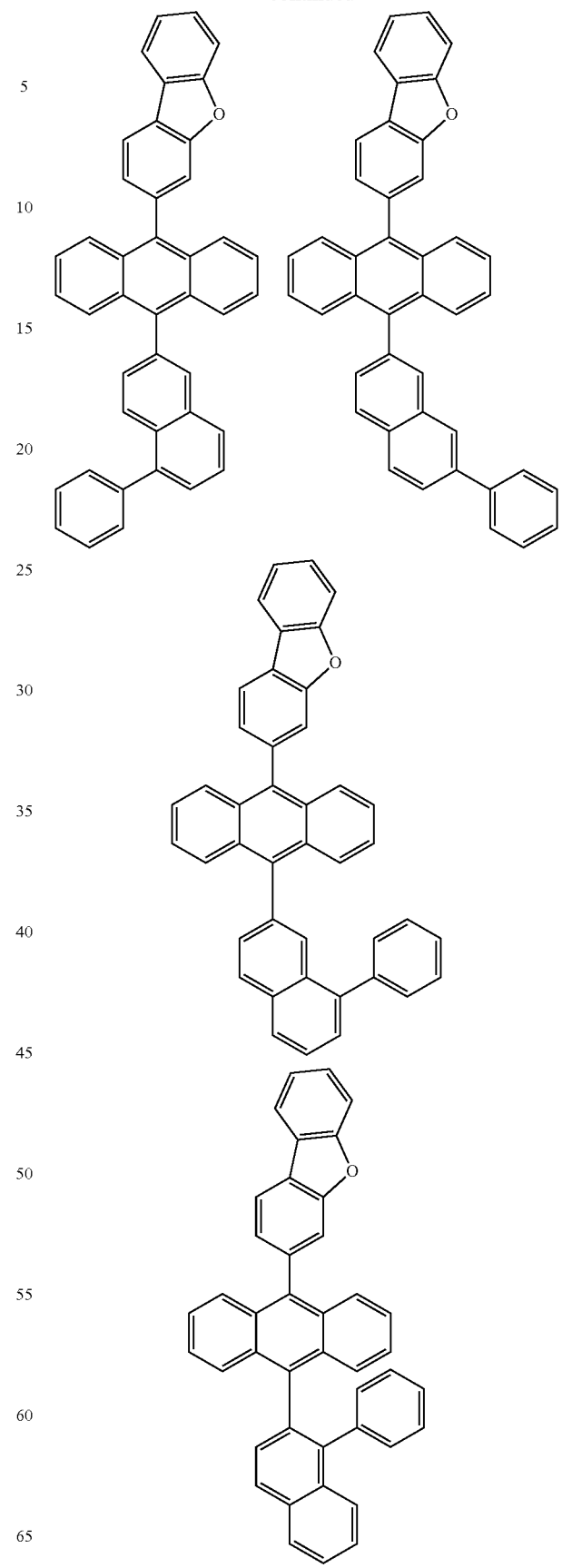

105
-continued
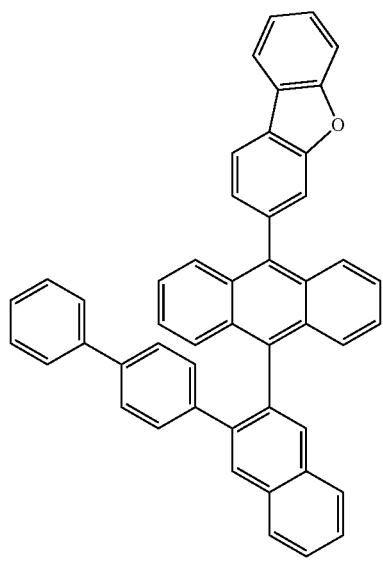
106
-continued
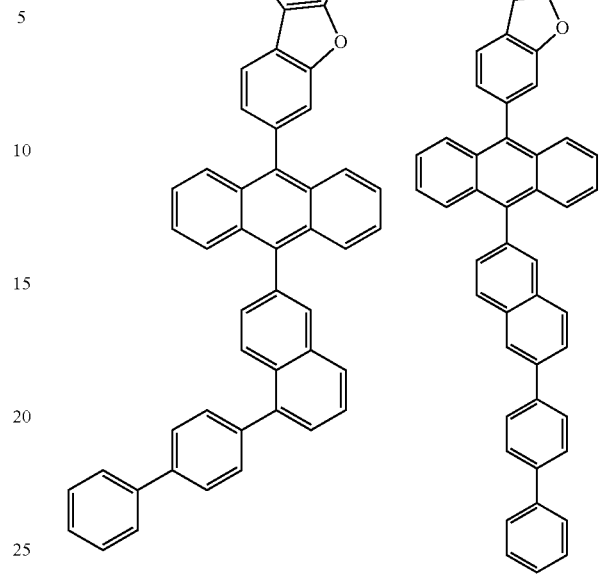
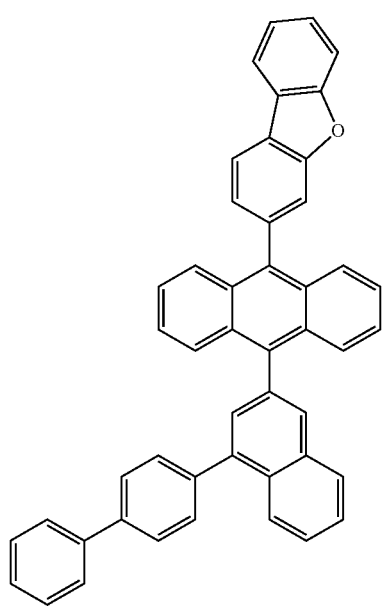
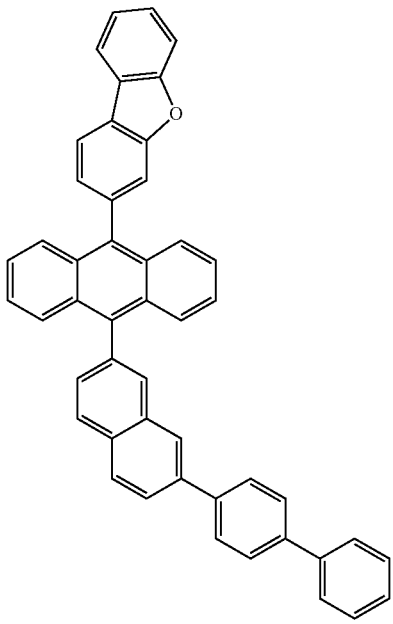

107
-continued
108
-continued
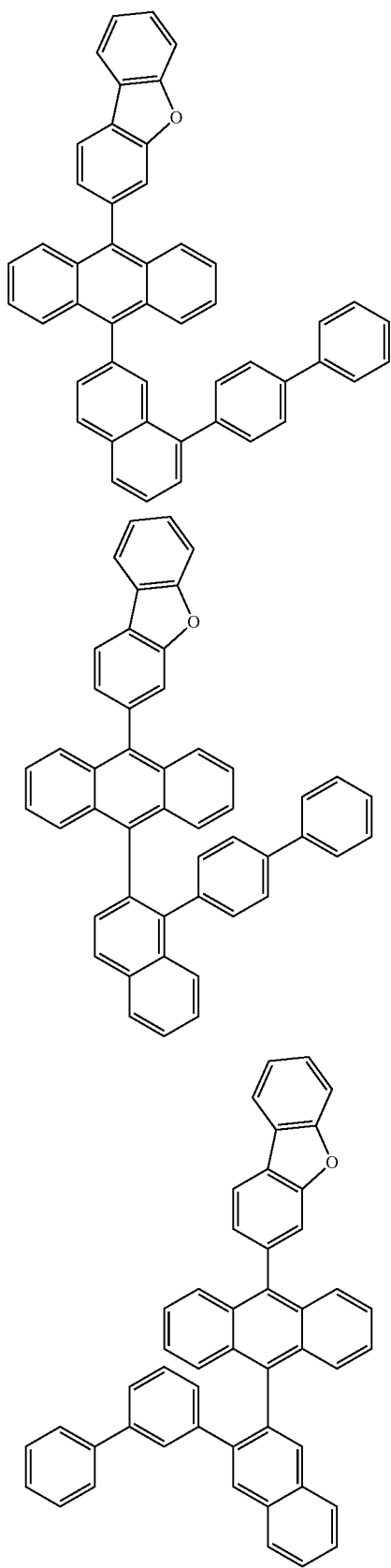
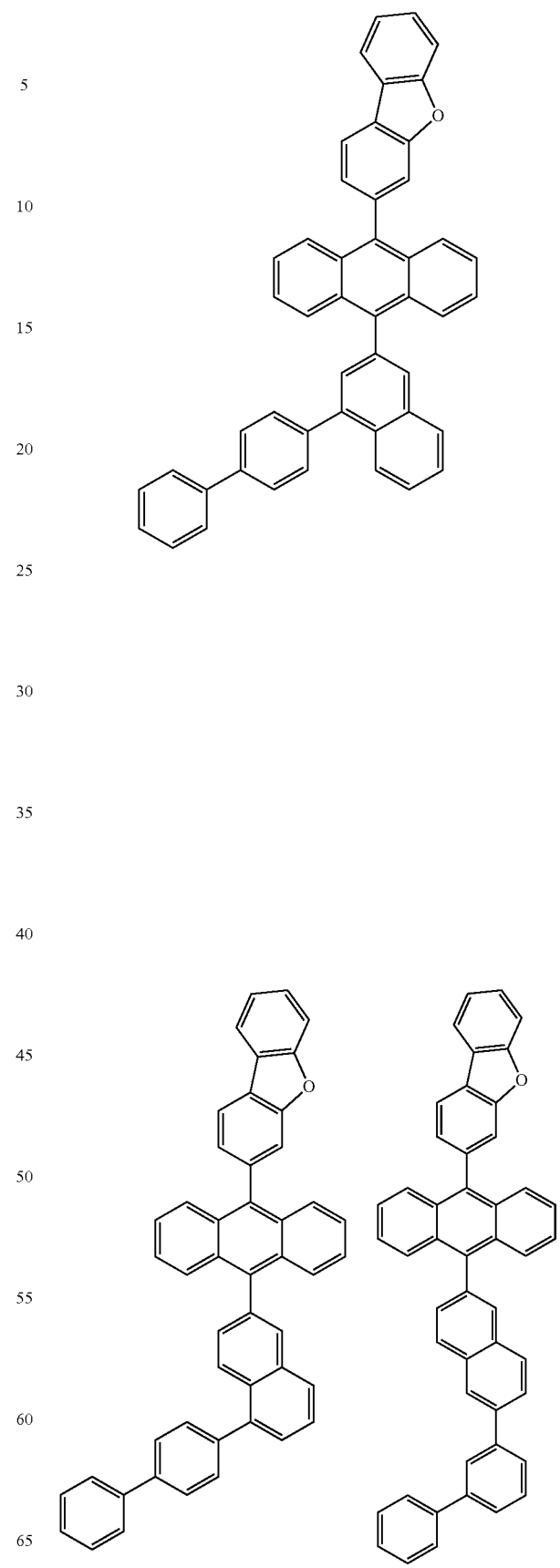

109
-continued
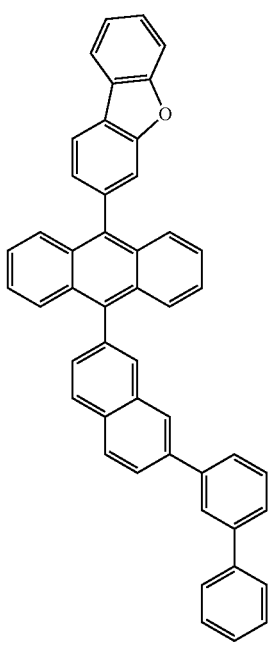
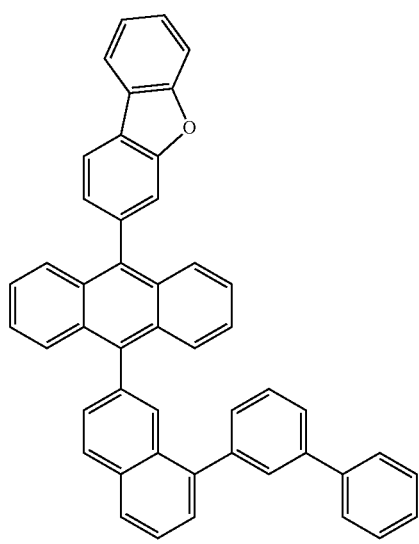
110
-continued
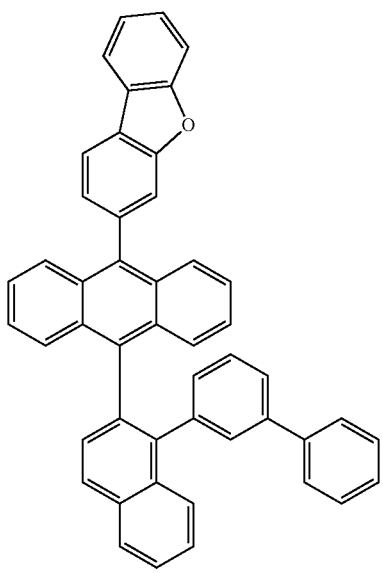
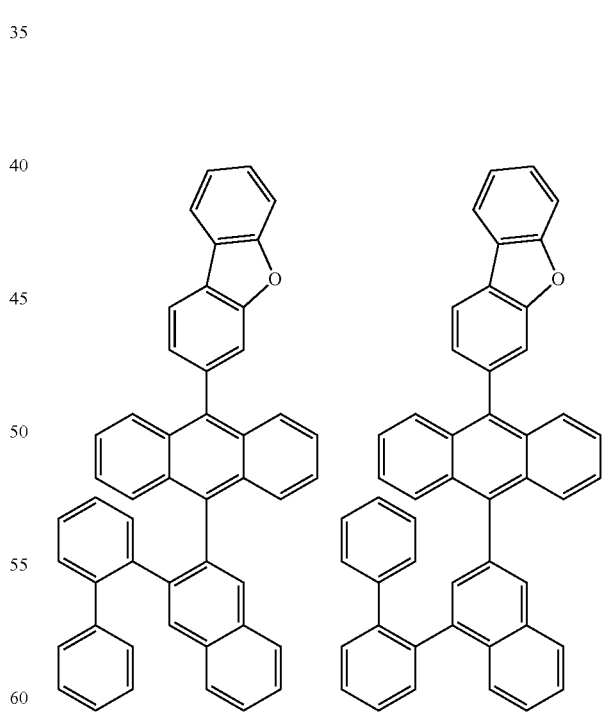

111
-continued
112
-continued
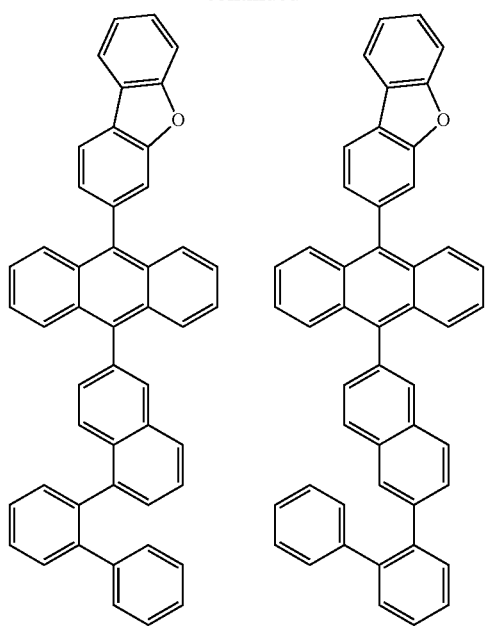
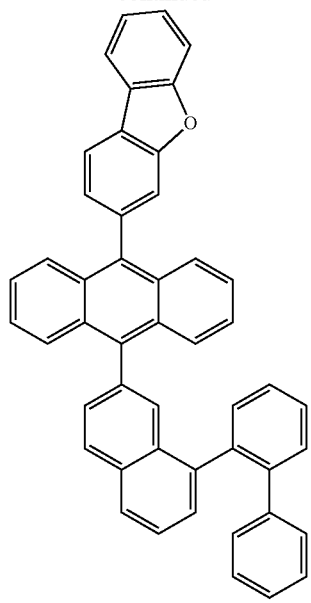
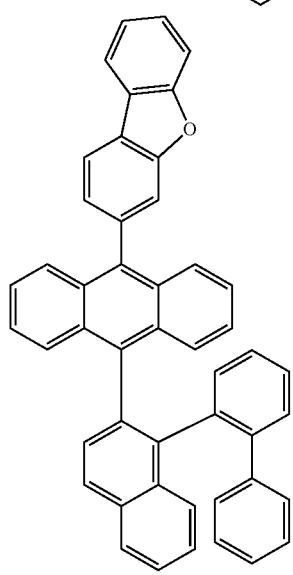
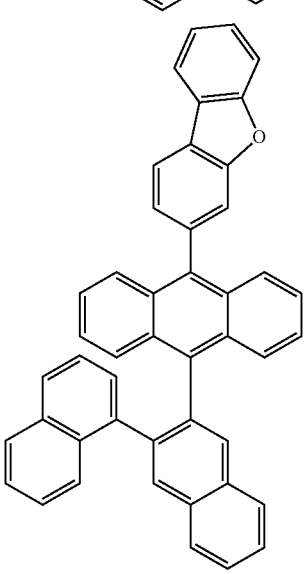

113
-continued
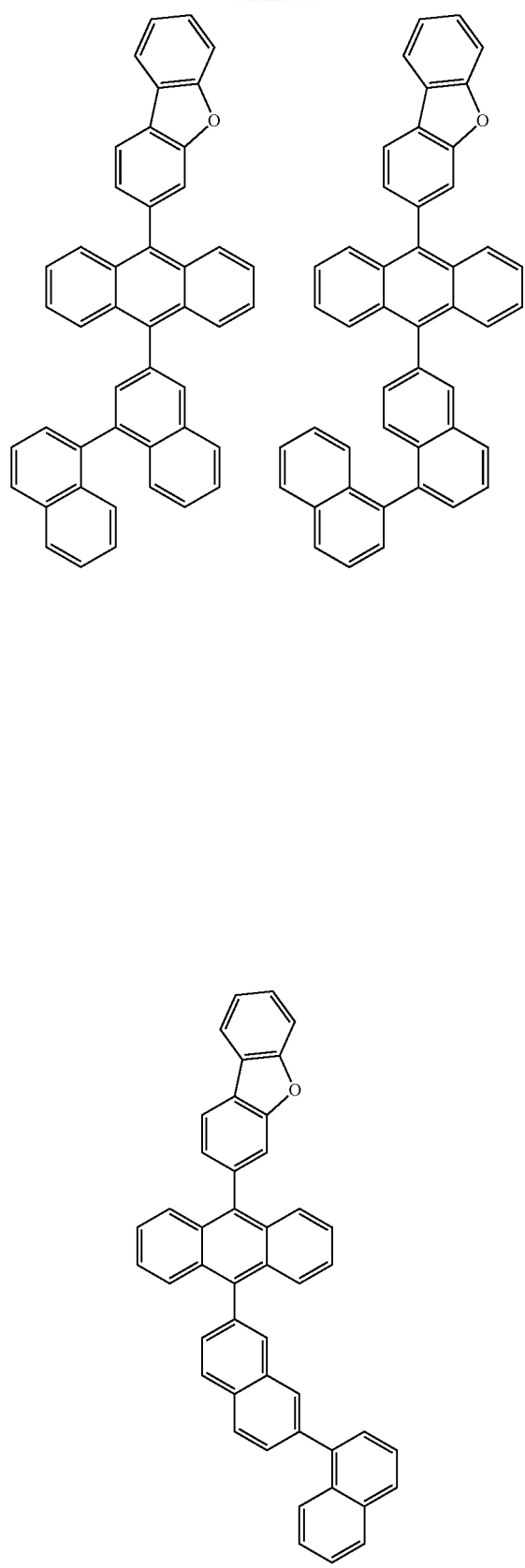
114
-continued
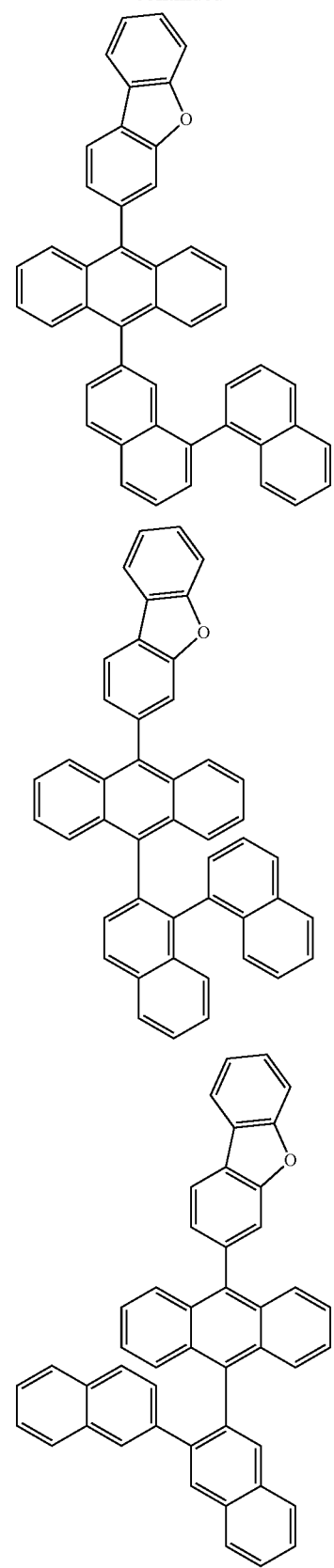

115
-continued
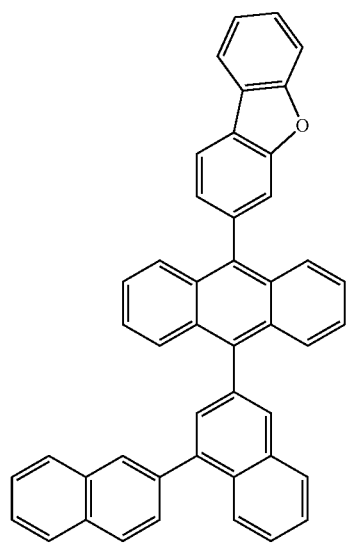
116
-continued
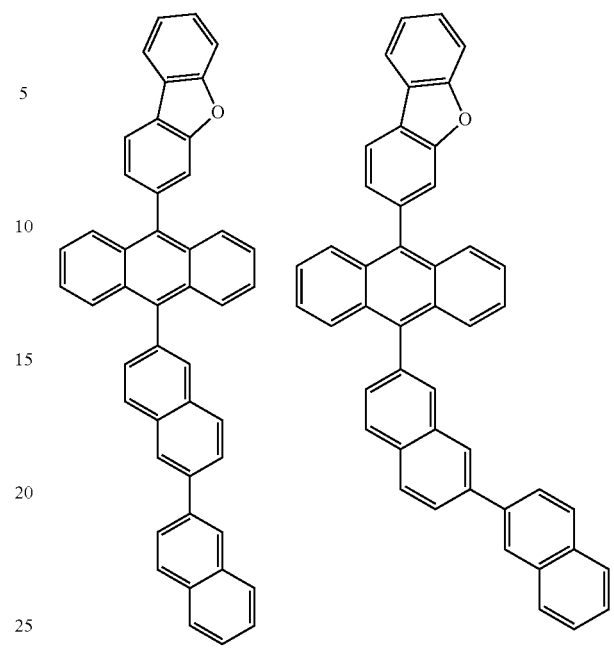
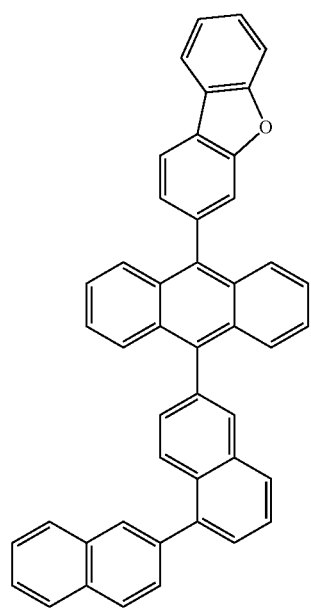
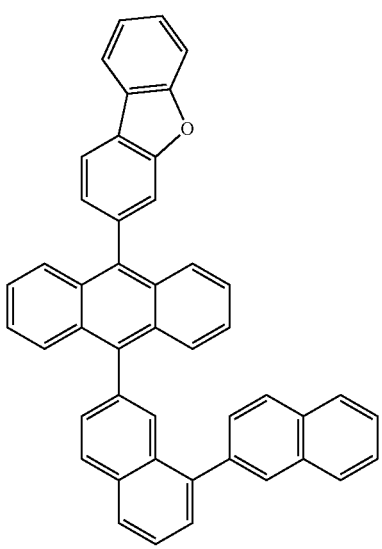

117
-continued
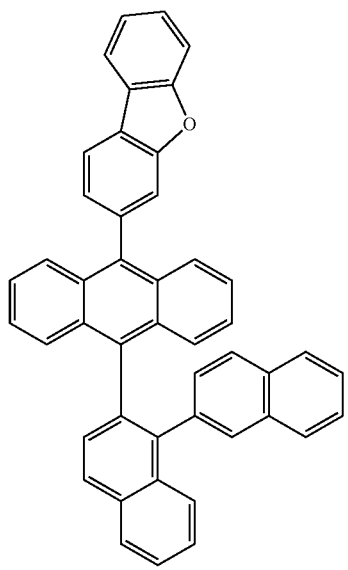
118
-continued
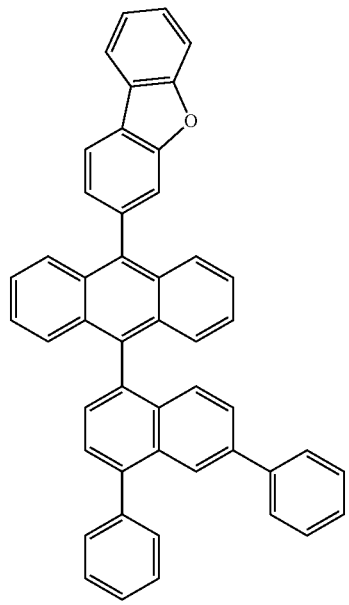
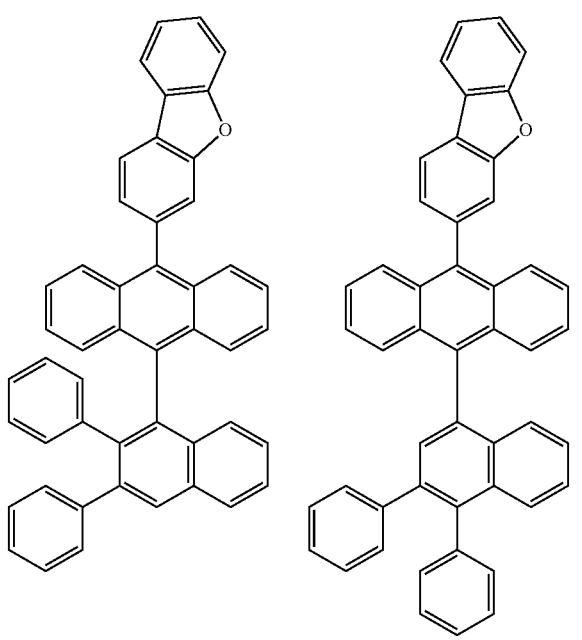
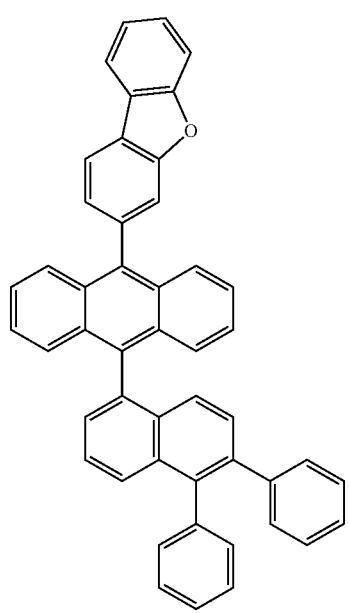

119
-continued
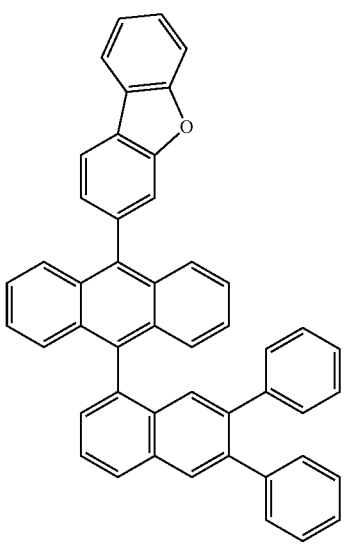
120
-continued
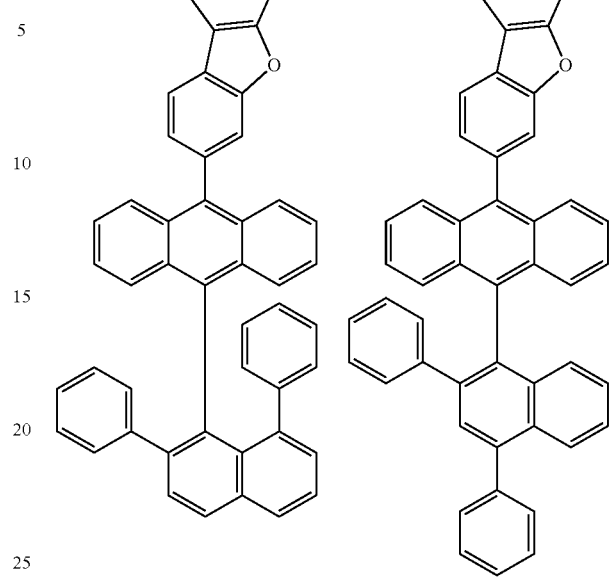
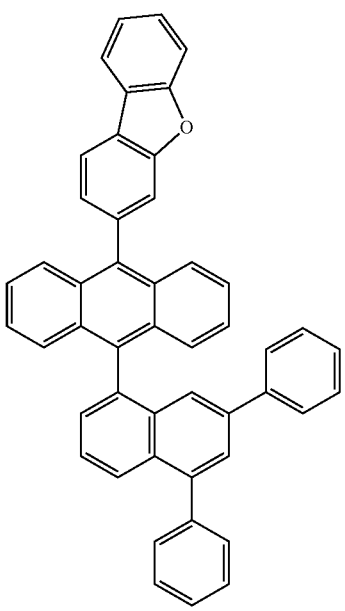
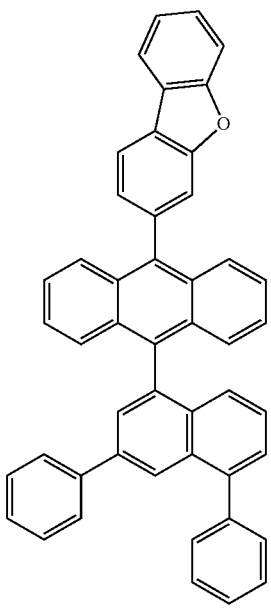

121
-continued
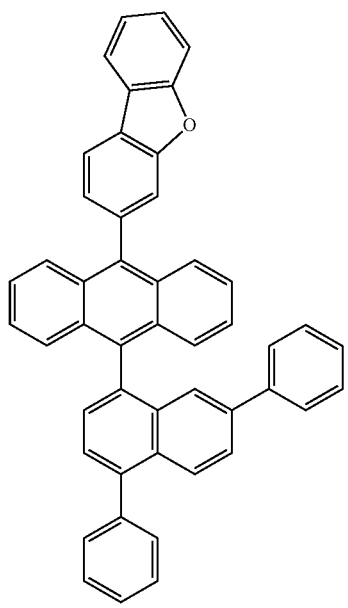
122
-continued
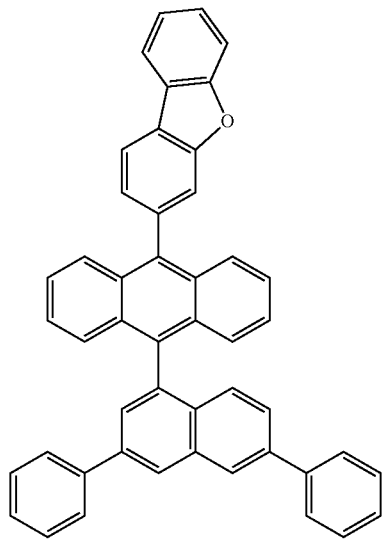
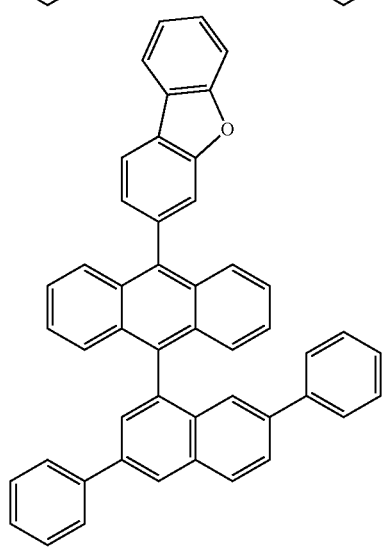
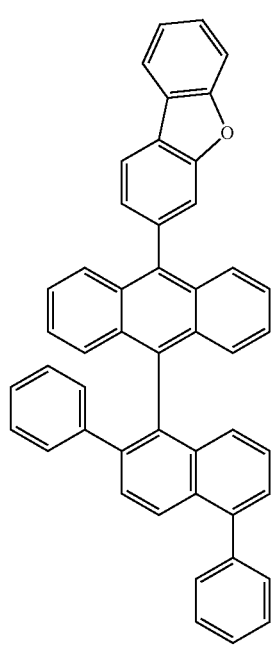
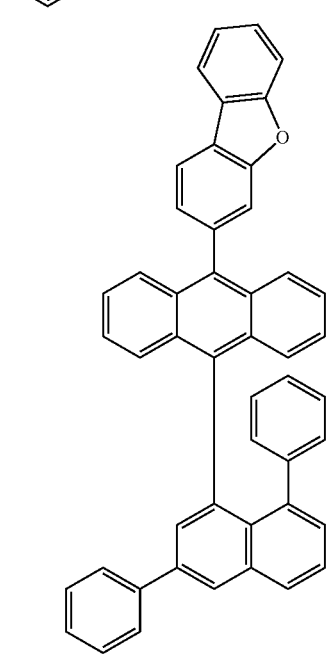

123
-continued
124
-continued
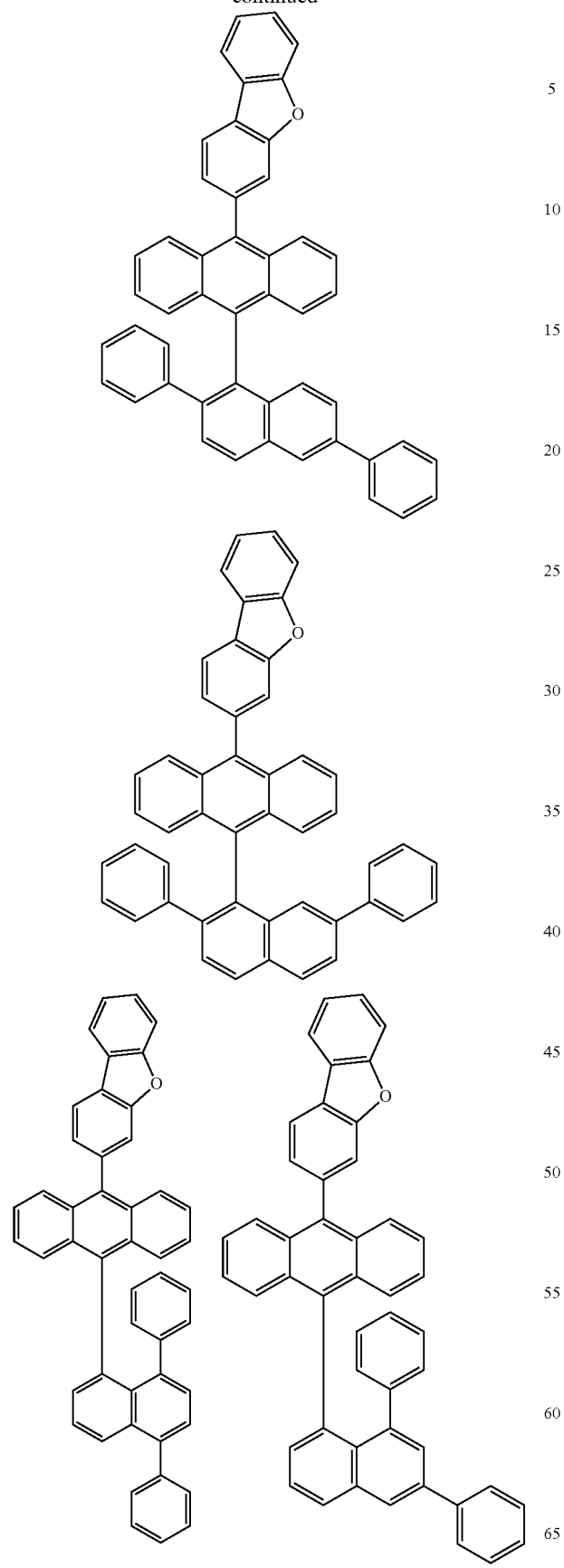

125
-continued
126
-continued
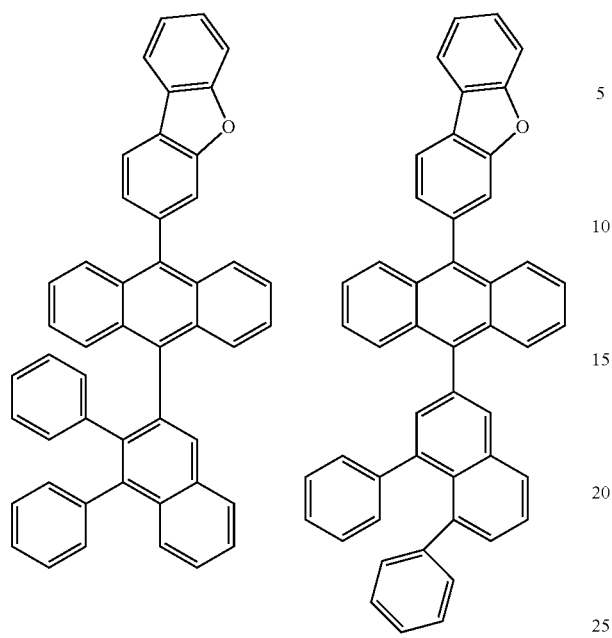
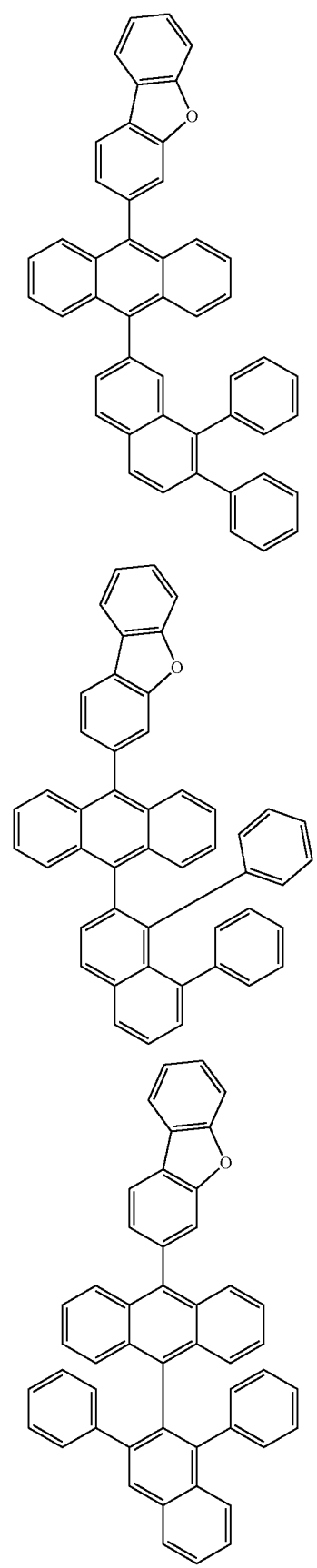

127
-continued
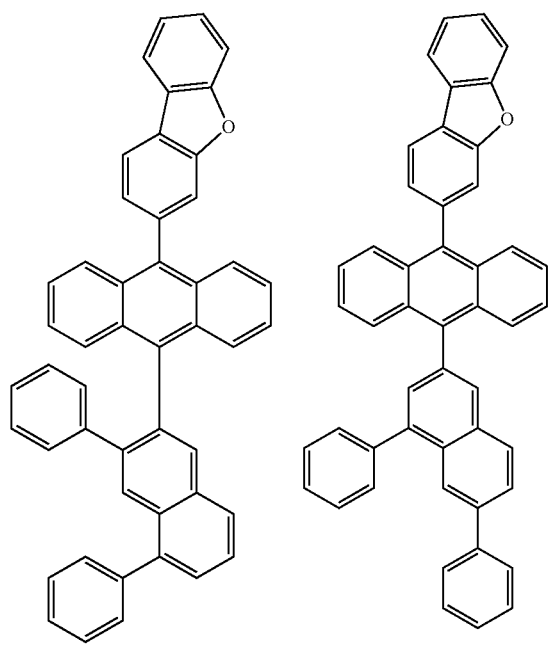
128
-continued
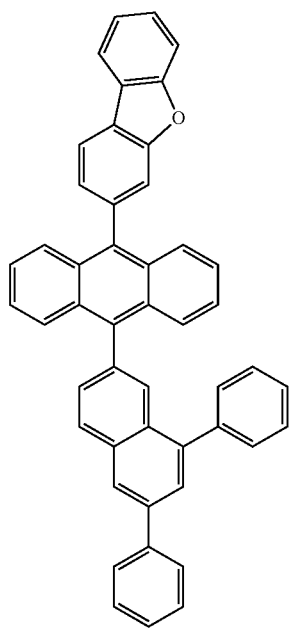
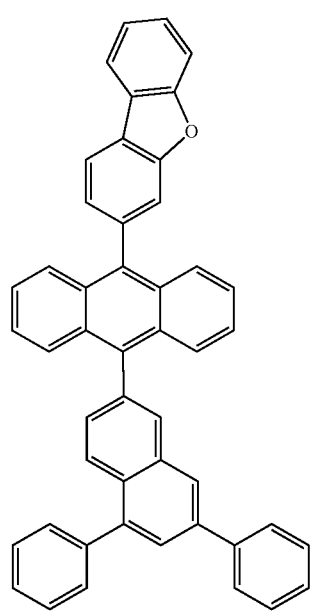
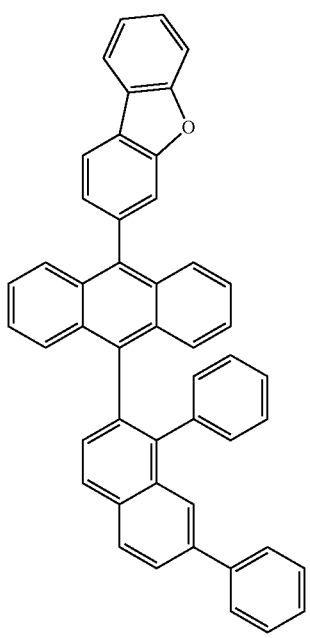

129
-continued
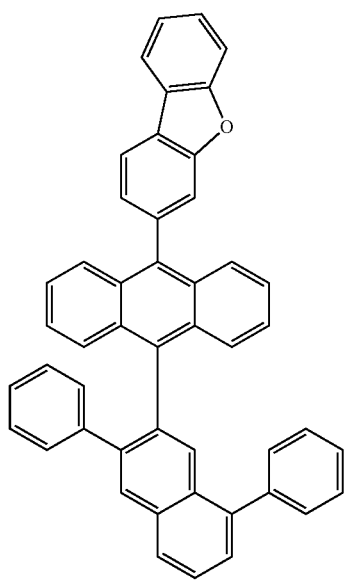
130
-continued
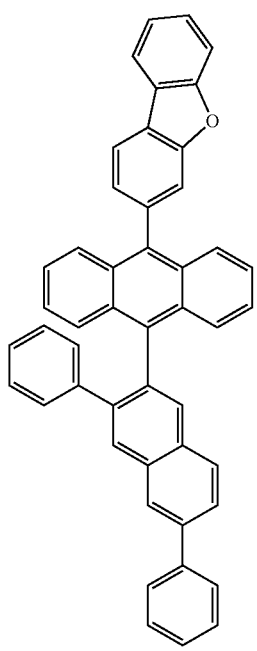
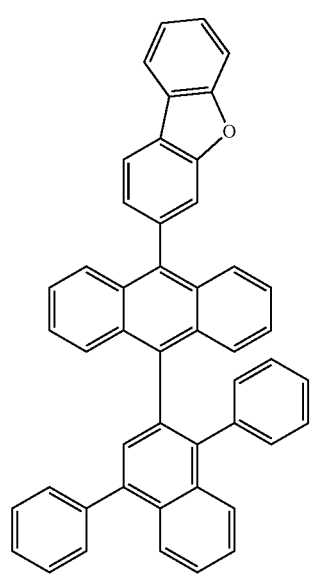
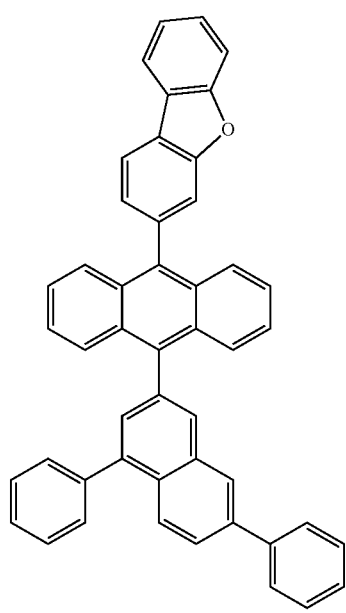

131
-continued
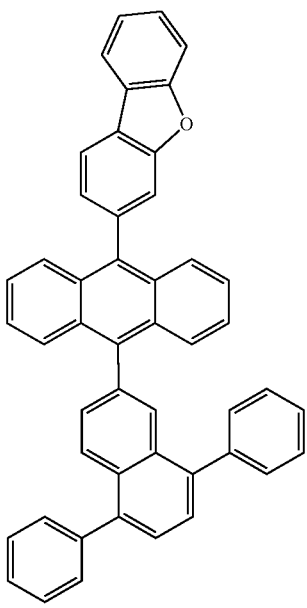
132
-continued
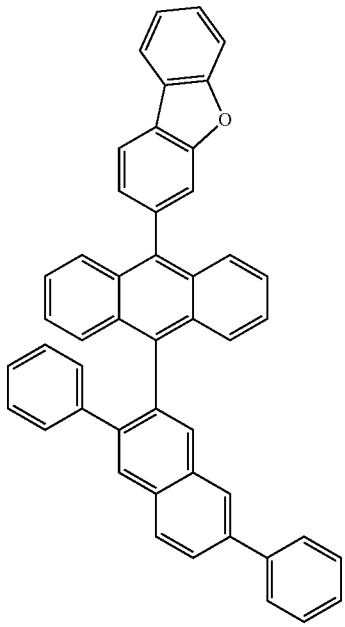
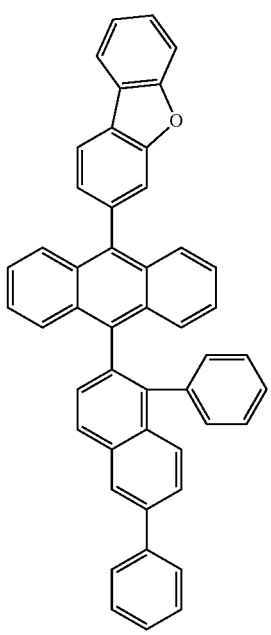
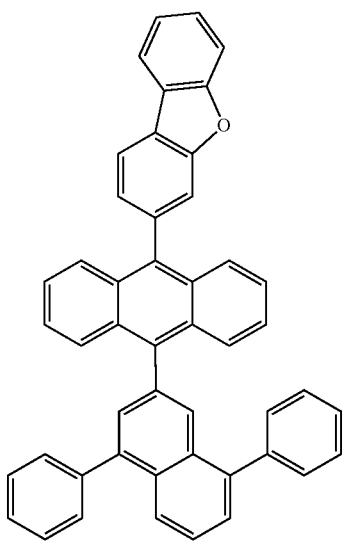

-continued

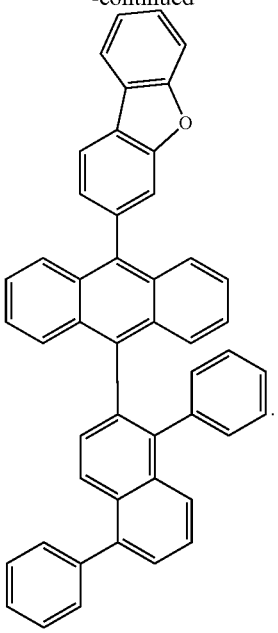

7. An organic light emitting device comprising:
a first electrode;
a second electrode provided to face the first electrode; and
an organic material layer having one or more layers provided between the first electrode and the second electrode,
wherein one or more layers of the organic material layer comprise the compound of claim 1.

8. The organic light emitting device of claim 7, wherein the organic material layer comprises a light emitting layer, and the light emitting layer comprises a host and a dopant at a mass ratio of 99:1 to 80:20.

9. The organic light emitting device of claim 7, wherein the organic material layer comprises a light emitting layer, and the light emitting layer comprises the compound as a host.

* * * * *